(12) United States Patent
Romano et al.

(10) Patent No.: US 11,426,382 B2
(45) Date of Patent: *Aug. 30, 2022

(54) SULCARDINE SALTS

(71) Applicant: HUYABIO International, LLC, San Diego, CA (US)

(72) Inventors: Suzanne J. Romano, Carlsbad, CA (US); Hayley Ann Reece, Dalkeith (GB); Joseph Edward Gordon Benson, Edinburgh (GB); Sarah Collins, Edinburgh (GB); Gary T. Elliott, San Diego, CA (US); Mireille Gillings, San Diego, CA (US); Robert Goodenow, San Diego, CA (US); Curtis Tyree, San Diego, CA (US)

(73) Assignee: HUYABIO International, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/775,142

(22) Filed: Jan. 28, 2020

(65) Prior Publication Data

US 2020/0316024 A1    Oct. 8, 2020

Related U.S. Application Data

(60) Provisional application No. 62/959,687, filed on Jan. 10, 2020, provisional application No. 62/798,467, filed on Jan. 29, 2019.

(51) Int. Cl.
*A61K 31/4025* (2006.01)

(52) U.S. Cl.
CPC ................ *A61K 31/4025* (2013.01)

(58) Field of Classification Search
CPC ................ A61K 31/4025; A61P 9/06
See application file for complete search history.

(56) References Cited

U.S. PATENT DOCUMENTS

| | | | |
|---|---|---|---|
| 6,605,635 | B1 | 8/2003 | Bai et al. |
| 8,541,464 | B2 | 9/2013 | Elliott |
| 8,637,566 | B2 | 1/2014 | Elliott |
| 10,143,626 | B2 | 12/2018 | Li |
| 10,258,575 | B2 | 4/2019 | Li |
| 10,363,220 | B2 | 7/2019 | Li |
| 2012/0245214 | A1 | 9/2012 | Elliott |
| 2012/0309810 | A1 | 12/2012 | Elliott |
| 2019/0192440 | A1 | 6/2019 | Li |
| 2020/0188357 | A1 | 6/2020 | Romano et al. |
| 2021/0038568 | A1 | 2/2021 | Romano et al. |

FOREIGN PATENT DOCUMENTS

| | | |
|---|---|---|
| CN | 1299813 C | 2/2007 |
| CN | 1939298 A | 4/2007 |
| WO | WO-0142204 A1 | 6/2001 |
| WO | WO-2011062903 A2 | 5/2011 |
| WO | WO-2011062906 A2 | 5/2011 |
| WO | WO-2018137686 A1 | 8/2018 |
| WO | WO-2020123824 A1 | 6/2020 |

OTHER PUBLICATIONS

Berge et al. J. Pharm. Sci., 1977, 66 (1), 1-19.*
Bai et al., Discovery of N-(3,5-bis(1-pyrrolidylmethyl)-4-hydroxybenzyl)-4-methoxybenzenesulfamide (sulcardine) as a novel anti-arrhythmic agent. Acta Pharmacologica Sinica 33(9):1176-1186 (2012).
Chen et al., Characteristics of hERG and hNav1.5 channel blockade by sulcardine sulfate, a novel anti-arrhythmic compound. European Journal of Pharmacology 844:130-138 (2019).
Lu et al., Oral bioavailability and mass balance studies of a novel anti-arrhythmic agent sulcardine sulfate in Sprague-Dawley rats and beagle dogs. European Journal of Drug Metabolism and Pharmacokinetics 42(3):453-459 (2017).
PCT/US2019/066003 International Search Report and Written Opinion dated Mar. 20, 2020.
PCT/US2020/015370 International Search Report and Written Opinion dated Jun. 6, 2020.
PCT/US2020/015370 Invitation to Pay Additional Fees dated May 15, 2020.
U.S. Appl. No. 16/712,677 Office Action dated Apr. 12, 2021.
"Drugs in Japan," Medicinal Drug Collection, Jiho Takeda, 27th Edition, 2004, p. 2631, p. 2386.
"Guidance of Industry—Estimating the Maximum Safe Starting Dose in Initial Clinical Trials for Therapeutics in Adult Healthy Volunteers," U.S. Department of Health and Human Services, Pharmacology and Toxicology, Jul. 2005, 30 pages.
Anonymous, A Phase 1, randomised, double-blind, placebo-controlled, serial cohort dose-escalation study of intravenously administered HB1-3000. Clinicaltrials.gov study# NCT03397641 (2018).
Anonymous, Abstracts from the 2009 Annual Meeting of the International Society for Heart Research North American Section: New Discoveries for Prevention and Treatment of Heart Disease. Baltimore, MD, United States. May 26, 2009-May 29, 2009. Journal of Molecular and Cellular Cardiology 46(5, Supp. 1) (2009).
Anonymous, HUYA Bioscience Int'l Announces First Pre-Ind Outcome For A Development Stage Compound Sourced From China—Hbi-8000, Promising New Cancer Compound. [Press release] https://www.huyabio.com/huya-bioscience-intl-announces-first-pre-ind-outcome- development-stage-compound-sourced-china-hbi-8000-promising-new-cancer-compound/ (2008).
Chen et al., Pharmacokinetics, safety, and tolerability of sulcardine sulfate: an open-label, single-dose, randomized study in healthy Chinese subjects. Fundamental & Clinical Pharmacology 31(1):120-125 (2017).
Chinese Office Action for CN201080051906, dated Jun. 23, 2014 (4 pages, English Translation).

(Continued)

*Primary Examiner* — Alicia L Otton
(74) *Attorney, Agent, or Firm* — Eversheds Sutherland (US) LLP

(57) ABSTRACT

Sulcardine salts other than sulfuric acid salts of sulcardine, including crystalline sulcardine salts, are provided herein. Pharmaceutical compositions comprising such salts and methods of treating arrhythmias comprising administering effective amounts of such salts are also provided.

3 Claims, 42 Drawing Sheets

(56) References Cited

OTHER PUBLICATIONS

Chinese Office Action for CN2014104749461, dated Dec. 30, 2015 (5 pages, English Translation).
Chinese Office Action for CN201510364466, dated Aug. 9, 2017 (7 pages, English Translation).
Chinese Search Report for CN2010800519066, dated Jun. 13, 2014, (1 Page).
Chinese search report for CN2010800519070, dated Aug. 6, 2013 (1 page).
Chinese search report for CN2014104749461, dated Dec. 17, 2015 (1 page).
Chinese search report for CN201510364466, dated Jul. 20, 2017 (2 pages).
Chinese search report for CN2020800047961, dated Aug. 19, 2021 (1 pages).
David C. Lee and Michael L. Webb, Pharmaceutical Analysis, Wiley-Blackwell, Feb. 2009, pp. 255-257.
European Supplementary Search Report for EP10832056 dated Apr. 22, 2013 (5 pages).
European Supplementary Search Report for EP10832058 dated May 14, 2013 (5 pages).
European Supplementary Search Report for EP17182709 dated Mar. 22, 2018 (6 pages).
Guo et al., Electrophysiologic effect of HB1-3000: A novel antiarrhythmic compound with multiple channels blocking characteristics in human atrial and ventricular myocytes. Journal of Molecular and Cellular Cardiology 46(5, Supp. 1):S4-S5; abstract p. 11 (2009).
Guo et al., Electrophysiological properties of HB1-3000: a new antiarrhythmic agent with multiple-channel blocking properties in human ventricular myocytes. Journal of Cardiovascular Pharmacology 57(1):79-85 (2011).
Japanese Decision of Refusal for JP2012-539070, drafted Apr. 2, 2015, (4 pages with English Translation).
Japanese Decision of Refusal for JP2012-539071, drafted Apr. 22, 2015, (5 pages with English Translation).
Japanese Notice of Reasons of Refusal for JP2015-157843, drafted May 27, 2016 (4 pages, English Translation).
Japanese Notice of Reasons of Refusal for JP2015-171604, drafted Jul. 22, 2016 (2 pages, English Translation).
Japanese Notice of Reasons of Refusal for JP2015-171604, drafted Nov. 14, 2016 (3 pages, English Translation).
Jia et al., Determination of the novel antiarrhythmic drug sulcardine sulfate in human plasma by liquid chromatography tandem mass spectrometry and its application in a clinical pharmacokinetic study. Biomedical Chromatography 30(8):1291-1296 (2016).
Lapointe, et al., "Continuous intravenous quinidine infusion for the treatment of atrial fibrillation or flutter: A case series." American Heart Journal 139.1, Jan. 2000, pp. 114-121.
Lee at al., HB1-3000 prevents secondary sudden cardiac death. Journal of Cardiovascular Pharmacology and Therapeutics 18(5):453-459 (2013).
Lee et al., Antifibrillatory actions of HB1-3000 in the conscious canine model of sudden cardiac death. The FASEB Journal 23(S1):LB376 [Abstract XP009168686] (2009).
Lee et al., HB1-3000 prevents sudden cardiac death in a conscious canine model. Cardiac Electrophysiology Society, CES Annual Meeting. Chicago, IL, United States. Nov. 13, 2010-Nov. 13, 2010; Heart Rhythm 7(11):1712 (2010).
Mason, et al. "HBI-3000: A Novel Drug for Conversion of Atrial Fibrillation-Phase I Study Results." HUYA Bioscience International, Circulation 140, Suppl, 1, 2019, p. All495.
PCT/US2021/37098 International Search Report and Written Opinion dated Oct. 6, 2021 (3 pages).
Qi et al., Innovative drug R&D in China. Nature Reviews Drug Discovery 10(5):333-334 (2011).
Singh, et al., "N-Acylated sulfonamide sodium salt: A prodrug of choice for the bifunctional 2-hydroxymethyl-4-(5-phenyl-3-trifluoromethyl-pyrazol-1-yl) benzenesulfonamide class of COX-2 inhibitors," Bioorganic & Medicinal Chemistry Letters, vol. 16, May 11, 2006, pp. 3921-3926.
Streitwiesser et al., "Introduction to Organic Chemistry", Macmillan Publishing Co., 1992, p. 736.
Wang, et al., "Electrophysiological Characterization of a Novel Artiarrhythmic Agent—Sulcardine Salts," AACTA Pharmacologica Sinica, Jul. 2006. vol. 27, Suppl. 1, p. 123.
Wang et al., Multiple dose pharmacokinetics and safety of sulcardine sulfate in healthy Chinese male subjects: an open-label phase I clinical study. European Journal of Drug Metabolism and Pharmacokinetics 42(4):593-599 (2017).
Wang, et al., "Effect of Sulcardine on cardiac electrophysiology in anesthetized rabbits," Chinese Pharmacological Society Communication vol. 19, No. 4, Nov. 4, 2002, pp. 63-64.

* cited by examiner

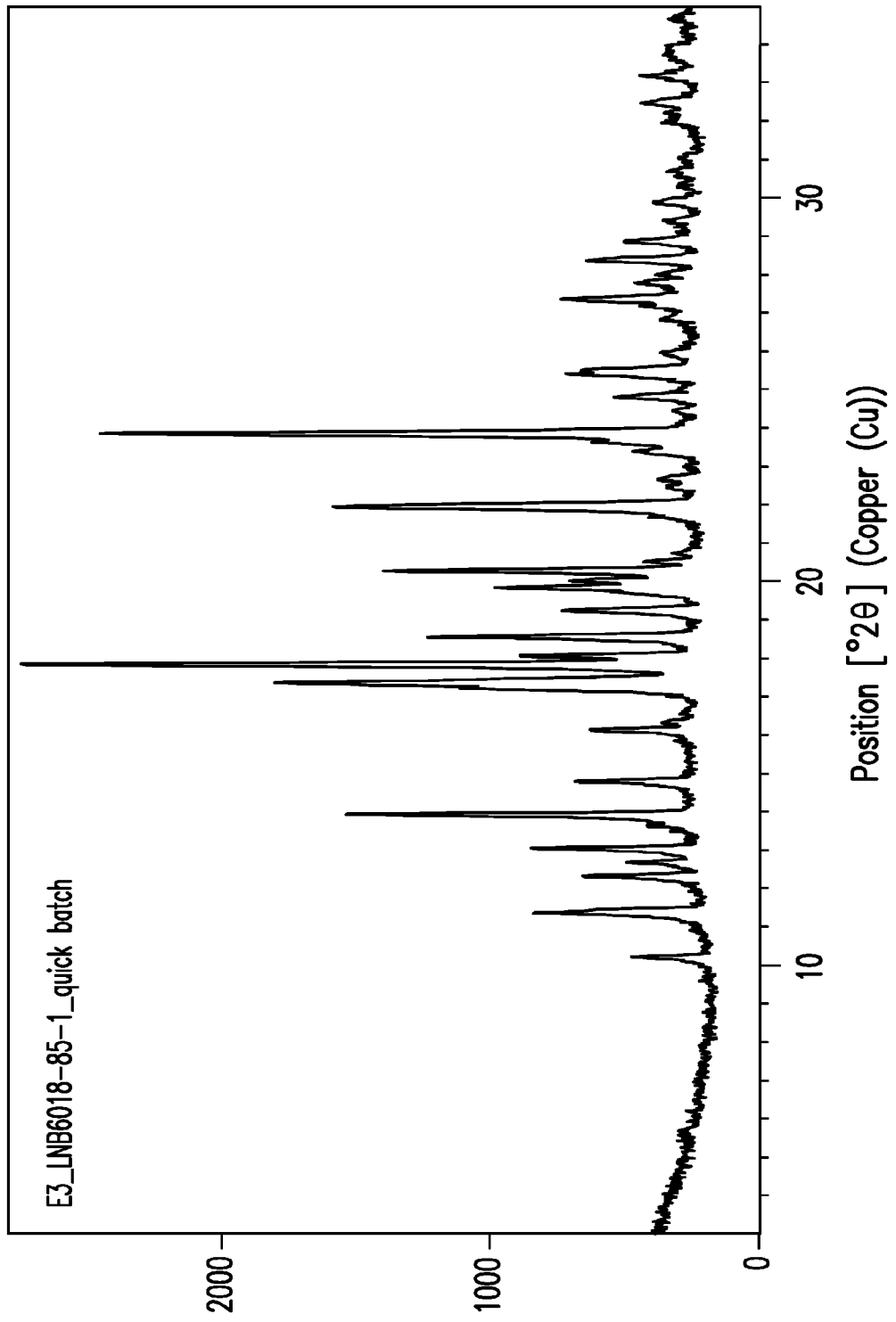

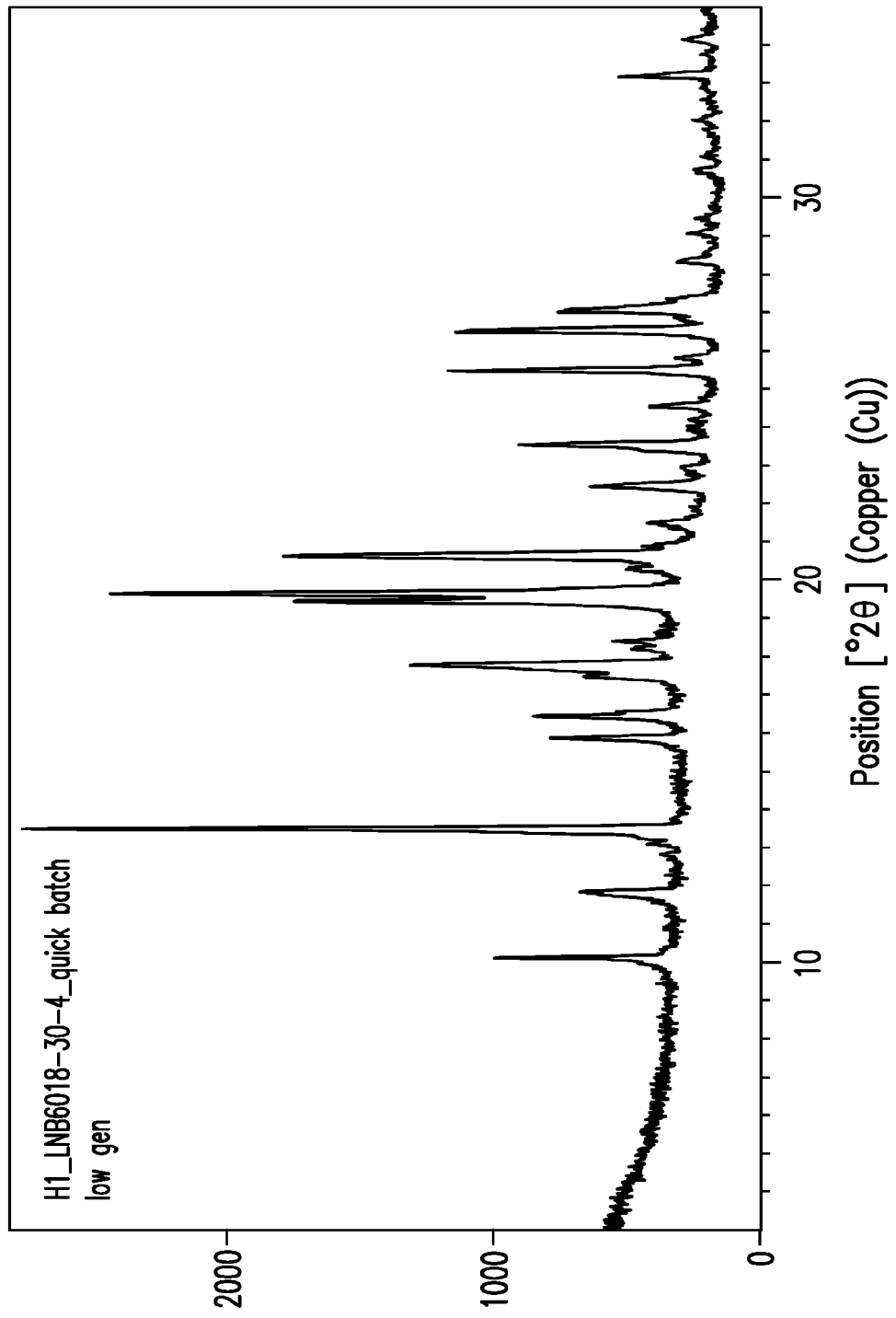

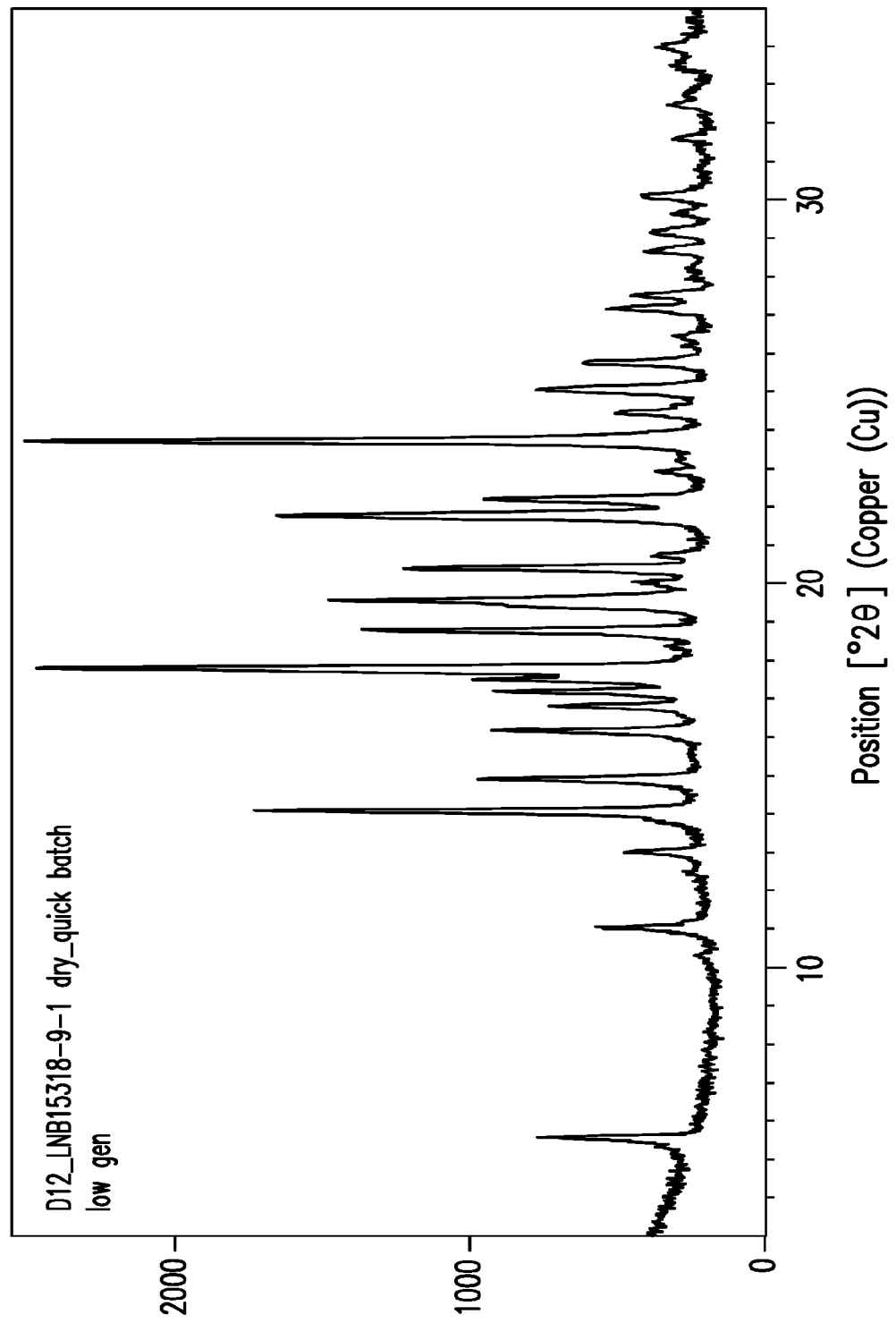

¹H-NMR spectrum of Form I of monoedisylate salt of sulcardine
(1.02 eq. of 1,2-ethanedisulfonic acid, LNB15318-53-1)

¹H-NMR spectrum of Form II of monoedisylate salt of sulcardine (1.07 eq. of 1,2-ethanedisulfonic acid, LNB1919-44-3)

Overlay of the asymmetric unit containing one complete sulcardine 1-hydroxy-2-naphthoate formula unit and schematic representation of sulcardine 1-hydroxy-2-naphthoate

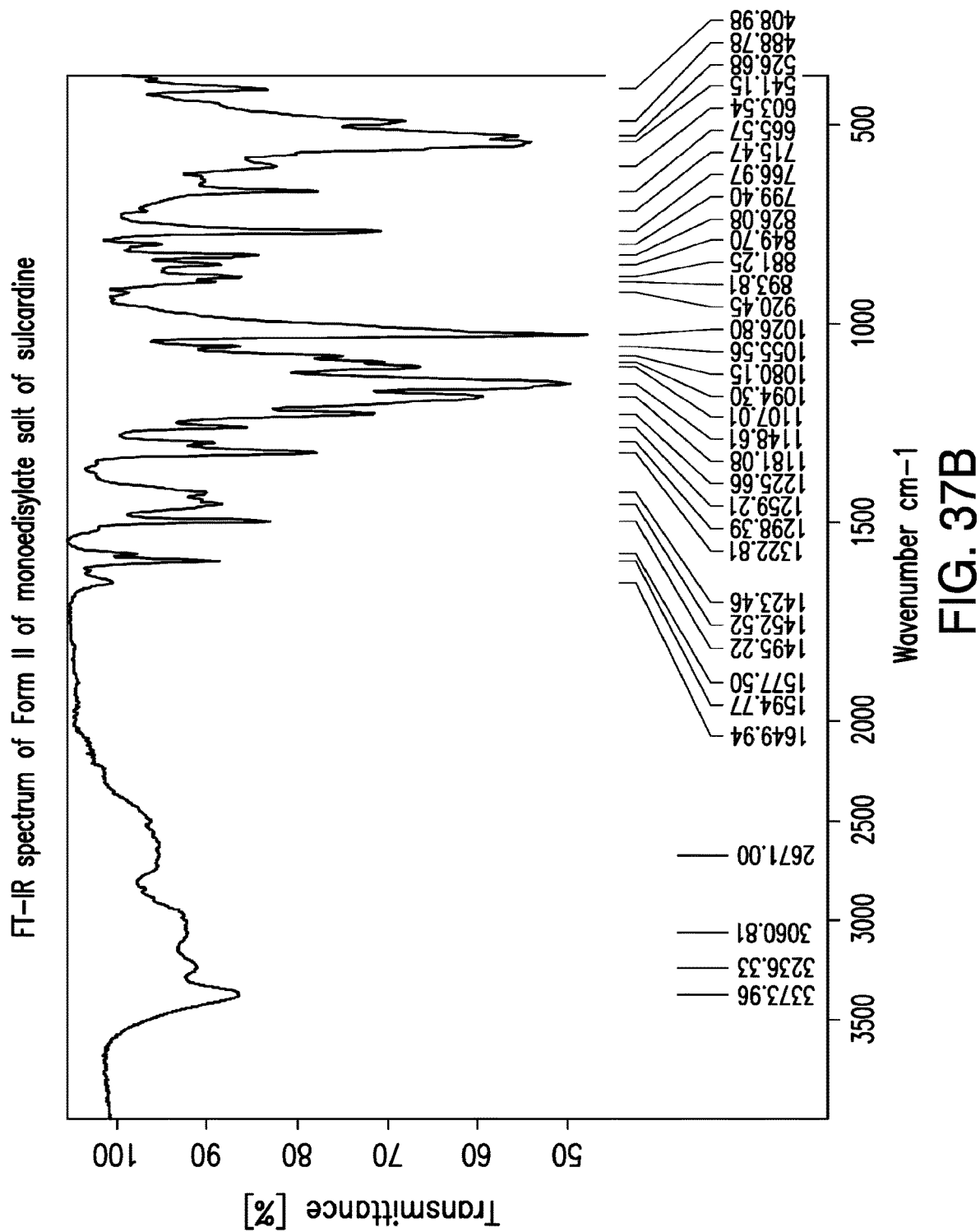

US 11,426,382 B2

SULCARDINE SALTS

CROSS-REFERENCE TO RELATED APPLICATIONS

This application claims priority to U.S. Provisional Application No. 62/798,467, filed on Jan. 29, 2019, and 62/959,687, filed on Jan. 10, 2020, the entireties of which are incorporated herein by reference.

FIELD

Sulcardine salts other than sulfuric acid salts of sulcardine, including crystalline sulcardine salts, are provided herein. In addition, pharmaceutical compositions comprising such salts and methods of treating arrhythmias comprising administering effective amounts of such salts are also provided.

BACKGROUND

4-Methoxy-N-(3,5-bis-(1-pyrrolidinylmethyl)-4-hydroxybenzyl)benzene sulfonamide (or N-(4-hydroxy-3,5-bis(pyrrolidin-1-ylmethyl)benzyl)-4-methoxybenzenesulfonamide), also known as sulcardine, and its salts, such as sulcardine sulfate, constitute a group of compounds with potent anti-arrhythmic activity. Sulcardine is a multi-ion channel blocker that specifically inhibits $I_{Na\text{-}Peak}$, $I_{Na\text{-}Late}$, $I_{Ca,L}$, and $I_{Kr}$ with similar in vitro potencies (and $I_{to}$ and $I_{Kur}$ to a lesser degree) in human atrial cardiomyocytes and represents what may be the sole example of a substituted sulfonamide class of anti-arrhythmic. Sulcardine salts can be used as an intravenous injectable or as oral doses for the treatment of arrhythmias, including supraventricular tachyarrhythmia, premature ventricular contractions, ventricular tachycardia, ventricular fibrillation, and atrial fibrillation. See, e.g., U.S. Pat. Nos. 8,541,464 and 8,637,566. Preparation of sulcardine sulfate salt has been reported in U.S. Pat. No. 6,605,635.

In addition, the evidence to date suggests that one advantage of sulcardine and its salts is that they lack significant pro-arrhythmic activity, as demonstrated in rigorous preclinical safety models, including a post-MI sudden-death conscious canine model and the validated rabbit ventricular wedge model. Additionally, it has been shown that they do not significantly increase defibrillation threshold, nor increase defibrillation failure risk in a post-MI canine model as was seen with flecainide. On the basis of these data, sulcardine and salts, with their very low apparent pro-arrhythmic potential, could potentially be used to treat acute and recurrent atrial fibrillation in the presence of organic heart disease, prolonged QR syndrome, and ventricular arrhythmias, including premature ventricular contractions (PVCs), ventricular tachycardia (VT), and ventricular fibrillation (VF), in either acute- or chronic-administration settings owing to their ability to be formulated into intravenous and oral dosing formulations.

SUMMARY

In some embodiments, crystalline salts of sulcardine and salt formers other than sulfuric acid are provided. A "salt former" is a compound (e.g., an acid counterion) which may be used to create a salt with, for example, sulcardine.

In some embodiments, provided herein is a solid form comprising an acid salt of sulcardine, wherein the acid is ethane-1,2-disulfonic acid, naphthalene-1,5-disulfonic acid, 1-hydroxy-2-naphthoic acid, naphthalene-2-sulfonic acid, hydrochloric acid, or hydrobromic acid. In some embodiments, the solid form is crystalline. In some embodiments, the solid form is amorphous.

In further embodiments, crystalline salts of sulcardine and halide salt formers are provided.

In additional embodiments, crystalline salts of sulcardine and a sulfonic acid salt former are provided.

In other embodiments, salts of sulcardine and mononaphthalene salt formers are provided.

In further embodiments, salts of sulcardine and naphthalene-1,5-disulfonic acid, 1-hydroxy-2-naphthoic acid, naphthalene-2-sulfonic acid, hydrochloric acid, or hydrobromic acid are provided.

In additional embodiments, crystalline salts of sulcardine and naphthalene-1,5-disulfonic acid, 1-hydroxy-2-naphthoic acid, naphthalene-2-sulfonic acid, hydrochloric acid, or hydrobromic acid are provided.

In additional embodiments, Form I and Form II of crystalline salts of sulcardine and 1-hydroxy-2-naphthoic acid are provided.

In further embodiments, Form I and Form II of crystalline salts of sulcardine and hydrochloric acid are provided.

In additional embodiments, monoedisylate salts (i.e., mono-ethane-1,2-disulfonic acid salts) of sulcardine are provided. In some embodiments, the monoedisylate salts of sulcardine are hydrates.

In other embodiments, crystalline monoedisylate salts of sulcardine are provided. In additional embodiments, amorphous monoedisylate salts of sulcardine are provided.

In still further embodiments, Form I and Form II of crystalline salts of monoedisylate sulcardine are provided.

In additional embodiments, pharmaceutical compositions comprising sulcardine salts provided herein, including crystalline salts, and one or more pharmaceutically acceptable excipients are provided.

In some embodiments, provided herein is a pharmaceutical composition comprising a solid form provided herein, and one or more pharmaceutically acceptable excipients.

In yet additional embodiments, methods of treating arrhythmias with sulcardine salts provided herein, including crystalline sulcardine salts, comprising administering such salts to a patient in need thereof are provided.

In some embodiments, provided herein is a method of treating arrhythmia, comprising administering to a subject in need thereof a therapeutically effective amount of a solid form provided herein, or a pharmaceutical composition provided herein. In some embodiments, the arrhythmia is atrial fibrillation, supraventricular tachyarrhythmia, premature ventricular contraction, ventricular tachycardia, or ventricular fibrillation.

BRIEF DESCRIPTION OF THE FIGURES

FIG. 17 is a representative XRPD pattern of Form I of a crystalline salt of sulcardine and hydrochloric acid.

FIG. 17A is a representative XRPD pattern of Form II of a crystalline salt of sulcardine and hydrochloric acid.

FIG. 19 is a representative XRPD pattern of a crystalline salt of sulcardine and ethane-1,2-disulfonic acid.

FIG. 37B is a representative FT-IR spectrum of Form II of monoedisylate salt of sulcardine.

DETAILED DESCRIPTION

Figure 1:
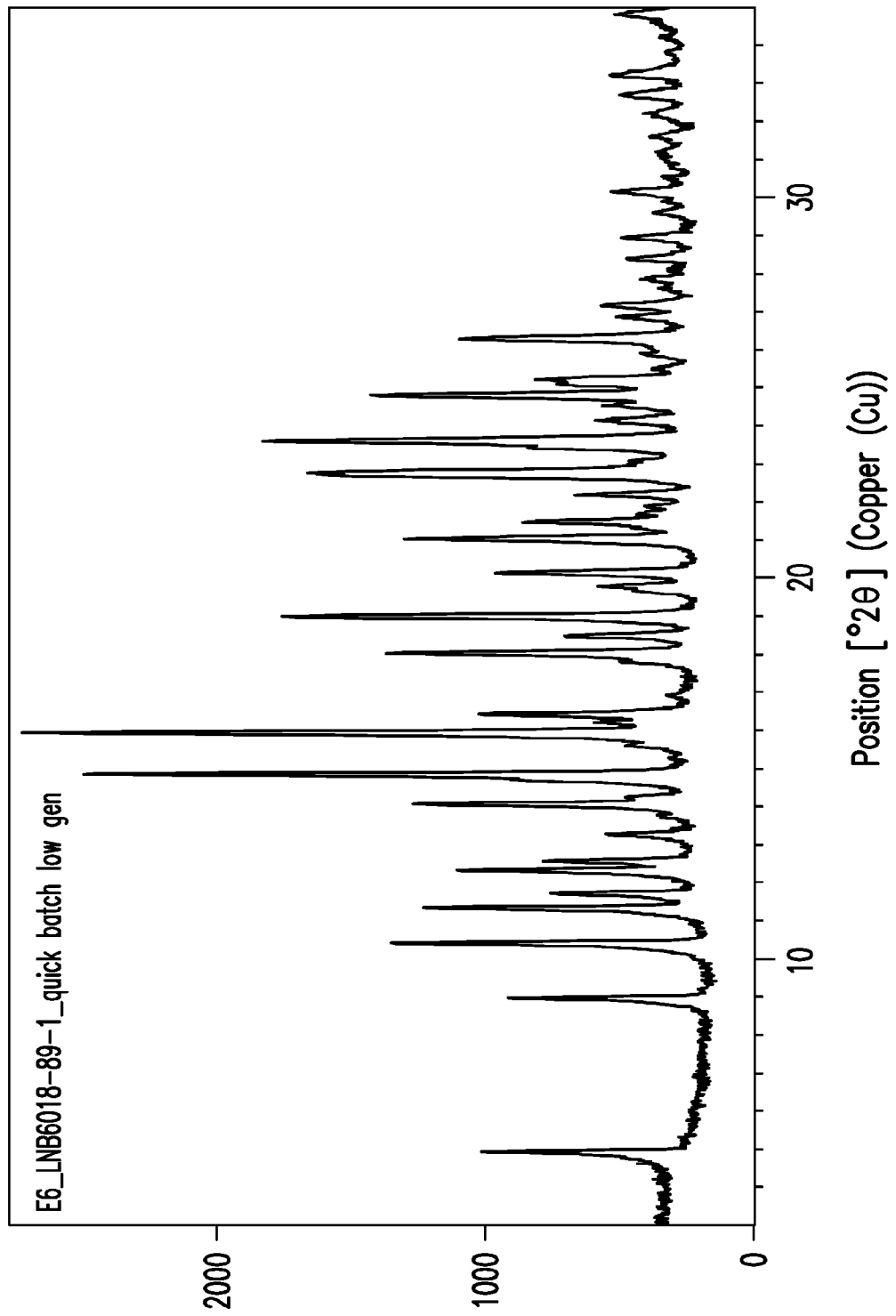
FIG. 1 is a representative XRPD pattern of a crystalline salt of sulcardine and naphthalene-1,5-disulfonic acid.

Sulcardine has a chemical name of 4-methoxy-N-(3,5-bis-(1-pyrrolidinylmethyl)-4-hydroxybenzyl)benzene sulfonamide (or N-(4-hydroxy-3,5-bis(pyrrolidin-1-ylmethyl)benzyl)-4-methoxybenzenesulfonamide), and has the following structure:

Sulcardine sulfate has the following structure:

Sulcardine sulfate can exist in a hydrated form. One such form is a trihydrate.

As used herein and unless otherwise specified, the term "crystal forms" and related terms refer to solid forms that are crystalline. In certain embodiments, a sample containing a sulcardine solid form, such as a crystal form, provided herein may be substantially free of other solid forms such as the amorphous form and/or other crystal forms. In certain embodiments, such a sample containing a crystal form of a sulcardine salt provided herein may contain less than about 1%, 2%, 3%, 4%, 5%, 6%, 7%, 8%, 9%, 10%, 15%, 20%, 25%, 30%, 35%, 40%, 45% or 50% of one or more other solid forms of sulcardine salts such as the amorphous form and/or other crystal forms of sulcardine salts on a weight basis. In certain embodiments, a crystal form of a sulcardine salt provided herein may be physically and/or chemically pure. In certain embodiments, a crystal form of a sulcardine salt provided herein may be about 99%, 98%, 97%, 96%, 95%, 94%, 93%, 92%, 91% or 90% physically and/or chemically pure.

As used herein and unless otherwise specified, the term "amorphous," "amorphous form," and related terms used herein, mean that the substance, component or product in question is not substantially crystalline as determined by X-ray diffraction. Such X-ray diffraction patterns often exhibit what is termed an "amorphous halo" as seen, for example, in FIG. 4.

In some embodiments, provided herein are salts formed by sulcardine free base and acids. These acids may be organic or inorganic acids. Some of the salts made by sulcardine and said acids are polymorphic. Various techniques may be used to show that a salt of sulcardine and an acid has been made. For example, a solid that may be a salt may be analyzed by x-ray powder diffraction and if the pattern differs from the x-ray powder diffraction of the component materials, then a new composition has been formed. Acid counterions shown below have pKa values of greater than 3 units from the strongest basic free base sulcardine pKa value. Table 1 shows the pKa of the free base sulcardine with respect to the salts identified in the disclosure.

TABLE 1

Counterion $pK_a$ Data

| Counterion (salt former) | $pK_a$ | | |
|---|---|---|---|
| | 1 | 2 | 3 |
| Sulcardine free base comparator | 6.00 | 10.57 | 11.65 |
| Hydrobromic acid | −9.00 | — | — |
| Hydrochloric acid | −6.10 | — | — |
| 1,5-Naphthalene-disulfonic acid | −3.37 | −2.64 | — |
| 1,2-Ethanedisulfonic acid | −2.06 | −1.50 | — |
| Naphthalene-2-sulfonic acid | 0.17 | — | — |
| 1-Hydroxy-2-naphthoic acid | 2.70 | 13.5 | — |

In each of the salt procedures, the free base of sulcardine was used to make the corresponding salts. The free base of sulcardine is amorphous and a representative pattern can be seen in FIG. 4. The x-ray powder diffraction patterns of the corresponding free acids have patterns that are crystalline and the XRPD patterns of the salts all differ from the sum of the corresponding free acids and the amorphous sulcardine. Thus, the solids reported herein are not physical mixtures of amorphous sulcardine and the corresponding acid. Indeed, the XRPD data and the pKa data indicate that the resulting solids are salts as further reported herein.

A screen was done to identify crystalline salts of sulcardine. Over 25 potential salt formers were analyzed in numerous solvents and solvent systems. In most cases, either no crystalline salts were formed, or the crystalline salts were unstable upon storage conditions such as at 40° C. and 75% RH. The salts created from salt formers in Table 1, by comparison, formed crystalline salts and were stable at 40° C. and 75% RH under the conditions provided herein. A "salt former" is a compound which may be used to create a salt with, for example, sulcardine. In many embodiments, the salt former is an acid. In addition to the salt screen, a polymorph screen was done on several of the salts identified.

For crystalline salts, a common technique to characterize such crystalline salts is x-ray powder diffraction ("XRPD"). An XRPD pattern is an x-y graph with 2Θ (diffraction angle) on the x-axis and intensity on the y-axis. The pattern contains peaks which may be used to characterize a salt or other solid forms. The peaks are usually represented and referred to by their position on the x-axis rather than the intensity of peaks on the y-axis because peak intensity can be particularly sensitive to sample orientation (see Pharmaceutical Analysis, Lee & Web, pp. 255-257 (2003)). Thus, intensity is not typically used by those skilled in the pharmaceutical arts to characterize crystalline salts or other solid forms.

An XRPD pattern output from a diffractometer may be used to characterize a crystalline salt. A smaller subset of such data, however, may also be, and typically is, suitable for characterizing a crystalline salt. For example, a collection of one or more peaks from such a pattern may be used to characterize a crystalline salt. Indeed, a single XRPD peak may be used to characterize a crystalline salt. When a crystalline salt herein is characterized by "one or more peaks" of an XRPD pattern and such peaks are listed, what is meant is that any combination of the peaks listed may be used to characterize the crystalline salt. Further, the fact that other peaks are present in the XRPD pattern, does not negate or otherwise limit the characterization.

Other data may also be used to characterize a crystalline salt alone or in combination with XRPD data. For example, melting point is often used to characterize crystalline salts. In some embodiments, differential thermal analysis (DTA) is used to identify the onset melting behavior of some crystalline salts. Such onsets may be characteristic of particular crystalline salts. In some cases, no melting was observed below the temperature at which decomposition occurs. In some embodiments, infrared spectral (IR) data may be used to characterize crystalline salts either alone or together with other solid-state data such as XRPD data.

As with any data measurement, there is variability in x-ray powder diffraction. In addition to the variability in peak intensity, there is also variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline material, prepared under different conditions may yield slightly different diffractograms. Factors such as particle size, moisture content, solvent content, and orientation may all affect how a sample diffracts x-rays. Another source of variability comes from instrument parameters. Different x-ray instruments operate using different parameters and these may lead to slightly different diffraction patterns from the same crystalline form. Likewise, different software packages process x-ray data differently and this also leads to variability. These and other sources of variability are known to those of ordinary skill in the pharmaceutical arts. Due to such sources of variability, it is common to recite x-ray diffraction peaks using the word "about" or "approximately" or other similar term prior to the peak value in °2Θ which presents the data to within 0.1 or 0.2°2Θ of the stated peak value depending on the circumstances. Unless specified otherwise, x-ray powder diffraction peaks provided herein are reported with a variability on the order of ±0.2 degree °2Θ and are intended to be reported with such a variability whether the word "about" or "approximately" or other similar term is present or not. Variability also exists in thermal measurements, such as DTA, and may also be indicative of sample purity. With respect to DTA, typical measurement variability is on the order of 1° C.

With respect to IR data, unless specified otherwise, IR peaks provided herein are reported with a variability on the order of 2 cm$^1$ and are intended to be reported with such a variability whether the word "about" or "approximately" or other similar term is present or not.

Characterization data that "matches" those of a reference solid form is understood by those skilled in the art to correspond to the same solid form as the reference solid form. In analyzing whether data "match," a person of ordinary skill in the art understands that particular characterization data points may vary to a reasonable extent while still describing a given solid form, due to, for example, experimental error and routine sample-to-sample analysis.

In various embodiments, salts of sulcardine and mononaphthalene salt formers are provided. A mononaphthalene former is one where the former contains as a substituent a single naphthalene moiety. In some of these embodiments, the mononaphthalene salt formers contain one or more sulfonic acid moieties, such as, for example, one, or two sulfonic acid moieties. When two sulfonic acid moieties are present, they may on the same ring or different rings of the naphthalene group.

The mononaphthalene salt former may be an organic acid such as a carboxylic acid, and the salt former may be further substituted, for example, on the naphthalene group. Example of substituents include a hydroxyl group. In some embodiments, when substituted with a hydroxyl group, the hydroxyl is ortho to the organic acid group.

In some embodiments, crystalline salts of sulcardine are provided. For example, crystalline salts of sulcardine with salt formers other than sulfuric acid are provided. In other embodiments, crystalline salts of sulcardine with organic sulfonic acids are provided. Such sulfonic acids may be aromatic or aliphatic and each may be substituted or unsubstituted. An example of a substituent is hydroxyl. In other embodiments, crystalline salts of inorganic acids other than sulfuric acid is provided. For example, the disclosure includes crystalline salts of sulcardine and halides.

In other embodiments, crystalline salts of sulcardine and aromatic carboxylic acids are provided. Examples of aromatic moieties include naphthyl moieties. The naphthyl moieties may be further substituted, such as with hydroxyl groups.

In some embodiments, provided herein is a solid form comprising an acid salt of sulcardine, wherein the acid is an acid that contains a single naphthalene moiety and one or more sulfonic or carboxylic acid moieties, a halide acid, or ethane-1,2-disulfonic acid.

In some embodiments, the acid is an acid that contains a single naphthalene moiety and one or more sulfonic or carboxylic acid moieties. In some embodiments, the acid contains a single naphthalene moiety and one or more (e.g., one or two) sulfonic acid moieties. In some embodiments, the acid contains a single naphthalene moiety and one or more (e.g., one or two) carboxylic acid moieties. In some embodiments, the naphthalene moiety is directly substituted with the sulfonic or carboxylic acid moieties. In some embodiments, the naphthalene moiety is further substituted. In some embodiments, the naphthalene moiety is further substituted with hydroxyl. In some embodiments, the acid is naphthalene-1,5-disulfonic acid. In some embodiments, the acid is 1-hydroxy-2-naphthoic acid. In some embodiments, the acid is naphthalene-2-sulfonic acid.

In some embodiments, the acid is an halide acid. In some embodiments, the acid is hydrochloric acid. In some embodiments, the acid is hydrobromic acid.

In some embodiments, the acid is ethane-1,2-disulfonic acid which is also referred to herein as 1,2-ethane disulfonic acid. When said acid is combined with sulcardine, it may be referred to as an edisylate salt, such as a monoedisylate salt or hemi-edisylate salt, of sulcardine.

1. Naphthalene-1,5-disulfonic Acid Salt of Sulcardine

In certain embodiments, provided herein is a naphthalene-1,5-disulfonic acid salt of sulcardine. In some embodiments, the salt is crystalline.

In some embodiments, the molar ratio of sulcardine to naphthalene-1,5-disulfonic acid in the salt is about 1:1. In some embodiments, the salt is a mono-naphthalene-1,5-disulfonic acid salt of sulcardine.

A representative XRPD pattern of a naphthalene-1,5-disulfonic acid salt of sulcardine is provided in FIG. 1.

In some embodiments, provided herein is a solid form comprising a naphthalene-1,5-disulfonic acid salt of sulcardine, characterized by 1, 2, 3, 4, 5, 6, 7, 8, 9, 10, 11, 12, 13, 14, 15, 16, 17, 18, 19, 20, or all of the peaks located at approximately the following positions: 4.9, 9.0, 10.4, 11.3, 11.7, 12.3, 12.6, 14.1, 14.9, 15.9, 16.4, 18.0, 18.5, 19.0, 20.1, 21.0, 21.5, 22.8, 23.6, 24.8, and 26.3° 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by all of the peaks.

In some embodiments, provided herein is a solid form comprising a naphthalene-1,5-disulfonic acid salt of sulcardine, characterized by an XRPD pattern comprising peaks at approximately 14.9, 15.9, and 23.6° 2θ. In some embodiments, the XRPD pattern further comprises peaks at approximately 4.9 and 10.4° 2θ. In some embodiments, the XRPD pattern further comprises peaks at approximately 11.3, 12.3, and 19.0° 2θ. In some embodiments, the XRPD pattern comprises peaks at approximately 4.9, 9.0, 10.4, 11.3, 11.7, 12.3, 14.1, 14.9, 15.9, 18.0, 19.0, 22.8, and 23.6° 2θ.

In some embodiments, provided herein is a solid form comprising a naphthalene-1,5-disulfonic acid salt of sulcardine, characterized by an XRPD pattern that matches the XRPD pattern presented in FIG. 1.

In some embodiments, the XRPD patterns are obtained using Cu Kα radiation.

Figure 2:
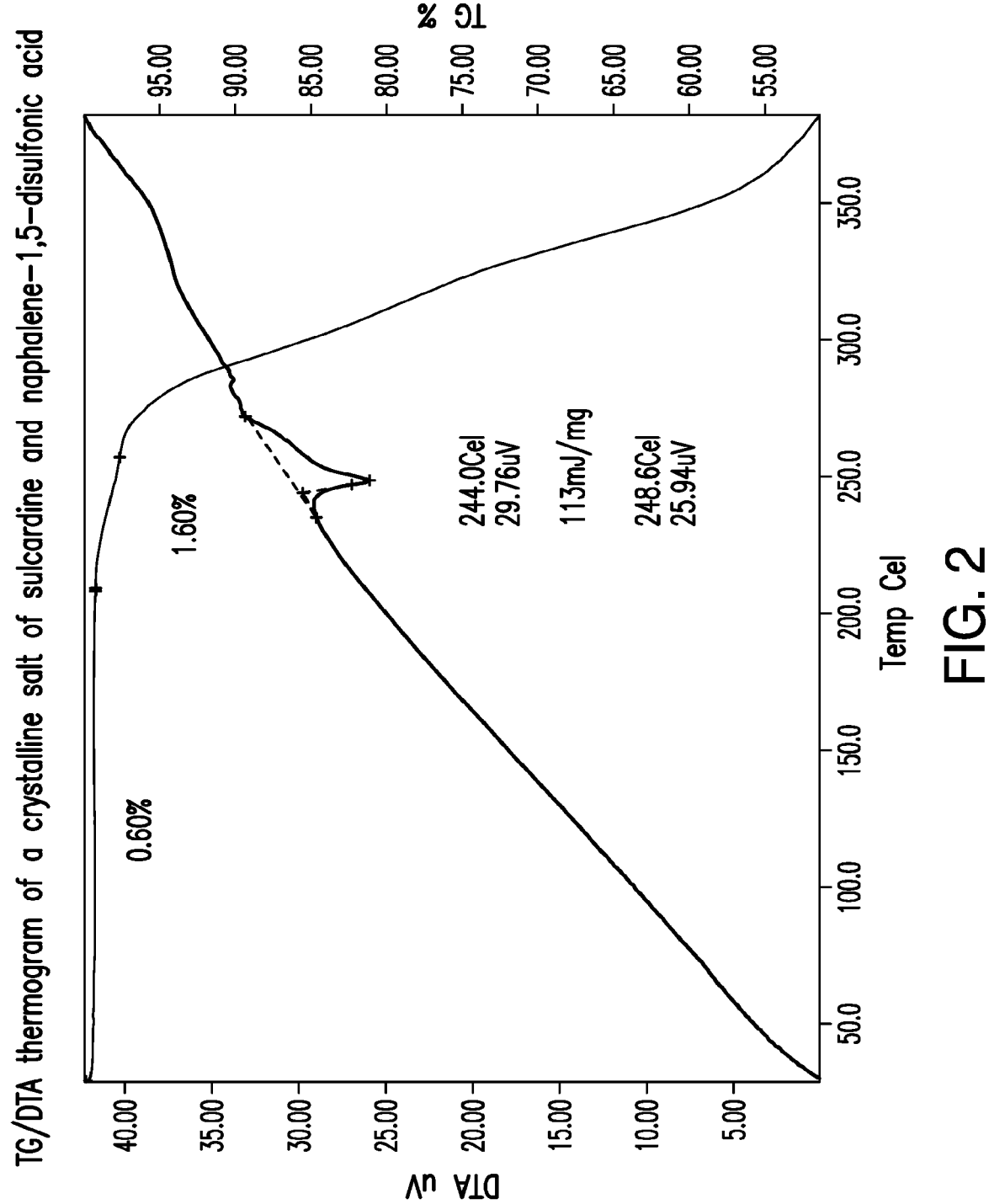
FIG. 2 is a representative TG/DTA thermogram of a crystalline salt of sulcardine and naphthalene-1,5-disulfonic acid.

Representative TG/DTA thermograms of a naphthalene-1,5-disulfonic acid salt of sulcardine are provided in FIG. 2. In some embodiments, provided herein is a solid form comprising a naphthalene-1,5-disulfonic acid salt of sulcardine, which exhibits a weight loss of about 0.6% upon heating from about 25° C. to about 200° C. In some embodiments, provided herein is a solid form comprising a naphthalene-1,5-disulfonic acid salt of sulcardine, characterized by a TG thermogram that matches the TG thermogram presented in FIG. 2.

In some embodiments, provided herein is a solid form comprising a naphthalene-1,5-disulfonic acid salt of sulcardine, which exhibits, as characterized by DTA, a thermal event with an onset temperature of about 244° C. In some embodiments, the thermal event also has a peak temperature of about 249° C. In some embodiments, without being limited by any particular theory, the thermal event corresponds to the melting of the solid form. In some embodiments, provided herein is a solid form comprising a naphthalene-1,5-disulfonic acid salt of sulcardine, characterized by a DTA thermogram that matches the DTA thermogram presented in FIG. 2.

In some embodiments, provided herein is a solid form comprising a naphthalene-1,5-disulfonic acid salt of sulcardine, which exhibits a mass increase of about 3.3% when subjected to an increase in a relative humidity (RH) from about 5% to about 95%.

In some embodiments, a naphthalene-1,5-disulfonic acid salt of sulcardine is prepared by subjecting a mixture of sulcardine and naphthalene-1,5-disulfonic acid (e.g., about 1:1 molar ratio) in a solvent (e.g., acetone) to a temperature cycle (e.g., between about 5° C. and about 25° C.) for a period of time (e.g., about 72 hours). In other embodiments, the temperature cycle is between ambient temperature and about 40° C.

In some embodiments, crystalline salts of sulcardine and naphthalene-1,5-disulfonic acid are provided. A preparation of a crystalline salt of sulcardine and naphthalene-1,5-disulfonic acid is set forth in Example 4 with a larger scale preparation set forth in Example 5. A crystalline salt of sulcardine and naphthalene-1,5-disulfonic acid may be characterized by an XRPD pattern comprising peak at about 4.9°2Θ. In addition, a crystalline salt of sulcardine and naphthalene-1,5-disulfonic acid may be characterized by an XRPD pattern comprising one or more peaks chosen from about 4.9°2Θ, about 10.4°2Θ, about 11.7°2Θ, about 12.3°2Θ, and about 15.9°2Θ. In addition, an XRPD pattern substantially the same as that of FIG. 1 (taken from Example 5) may be used to characterize a crystalline salt of sulcardine and naphthalene-1,5-disulfonic acid. A peak list corresponding to many of the peaks in FIG. 1 appears in Table 2.

TABLE 2

XRPD Peak Table Corresponding to FIG. 1

| Position (°2Θ) | d-spacing (Å) | Height (counts) | Relative Intensity (%) |
|---|---|---|---|
| 4.93 | 17.92 | 766.65 | 29.42 |
| 8.97 | 9.86 | 742.49 | 28.50 |
| 10.41 | 8.50 | 1199.68 | 46.04 |
| 11.34 | 7.80 | 1076.41 | 41.31 |
| 11.72 | 7.55 | 569.26 | 21.85 |
| 12.33 | 7.18 | 943.51 | 36.21 |
| 12.57 | 7.04 | 618.97 | 23.75 |
| 13.27 | 6.67 | 371.67 | 14.26 |
| 13.75 | 6.44 | 168.66 | 6.47 |
| 14.07 | 6.29 | 1114.30 | 42.76 |
| 14.24 | 6.22 | 310.84 | 11.93 |
| 14.85 | 5.96 | 2365.30 | 90.77 |
| 15.61 | 5.68 | 301.48 | 11.57 |
| 15.94 | 5.56 | 2605.69 | 100.00 |
| 16.21 | 5.47 | 419.81 | 16.11 |
| 16.43 | 5.40 | 861.99 | 33.08 |
| 16.92 | 5.24 | 148.02 | 5.68 |
| 17.81 | 4.98 | 333.96 | 12.82 |
| 18.03 | 4.92 | 1217.70 | 46.73 |
| 18.48 | 4.80 | 535.18 | 20.54 |
| 18.99 | 4.67 | 1613.33 | 61.92 |
| 19.79 | 4.49 | 377.24 | 14.48 |
| 20.14 | 4.41 | 805.76 | 30.92 |
| 21.04 | 4.22 | 1151.18 | 44.18 |
| 21.48 | 4.14 | 669.17 | 25.68 |
| 21.88 | 4.06 | 232.12 | 8.91 |
| 22.19 | 4.01 | 503.68 | 19.33 |
| 22.76 | 3.91 | 1515.94 | 58.18 |
| 23.41 | 3.80 | 676.80 | 25.97 |
| 23.60 | 3.77 | 1682.15 | 64.56 |
| 24.14 | 3.69 | 410.85 | 15.77 |
| 24.54 | 3.63 | 402.15 | 15.43 |
| 24.80 | 3.59 | 1250.18 | 47.98 |
| 25.10 | 3.55 | 568.12 | 21.80 |
| 25.22 | 3.53 | 650.94 | 24.98 |
| 25.51 | 3.49 | 205.46 | 7.89 |
| 25.88 | 3.44 | 239.93 | 9.21 |
| 26.28 | 3.39 | 933.43 | 35.82 |
| 26.85 | 3.32 | 335.28 | 12.87 |
| 27.16 | 3.28 | 380.80 | 14.61 |
| 27.86 | 3.20 | 230.45 | 8.84 |
| 28.39 | 3.14 | 285.83 | 10.97 |
| 28.93 | 3.09 | 327.73 | 12.58 |
| 29.61 | 3.02 | 189.91 | 7.29 |
| 30.15 | 2.96 | 350.83 | 13.46 |
| 31.17 | 2.87 | 174.26 | 6.69 |
| 31.60 | 2.83 | 207.20 | 7.95 |
| 32.20 | 2.78 | 223.79 | 8.59 |
| 32.69 | 2.74 | 305.52 | 11.73 |
| 33.21 | 2.70 | 362.52 | 13.91 |
| 33.80 | 2.65 | 150.63 | 5.78 |
| 34.20 | 2.62 | 157.52 | 6.05 |

Crystalline salts of many embodiments of sulcardine and naphthalene-1,5-disulfonic acid may be characterized by an onset melting point of about 244° C. (FIG. 2). The melting point may be used alone or in combination with XRPD data to characterize such crystalline salts of sulcardine and naphthalene-1,5-disulfonic acid. Thus, in some embodiments, crystalline salts of sulcardine and naphthalene-1,5-disulfonic acid may be characterized by an onset melting point of about 244° C. together with (a) an XRPD pattern comprising a peak at about 4.9°2Θ, or (b) an XRPD pattern comprising one or more peaks chosen from about 4.9°2Θ, about 10.4°2Θ, about 11.7°2Θ, about 12.3°2Θ, and about 15.9°2Θ; or (c) an XRPD pattern substantially the same as that of FIG. 1.

A dynamic vapor sorption ("DVS") experiment indicated that the salt prepared according to Example 5 had an uptake of about 3.3% water at 90% relative humidity ("RH"). The crystalline form of the salt before the DVS experiment and afterwards was the same, although at 60% RH it is possible there was a form change that, if occurred, reversed at the end of the DVS experiment. Under stability conditions of exposure for one week at 40° C. and 75% RH, the salt was unchanged by XRPD. It was also unchanged at 80° C. and ambient RH after one week and under ambient light conditions by XRPD, also after one week. HPLC measurements done after these stability experiments showed that under these conditions, the purity did not change (99% before the one-week stability studies and 99% afterwards). When exposed to ambient light, however, there was a reduction in crystallinity observed. Without being bound by theory, it is believed that the observed reduction in crystallinity was caused by insufficient sample in the XRPD plate of the XRPD instrument rather than a true loss of crystallinity in the sample.

For all of the stability studies provided herein under the condition of 40° C. and 75% RH, samples were in an uncapped vial and stored in a stability chamber set to 40° C./75% RH. For the 80° C. studies, samples were in a sealed vial and placed in an oven set to 80° C. For the ambient light studies, the samples were in a sealed vial placed on a windowsill in the lab which was exposed to ambient natural and artificial light.

The solubility of a crystalline salt of naphthalene-1,5-disulfonic acid of Example 5 is set forth in Table 3 below and was measured according to the procedures of Example 3. The table indicates the solubility is low for acidic pHs but increasing as pH becomes more basic than neutral.

TABLE 3

Solubility Data of the Crystalline Salt of Sulcardine and Naphthalene-1,5-Disulfonic Acid

| Buffer pH | pH after addition | pH after adjustment | Temperature (° C.) | pH after 72 hr | pH after adjustment | Temperature (° C.) | Solubility (mg·mL⁻¹) |
|---|---|---|---|---|---|---|---|
| 1.2 | 0.9 | 1.1 | 18.8 | 1.2 | N/A | 18.7 | 1.6 |
| 3.0 | 2.7 | 3.0 | 18.8 | 3.0 | N/A | 18.7 | 0.7 |
| 4.0 | 4.0 | N/A | 18.8 | 4.0 | N/A | 18.7 | 1.0 |
| 7.4 | 6.7 | 7.5 | 18.8 | 7.3 | N/A | 18.7 | 6.9 |

Figure 5:
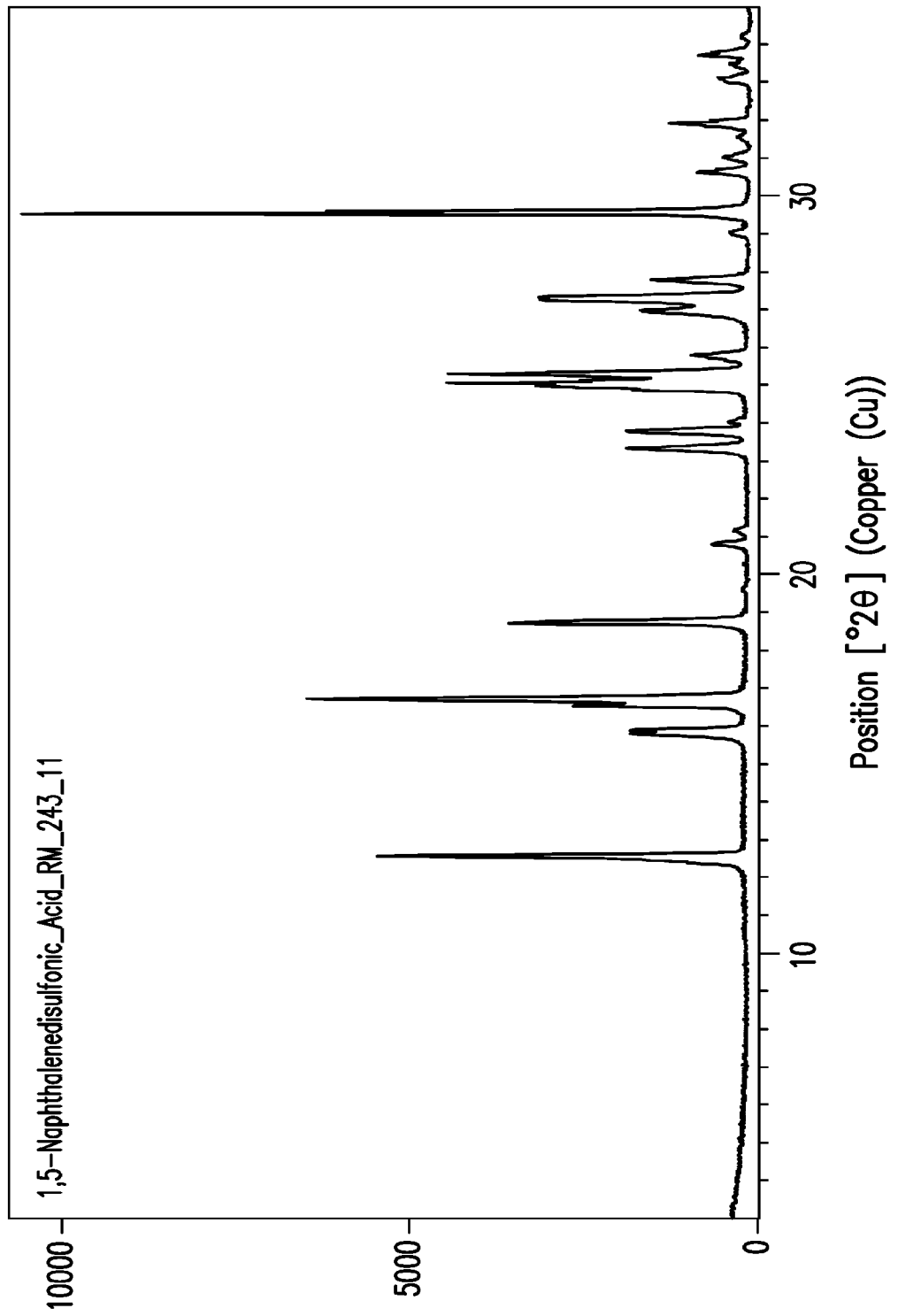
FIG. 5 is a representative XRPD pattern of naphthalene-1,5-disulfonic acid.

The XRPD patterns of the crystalline salt of sulcardine and naphthalene-1,5-disulfonic acid are not linear combinations of the XRPD patterns of the starting materials of sulcardine free base and naphthalene-1,5-disulfonic acid. For example, the peak at about 10.4°2Θ in the salt is not present in the XRPD pattern of naphthalene-1,5-disulfonic acid as seen in FIG. 5, and the sulcardine free base XRPD pattern of sulcardine does not have any peaks. Thus, the XRPD pattern of FIG. 1 is not a linear combination of the salt starting materials.

Further, a unique XRPD diffractogram and DTA melting event confirm that a new solid form has been produced. The H-NMR spectrum shows the stoichiometric presence of the counterion and possibly peak shifts compared with the free base, confirming that the material is a salt rather than a new polymorph or a solvate/hydrate of the individual components.

All of the combinations of the above embodiments are encompassed by this application.

2. Form I of 1-Hydroxy-2-Naphthoic Acid Salt of Sulcardine

In certain embodiments, provided herein is Form I of a 1-hydroxy-2-naphthoic acid salt of sulcardine. In some embodiments, the salt is crystalline.

In some embodiments, the molar ratio of sulcardine to 1-hydroxy-2-naphthoic acid in the salt is about 1:1. In some embodiments, the salt is a mono-1-hydroxy-2-naphthoic acid salt of sulcardine.

Figure 6:
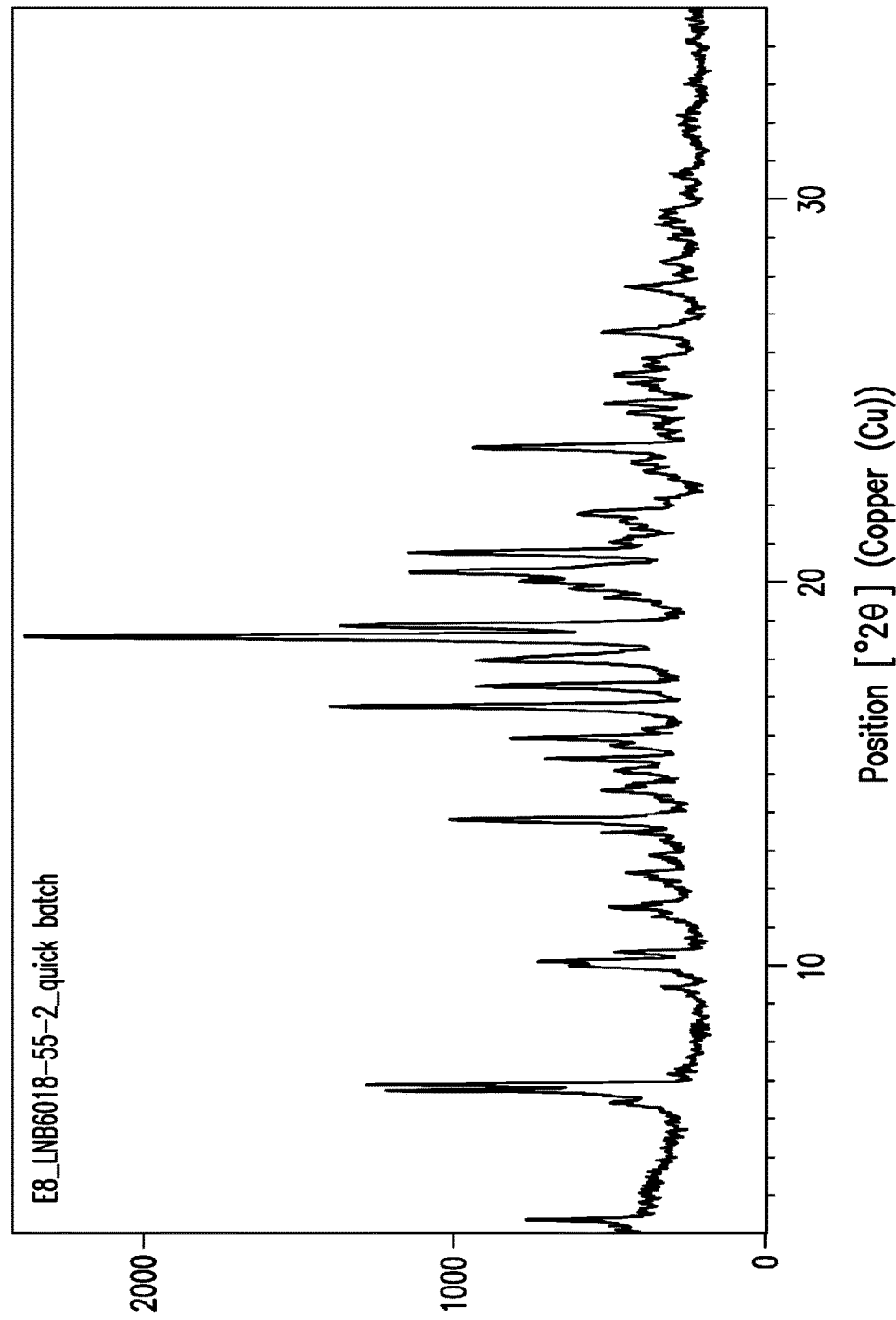
FIG. 6 is a representative XRPD pattern of Form I of a crystalline salt of sulcardine and 1-hydroxy-2-naphthoic acid.

A representative XRPD pattern of Form I of a 1-hydroxy-2-naphthoic acid salt of sulcardine is provided in FIG. 6.

In some embodiments, provided herein is a solid form comprising a 1-hydroxy-2-naphthoic acid salt of sulcardine, characterized by 1, 2, 3, 4, 5, 6, 7, 8, 9, 10, 11, 12, 13, 14, 15, 16, 17, 18, or all of the peaks located at approximately the following positions: 3.4, 6.7, 6.9, 10.0, 10.1, 13.8, 15.4, 15.9, 16.8, 17.3, 18.0, 18.6, 18.9, 19.8, 20.0, 20.3, 20.8, 21.8, and 23.5° 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by all of the peaks.

In some embodiments, provided herein is a solid form comprising a 1-hydroxy-2-naphthoic acid salt of sulcardine, characterized by an XRPD pattern comprising peaks at approximately 16.8, 18.6, and 18.9° 2θ. In some embodiments, the XRPD pattern further comprises peaks at approximately 6.7 and 6.9° 2θ. In some embodiments, the XRPD pattern further comprises peaks at approximately 13.8, 20.3, and 20.8° 2θ. In some embodiments, the XRPD pattern comprises peaks at approximately 3.4, 6.7, 6.9, 13.8, 15.4, 16.8, 17.3, 18.0, 18.6, 18.9, 20.3, 20.8, and 23.5° 2θ.

In some embodiments, provided herein is a solid form comprising a 1-hydroxy-2-naphthoic acid salt of sulcardine, characterized by an XRPD pattern comprising peaks at approximately 6.7, 6.9, and 16.8° 2θ. In some embodiments, the XRPD pattern further comprises a peak at approximately 18.9° 2θ.

In some embodiments, provided herein is a solid form comprising a 1-hydroxy-2-naphthoic acid salt of sulcardine, characterized by an XRPD pattern that matches the XRPD pattern presented in FIG. 6.

In some embodiments, the XRPD patterns are obtained using Cu Kα radiation.

Figure 7:
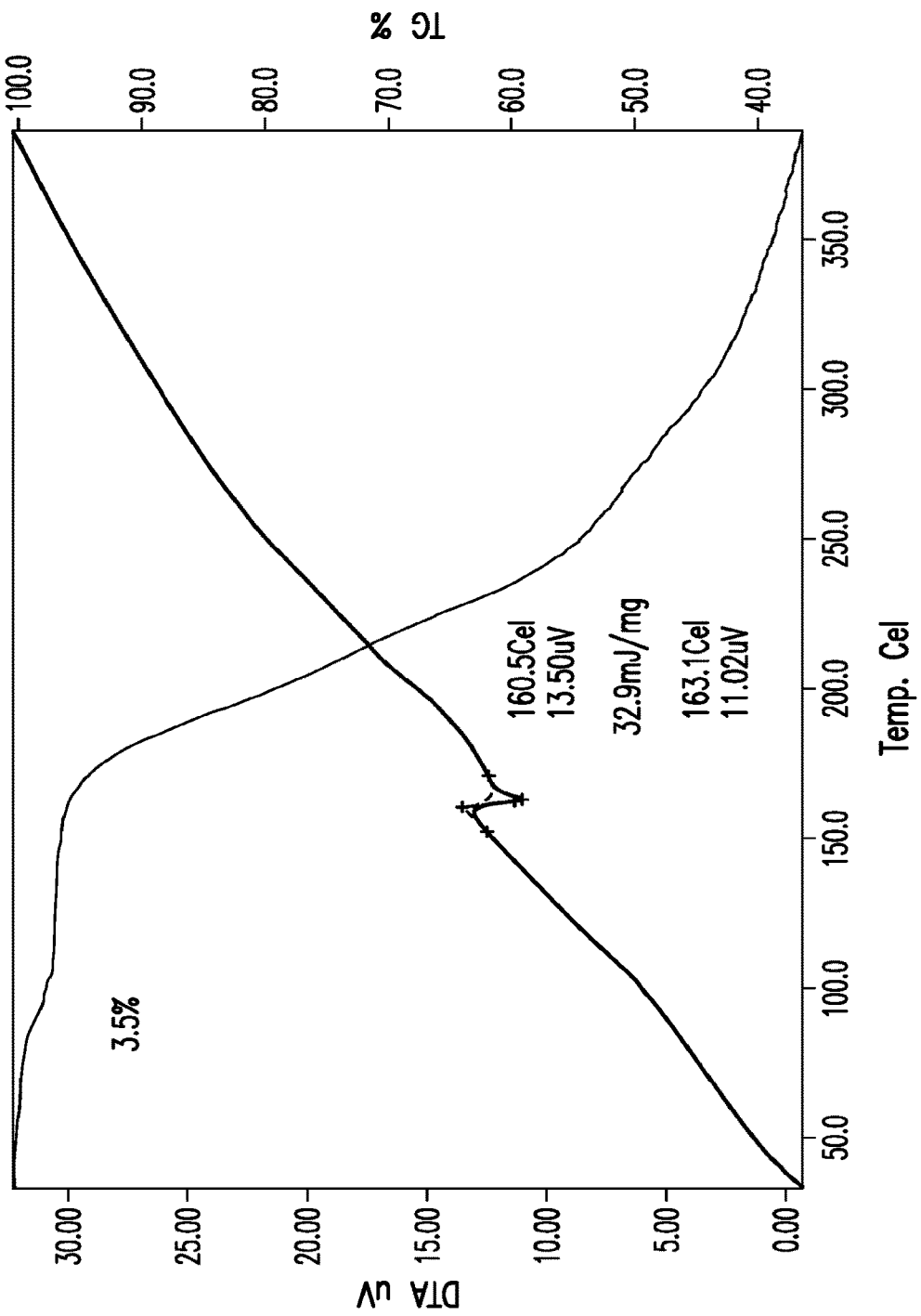
FIG. 7 is a representative TG/DTA thermogram of Form I of a crystalline salt of sulcardine and 1-hydroxy-2-naphthoic acid.

Representative TG/DTA thermograms of Form I of a 1-hydroxy-2-naphthoic acid salt of sulcardine are provided in FIG. 7. In some embodiments, provided herein is a solid form comprising a 1-hydroxy-2-naphthoic acid salt of sulcardine, which exhibits a weight loss of about 3.5% upon heating from about 25° C. to about 150° C. In some embodiments, provided herein is a solid form comprising a 1-hydroxy-2-naphthoic acid salt of sulcardine, characterized by a TG thermogram that matches the TG thermogram presented in FIG. 7.

In some embodiments, provided herein is a solid form comprising a 1-hydroxy-2-naphthoic acid salt of sulcardine, which exhibits, as characterized by DTA, a thermal event with an onset temperature of about 161° C. In some embodiments, the thermal event also has a peak temperature of about 163° C. In some embodiments, without being limited by any particular theory, the thermal event corresponds to the melting of the solid form. In some embodiments, provided herein is a solid form comprising a 1-hydroxy-2-naphthoic acid salt of sulcardine, characterized by a DTA thermogram that matches the DTA thermogram presented in FIG. 7.

In some embodiments, Form I of a 1-hydroxy-2-naphthoic acid salt of sulcardine is prepared by subjecting a mixture of sulcardine and 1-hydroxy-2-naphthoic acid (e.g., about 1:1 molar ratio) in a solvent (e.g., ethyl acetate) to a temperature cycle (e.g., between ambient temperature and about 40° C.) for a period of time (e.g., about 72 hours).

In some embodiments, crystalline salts of sulcardine and 1-hydroxy-2-naphthoic acid are provided. In some embodiments, Form I of a crystalline 1-hydroxy-2-naphthoic acid salt of sulcardine is provided. A preparation of Form I of a crystalline 1-hydroxy-2-naphthoic acid salt of sulcardine is described in Example 6. Form I of a crystalline 1-hydroxy-2-naphthoic acid salt of sulcardine may be characterized by an XRPD pattern comprising one or more x-ray powder diffraction peaks chosen from about 3.4°2Θ, about 6.7°2Θ, about 6.9°2Θ, and about 15.4°2Θ. In other embodiments Form I of a crystalline 1-hydroxy-2-naphthoic acid salt of sulcardine may be characterized by an XRPD pattern comprising peaks chosen from about 3.4°2Θ, about 6.7°2Θ, and about 6.9°2Θ. An XRPD pattern comprising a peak at about 3.4°2Θ and two peaks between about 6.5°2Θ and 7.12Θ may be used to characterize Form I of a crystalline 1-hydroxy-2-naphthoic acid salt of sulcardine. An XRPD pattern comprising a peak at about 3.4°2Θ may be used to characterize Form I of a crystalline 1-hydroxy-2-naphthoic acid salt of sulcardine because a peak at that angle is not present in Form II of a crystalline 1-hydroxy-2-naphthoic acid salt of sulcardine. Likewise, an XRPD pattern comprising any of the peaks at about 6.7°2Θ, about 6.9°2Θ, and about 15.4°2Θ may be used to characterize Form I of a crystalline 1-hydroxy-2-naphthoic acid salt of sulcardine. Form I of a crystalline 1-hydroxy-2-naphthoic acid salt of sulcardine may be characterized by an XRPD pattern substantially the same as that of FIG. 6. A peak list corresponding to many of the peaks in FIG. 6 appears in Table 4.

TABLE 4

XRPD Peak Table Corresponding to FIG. 6

| Position (°2θ) | d-spacing (Å) | Height (counts) | Relative Intensity (%) |
|---|---|---|---|
| 3.36 | 26.29 | 464.50 | 20.94 |
| 6.42 | 13.77 | 227.16 | 10.24 |
| 6.73 | 13.14 | 977.62 | 44.07 |
| 6.88 | 12.84 | 1060.72 | 47.81 |
| 9.41 | 9.40 | 112.14 | 5.05 |
| 9.98 | 8.87 | 426.64 | 19.23 |
| 10.10 | 8.76 | 533.04 | 24.03 |
| 10.35 | 8.55 | 281.88 | 12.71 |
| 11.29 | 7.84 | 143.63 | 6.47 |
| 11.50 | 7.69 | 290.19 | 13.08 |
| 11.63 | 7.61 | 186.21 | 8.39 |
| 12.41 | 7.13 | 234.66 | 10.58 |
| 12.86 | 6.88 | 165.59 | 7.46 |
| 13.47 | 6.57 | 327.00 | 14.74 |
| 13.80 | 6.42 | 821.94 | 37.05 |
| 14.56 | 6.08 | 322.08 | 14.52 |
| 15.08 | 5.88 | 271.87 | 12.25 |
| 15.39 | 5.76 | 512.30 | 23.09 |
| 15.73 | 5.63 | 284.21 | 12.81 |
| 15.93 | 5.56 | 614.51 | 27.70 |
| 16.14 | 5.49 | 176.24 | 7.94 |
| 16.75 | 5.29 | 1215.12 | 54.77 |
| 17.28 | 5.13 | 739.59 | 33.34 |
| 17.96 | 4.94 | 737.11 | 33.23 |
| 18.58 | 4.78 | 2218.51 | 100.00 |
| 18.86 | 4.71 | 1174.78 | 52.95 |
| 19.61 | 4.53 | 294.20 | 13.26 |
| 19.83 | 4.48 | 428.02 | 19.29 |
| 20.03 | 4.43 | 572.68 | 25.81 |
| 20.27 | 4.38 | 956.28 | 43.10 |
| 20.77 | 4.28 | 958.02 | 43.18 |
| 21.05 | 4.22 | 287.54 | 12.96 |
| 21.79 | 4.08 | 398.48 | 17.96 |
| 22.13 | 4.02 | 120.13 | 5.41 |
| 22.89 | 3.88 | 178.98 | 8.07 |
| 23.13 | 3.85 | 223.35 | 10.07 |
| 23.52 | 3.78 | 745.83 | 33.62 |
| 24.43 | 3.64 | 244.31 | 11.01 |
| 24.69 | 3.61 | 315.40 | 14.22 |
| 25.21 | 3.53 | 238.50 | 10.75 |
| 25.43 | 3.50 | 269.23 | 12.14 |
| 25.85 | 3.45 | 175.35 | 7.90 |
| 26.54 | 3.36 | 305.89 | 13.79 |
| 27.69 | 3.22 | 219.65 | 9.90 |
| 28.36 | 3.15 | 123.15 | 5.55 |
| 29.00 | 3.08 | 81.74 | 3.68 |
| 29.34 | 3.04 | 138.25 | 6.23 |
| 29.63 | 3.01 | 102.46 | 4.62 |
| 30.64 | 2.92 | 63.35 | 2.86 |
| 32.10 | 2.79 | 48.48 | 2.19 |
| 34.14 | 2.63 | 36.92 | 1.66 |

Form I of a crystalline salt of sulcardine and 1-hydroxy-2-naphthoic acid may be characterized by a nonset melting temperature of about 161° C. The melting point may be used alone or in combination with XR-PD data to characterize Form I of a crystalline salt of sulcardine and 1-hydroxy-2-naphthoic acid. Thus, Form I of a crystalline salt of sulcardine and 1-hydroxy-2-naphthoic may be characterized by an onset melting point of about 161° C. together with (a) an XR-PD pattern comprising one or more peaks chosen from 3.4°2Θ, about 6.7°2Θ, about 6.9°2Θ, and about 15.4°2Θ, or (b) an XR-PD pattern comprising one or more peaks chosen from about 3.4°2, about 6.7°2Θ, and about 6.9°2Θ; or (c) an XR-PD pattern comprising a peak at about 3.4°2Θ and two peaks between about 6.5°2Θ, and about 7.1°2θ; or (d) an XR-PD pattern substantially the same as that of FIG. 6.

All of the combinations of the above embodiments are encompassed by this application.

3. Form II of 1-Hydroxy-2-Naphthoic Acid Salt of Sulcardine

In certain embodiments, provided herein is Form II of a 1-hydroxy-2-naphthoic acid salt of sulcardine. In some embodiments, the salt is crystalline.

In some embodiments, the molar ratio of sulcardine to 1-hydroxy-2-naphthoic acid in the salt is about 1:1. In some embodiments, the salt is a mono-1-hydroxy-2-naphthoic acid salt of sulcardine.

Figure 9:
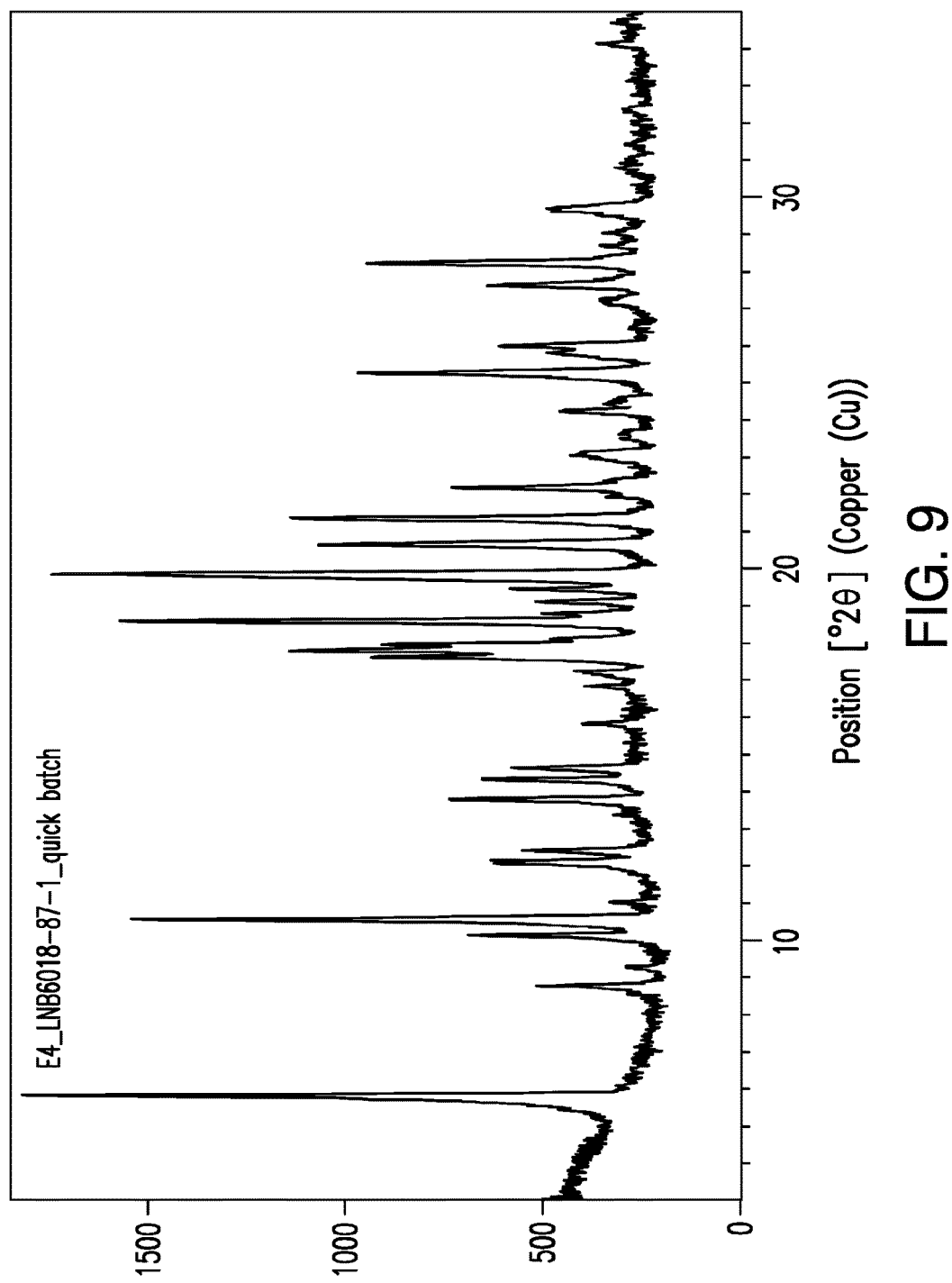
FIG. 9 is a representative XRPD pattern of Form II of a crystalline salt of sulcardine and 1-hydroxy-2-naphthoic acid.

A representative XRPD pattern of Form II of a 1-hydroxy-2-naphthoic acid salt of sulcardine is provided in FIG. 9.

In some embodiments, provided herein is a solid form comprising a 1-hydroxy-2-naphthoic acid salt of sulcardine, characterized by 1, 2, 3, 4, 5, 6, 7, 8, 9, 10, 11, 12, 13, 14, 15, 16, 17, 18, 19, 20, 21, or all of the peaks located at approximately the following positions: 5.8, 8.8, 10.1, 10.6, 12.1, 12.4, 13.8, 14.3, 14.6, 17.6, 17.8, 18.0, 18.6, 19.5, 19.9, 20.6, 21.4, 22.2, 25.3, 26.0, 27.6, and 28.2° 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by all of the peaks.

In some embodiments, provided herein is a solid form comprising a 1-hydroxy-2-naphthoic acid salt of sulcardine, characterized by an XRPD pattern comprising peaks at approximately 5.8, 18.6, and 19.9° 2θ. In some embodiments, the XRPD pattern further comprises peaks at approximately 10.6, 17.8, and 21.4° 2θ. In some embodiments, the XRPD pattern further comprises peaks at approximately 20.6 and 25.3° 2θ. In some embodiments, the XRPD pattern comprises peaks at approximately 5.8, 8.8, 10.6, 17.6, 17.8, 18.0, 18.6, 19.9, 20.6, 21.4, 25.3, and 28.2° 2θ.

In some embodiments, provided herein is a solid form comprising a 1-hydroxy-2-naphthoic acid salt of sulcardine, characterized by an XRPD pattern that matches the XRPD pattern presented in FIG. 9.

In some embodiments, the XRPD patterns are obtained using Cu Kα radiation.

Figure 10:
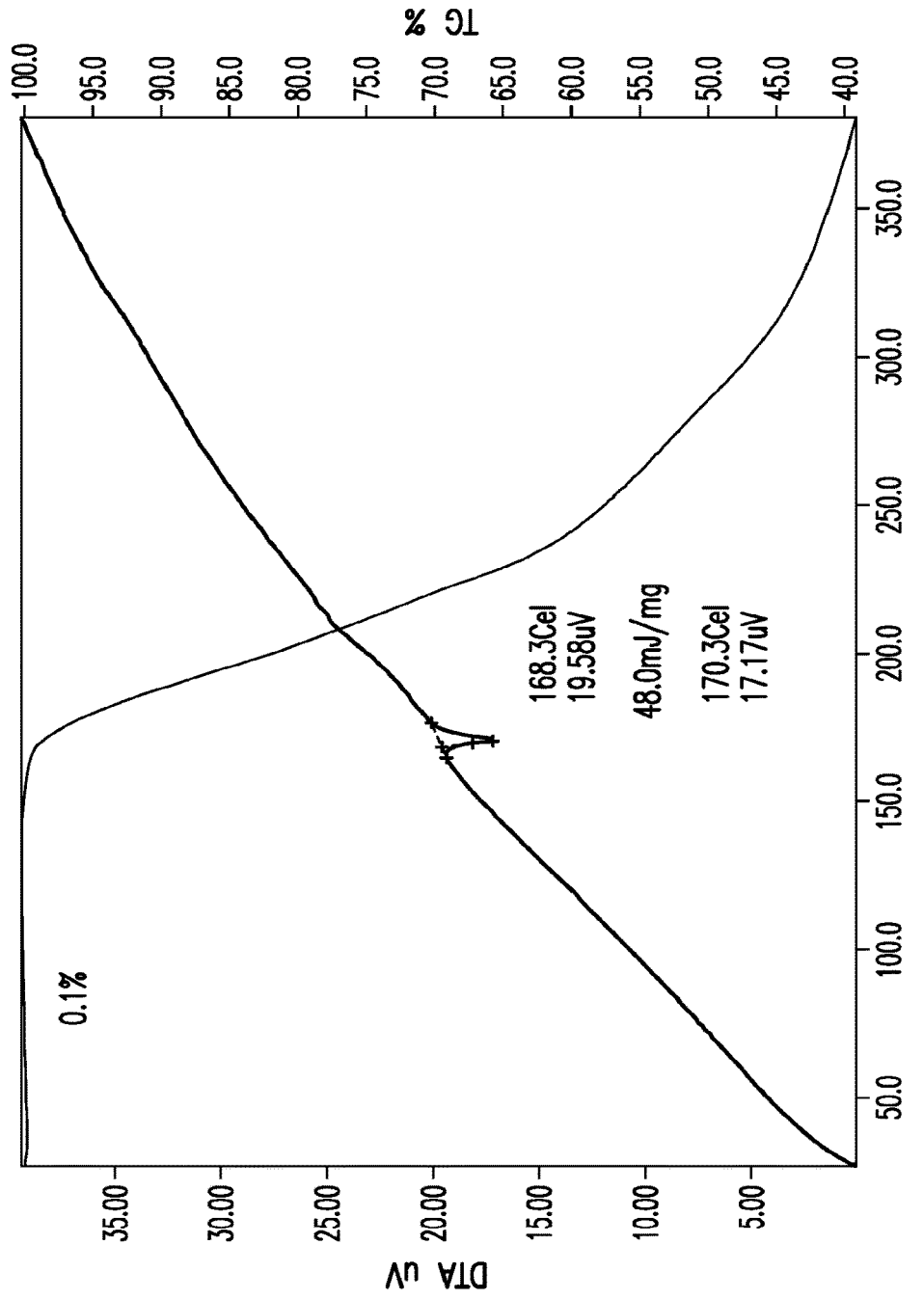
FIG. 10 is a representative TG/DTA thermogram of Form II of a crystalline salt of sulcardine and 1-hydroxy-2-naphthoic acid.

Representative TG/DTA thermograms of Form II of a 1-hydroxy-2-naphthoic acid salt of sulcardine are provided in FIG. 10. In some embodiments, provided herein is a solid form comprising a 1-hydroxy-2-naphthoic acid salt of sulcardine, which exhibits a weight loss of about 0.1% upon heating from about 25° C. to about 150° C. In some embodiments, provided herein is a solid form comprising a 1-hydroxy-2-naphthoic acid salt of sulcardine, characterized by a TG thermogram that matches the TG thermogram presented in FIG. 10.

In some embodiments, provided herein is a solid form comprising a 1-hydroxy-2-naphthoic acid salt of sulcardine, which exhibits, as characterized by DTA, a thermal event with an onset temperature of about 168° C. In some embodiments, the thermal event also has a peak temperature of about 170° C. In some embodiments, without being limited by any particular theory, the thermal event corresponds to the melting of the solid form. In some embodiments, provided herein is a solid form comprising a 1-hydroxy-2- naphthoic acid salt of sulcardine, characterized by a DTA thermogram that matches the DTA thermogram presented in FIG. 10.

In some embodiments, provided herein is a solid form comprising a 1-hydroxy-2-naphthoic acid salt of sulcardine, which exhibits a mass increase of about 0.7% when subjected to an increase in a relative humidity (RH) from about 10% to about 90%.

In some embodiments, Form II of a 1-hydroxy-2-naphthoic acid salt of sulcardine has approximate unit cell dimensions of: a=10.2 Å, b=29.9 Å, c=10.8 Å, α=90°, β=103.4°, and γ=90°. In some embodiments, Form II of a 1-hydroxy-2-naphthoic acid salt of sulcardine has approximately unit cell dimensions of: a=10.24 Å, b=29.92 Å, c=10.84 Å, α=90°, β=103.38°, and γ=90°. In some embodiments, Form II of a 1-hydroxy-2-naphthoic acid salt of sulcardine has approximately unit cell dimensions of: a=10.244 Å, b=29.917 Å, c=10.841 Å, α=90°, β=103.375°, and γ=90°. In some embodiments, Form II of a 1-hydroxy-2-naphthoic acid salt of sulcardine has approximately unit cell dimensions of: a=10.2443 Å, b=29.9171 Å, c=10.8406 Å, α=90°, β=103.375°, and γ=90°. In some embodiments, Form II of a 1-hydroxy-2-naphthoic acid salt of sulcardine has a unit cell of a space group of $P2_1/n$. In some embodiments, Form II of a 1-hydroxy-2-naphthoic acid salt of sulcardine has a volume of about 3232.31 Å$^3$/cell. In some embodiments, Form II of a 1-hydroxy-2-naphthoic acid salt of sulcardine has a Z value of 4. In some embodiments, Form II of a 1-hydroxy-2-naphthoic acid salt of sulcardine has a Z' value of 1.

In some embodiments, Form II of a 1-hydroxy-2-naphthoic acid salt of sulcardine is prepared by subjecting a mixture of sulcardine and 1-hydroxy-2-naphthoic acid (e.g., about 1:1 molar ratio) in a solvent (e.g., toluene) to a temperature cycle (e.g., between about 5° C. and about 25° C.) for a period of time (e.g., about 72 hours). In other embodiments, the temperature cycle is between ambient temperature and about 40° C.

In some embodiments, Form II of a crystalline salt of sulcardine and 1-hydroxy-2-naphthoic acid is provided. A preparation of Form II of a crystalline salt of sulcardine and 1-hydroxy-2-naphthoic acid is described in Example 7 and a scaled-up example in Example 8. Form II of a crystalline salt of sulcardine and 1-hydroxy-2-naphthoic acid may be characterized by an XRPD pattern comprising one or more peaks chosen from about 5.8°2Θ, and about 8.8°2Θ. None of these peaks are in Form I of a crystalline salt of sulcardine and 1-hydroxy-2-naphthoic acid. Form II may also be characterized by an XRPD pattern comprising peaks at about 5.8°2Θ and 8.8°2Θ. In addition, an XRPD pattern substantially the same as that of FIG. 9 may be used to characterize Form II of a crystalline salt of sulcardine and 1-hydroxy-2-naphthoic acid. A peak list corresponding to many of the peaks in FIG. 9 appears in Table 5.

TABLE 5

XRPD Peak Table Corresponding to FIG. 9

| Position (°2Θ) | d-spacing (Å) | Height (counts) | Relative Intensity (%) |
|---|---|---|---|
| 5.83 | 15.16 | 1547.63 | 98.74 |
| 8.77 | 10.08 | 313.32 | 19.99 |
| 9.26 | 9.55 | 73.46 | 4.69 |
| 10.13 | 8.73 | 489.19 | 31.21 |
| 10.56 | 8.38 | 1361.41 | 86.86 |
| 11.03 | 8.02 | 120.23 | 7.67 |
| 12.06 | 7.34 | 415.28 | 26.50 |
| 12.13 | 7.30 | 396.32 | 25.29 |
| 12.42 | 7.13 | 345.34 | 22.03 |
| 13.80 | 6.42 | 537.66 | 34.30 |
| 14.33 | 6.18 | 453.92 | 28.96 |
| 14.63 | 6.05 | 376.74 | 24.04 |
| 15.83 | 5.60 | 196.99 | 12.57 |
| 16.83 | 5.27 | 189.16 | 12.07 |
| 17.20 | 5.15 | 184.46 | 11.77 |
| 17.62 | 5.03 | 731.42 | 46.67 |
| 17.81 | 4.98 | 944.26 | 60.25 |
| 17.97 | 4.94 | 718.11 | 45.82 |
| 18.59 | 4.77 | 1391.57 | 88.79 |
| 18.80 | 4.72 | 301.13 | 19.21 |
| 19.12 | 4.64 | 316.24 | 20.18 |
| 19.45 | 4.56 | 381.14 | 24.32 |
| 19.86 | 4.47 | 1567.32 | 100.00 |
| 20.64 | 4.30 | 880.89 | 56.20 |
| 21.36 | 4.16 | 951.60 | 60.72 |
| 22.18 | 4.01 | 525.37 | 33.52 |
| 23.09 | 3.85 | 196.59 | 12.54 |
| 23.59 | 3.77 | 83.31 | 5.32 |
| 24.22 | 3.67 | 257.61 | 16.44 |
| 25.27 | 3.52 | 775.15 | 49.46 |
| 25.82 | 3.45 | 286.75 | 18.30 |
| 26.00 | 3.43 | 413.71 | 26.40 |
| 27.16 | 3.28 | 134.70 | 8.59 |
| 27.63 | 3.23 | 390.61 | 24.92 |
| 28.22 | 3.16 | 756.91 | 48.29 |
| 28.68 | 3.11 | 142.78 | 9.11 |
| 29.05 | 3.07 | 113.02 | 7.21 |
| 29.66 | 3.01 | 260.36 | 16.61 |
| 30.78 | 2.90 | 97.81 | 6.24 |
| 31.43 | 2.85 | 71.58 | 4.57 |
| 32.35 | 2.77 | 80.95 | 5.16 |
| 34.12 | 2.63 | 151.00 | 9.63 |

Form II may be characterized by an onset melting temperature of about 168° C. (FIG. 10). It may also be characterized by a melting onset temperature of about 168° C. together with (a) an XRPD pattern comprising one or more peaks chosen from about 5.8°2Θ and about 8.8°2Θ; or (b) an XRPD pattern substantially the same as that of FIG. 9.

A DVS experiment indicated that the salt prepared according to Example 9 had an uptake of about 0.7% water at 90% RH. The crystalline form of the salt before the DVS experiment and afterwards was the same. Under stability conditions of exposure for one week at 40° C. and 75% RH, the salt was unchanged by XRPD. It was also unchanged at 80° C. and ambient humidity after one week and under ambient light conditions by XRPD. HPLC measurements done after these stability experiments showed that under these conditions, the purity did not change (99% before the one-week stability studies and 99% afterwards).

Table 6 shows the solubility of Form II of a crystalline salt of sulcardine and 1-hydroxy-2-naphthoic acid. The solubility decreases from 16.8 mg/mL to 0.2 mg/mL as the pH increases from 1.2 to 7.4. However, at pH 1.2, the material loses crystallinity.

TABLE 6

Solubility Data of Form II of 1-hydroxy-2-naphthoic Acid Salt of Sulcardine

| Buffer pH | pH after addition | pH after adjustment | Temperature (° C.) | pH after 72 hr | pH after adjustment | Temperature (° C.) | Solubility (mg · mL$^{-1}$) |
|---|---|---|---|---|---|---|---|
| 1.2 | 1.9 | 1.2 | 18.8 | 3.4 | 1.2 | 18.5 | 16.8 |
| 3.0 | 4.3 | 3.0 | 18.8 | 4.0 | 2.9 | 18.5 | 4.2 |
| 4.0 | 4.4 | 4.0 | 18.8 | 4.5 | 4.1 | 18.5 | 6.1 |
| 7.4 | 7.3 | N/A | 18.8 | 7.0 | 7.5 | 18.5 | 0.2 |

Figure 12:
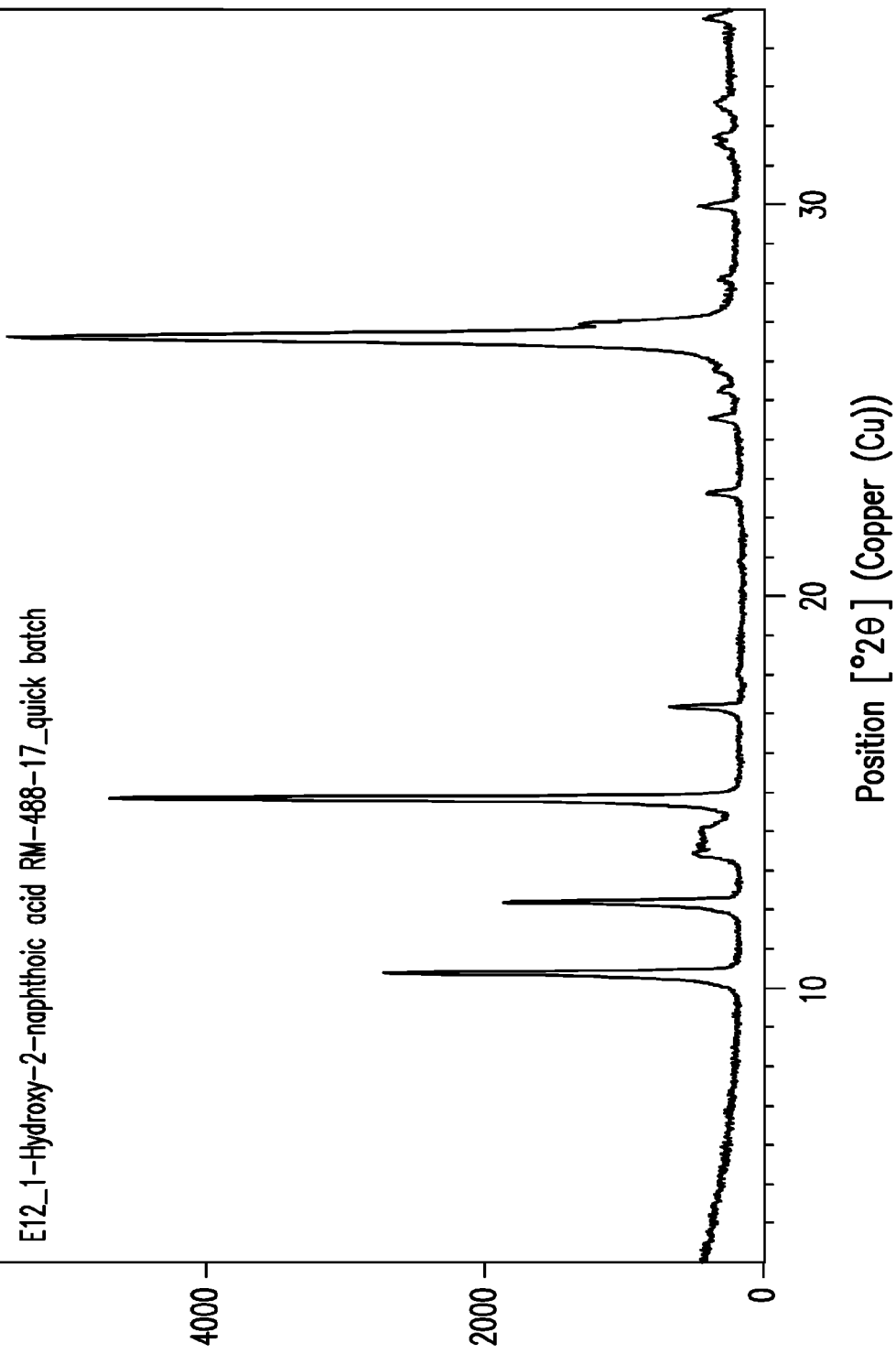
FIG. 12 is a representative XRPD pattern of 1-hydroxy-2-naphthoic acid.

The XRPD patterns of the different polymorphs of the crystalline salt of sulcardine and 1-hydroxy-2-naphthoic acid are not linear combinations of the XRPD patterns sulcardine free base and 1-hydroxy-2-naphthoic acid. For example, Form I has a peak at about 6.9°2Θ and Form II has a peak at about 8.8°2Θ. No such peaks are in the XRPD pattern of 1-hydroxy-2-naphthoic acid as seen in FIG. 12, and the free base XRPD pattern of sulcardine does not have any peaks. Thus, the XRPD patterns of FIG. 6 and FIG. 9 are not a linear combination of the salt starting materials.

Further, a unique XRPD diffractogram and DTA melting event confirm that a new solid form has been produced. The $^1$H-NMR spectrum shows the stoichiometric presence of the counterion and possibly peak shifts compared with the free base, confirming that the material is a salt rather than a new polymorph or a solvate/hydrate of the individual components.

All of the combinations of the above embodiments are encompassed by this application.

4. Naphthalene-2-Sulfonic Acid Salt of Sulcardine

In certain embodiments, provided herein is a naphthalene-2-sulfonic acid salt of sulcardine. In some embodiments, the salt is crystalline.

In some embodiments, the molar ratio of sulcardine to naphthalene-2-sulfonic acid in the salt is about 1:1. In some embodiments, the salt is a mono-naphthalene-2-sulfonic acid salt of sulcardine.

Figure 13:
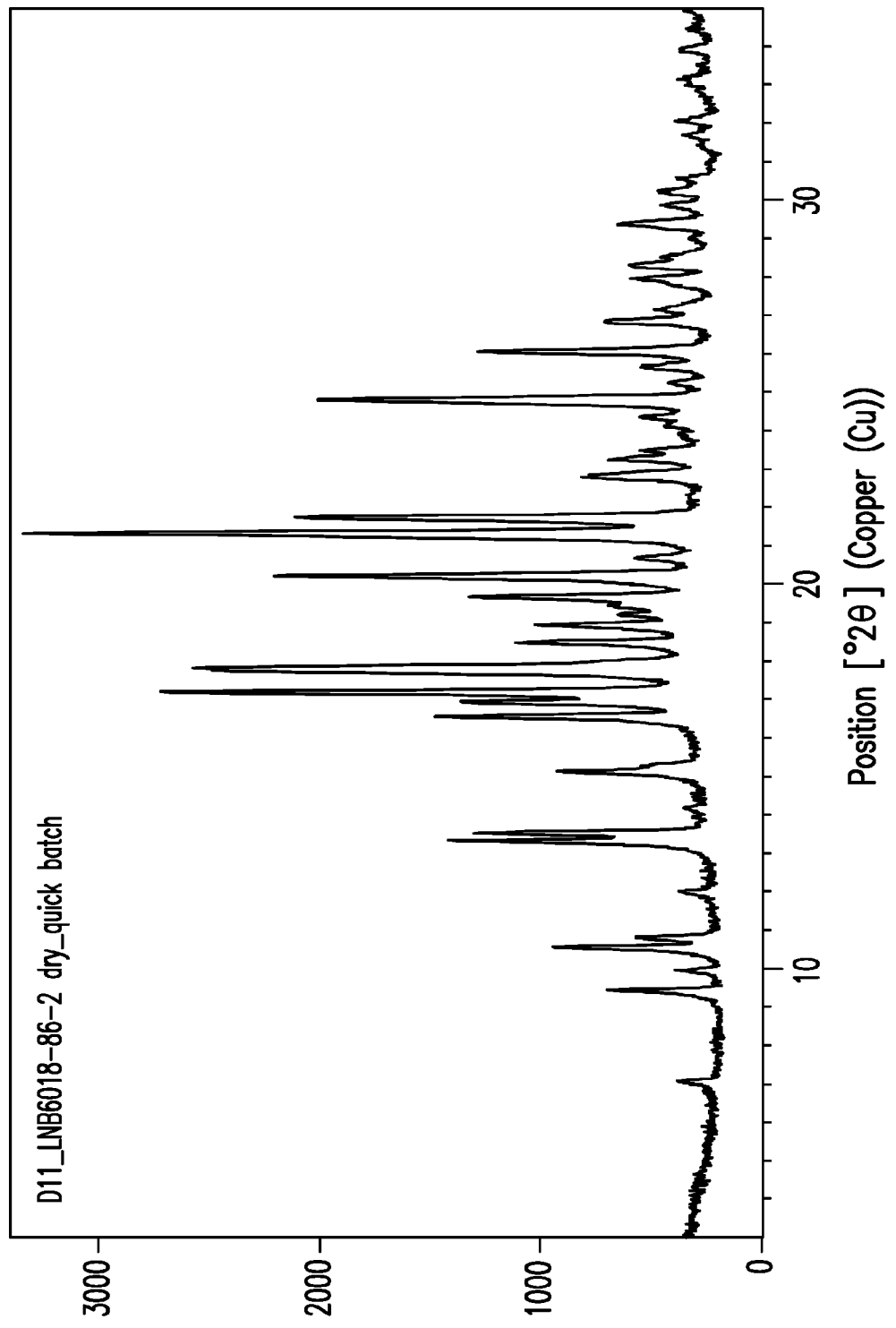
FIG. 13 is a representative XRPD pattern of a crystalline salt of sulcardine and naphthalene-2-sulfonic acid.

A representative XRPD pattern of a naphthalene-2-sulfonic acid salt of sulcardine is provided in FIG. 13.

In some embodiments, provided herein is a solid form comprising a naphthalene-2-sulfonic acid salt of sulcardine, characterized by 1, 2, 3, 4, 5, 6, 7, 8, 9, 10, 11, 12, 13, 14, 15, 16, 17, 18, 19, 20, 21, or all of the peaks located at approximately the following positions: 9.4, 10.6, 13.3, 13.5, 15.1, 16.6, 16.9, 17.2, 17.7, 17.8, 18.5, 18.9, 19.4, 19.7, 20.2, 21.3, 21.7, 22.8, 23.3, 24.8, 26.1, and 26.8° 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by all of the peaks.

In some embodiments, provided herein is a solid form comprising a naphthalene-2-sulfonic acid salt of sulcardine, characterized by an XRPD pattern comprising peaks at approximately 17.2, 17.8, and 21.3° 2θ. In some embodiments, the XRPD pattern further comprises peaks at approximately 13.3, 13.5, 16.6, and 16.9° 2θ. In some embodiments, the XRPD pattern further comprises peaks at approximately 9.4 and 10.6° 2θ. In some embodiments, the XRPD pattern comprises peaks at approximately 9.4, 10.6, 13.3, 13.5, 16.6, 16.9, 17.2, 17.7, 17.8, 19.7, 20.2, 21.3, and 24.8° 2θ.

In some embodiments, provided herein is a solid form comprising a naphthalene-2-sulfonic acid salt of sulcardine, characterized by an XRPD pattern that matches the XRPD pattern presented in FIG. 13.

In some embodiments, the XRPD patterns are obtained using Cu Kα radiation.

Figure 14:
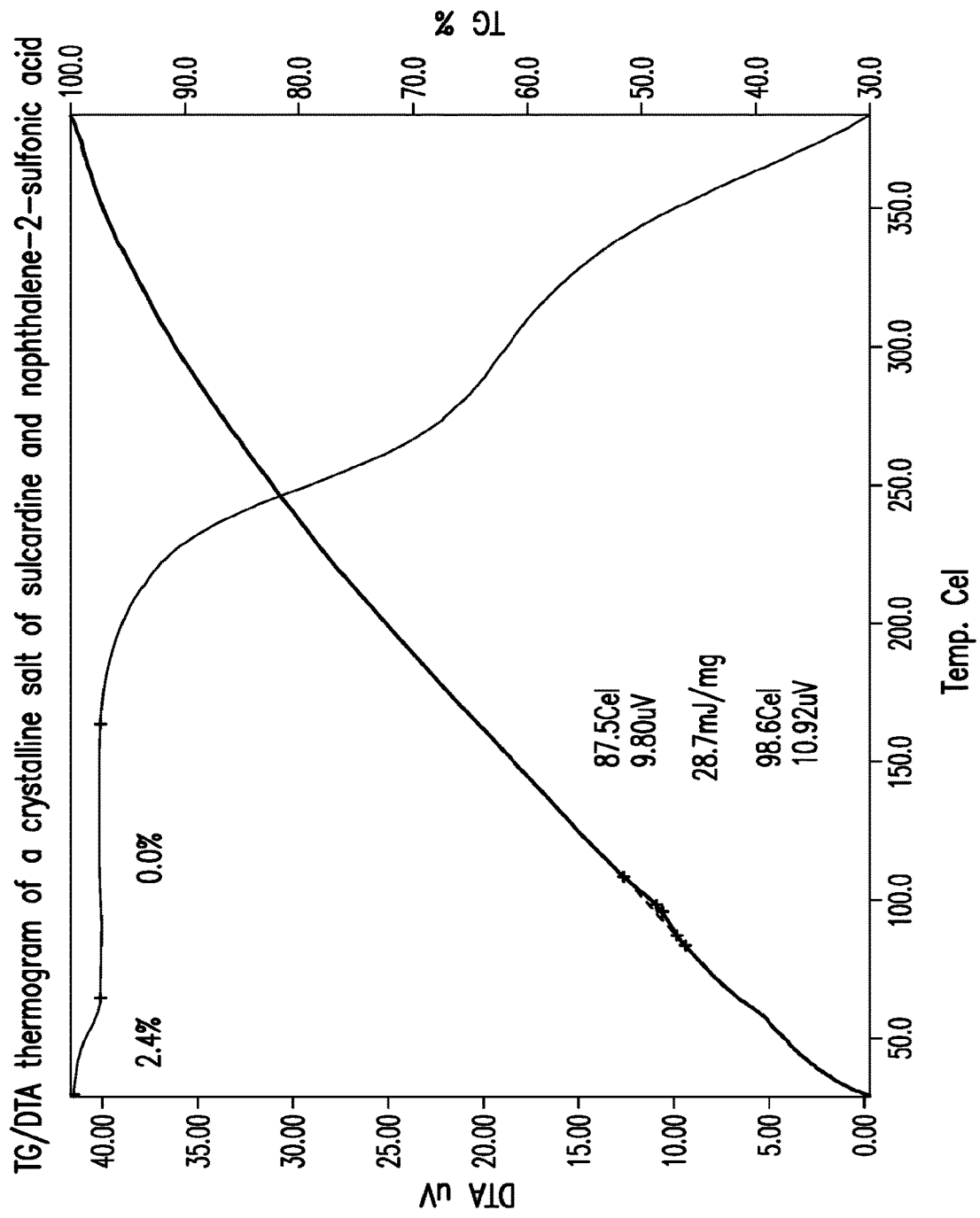
FIG. 14 is a representative TG/DTA thermogram of a crystalline salt of sulcardine and naphthalene-2-sulfonic acid.

Representative TG/DTA thermograms of a naphthalene-2-sulfonic acid salt of sulcardine are provided in FIG. 14. In some embodiments, provided herein is a solid form comprising a naphthalene-2-sulfonic acid salt of sulcardine, which exhibits a weight loss of about 2.4% upon heating from about 25° C. to about 60° C. In some embodiments, without being limited by a particular theory, the weight loss corresponds to the loss of water. In some embodiments, provided herein is a solid form comprising a naphthalene-2-sulfonic acid salt of sulcardine, characterized by a TG thermogram that matches the TG thermogram presented in FIG. 14.

In some embodiments, provided herein is a solid form comprising a naphthalene-2-sulfonic acid salt of sulcardine, which exhibits, as characterized by DTA, a thermal event with an onset temperature of about 88° C. In some embodiments, the thermal event also has a peak temperature of about 99° C. In some embodiments, without being limited by any particular theory, the thermal event corresponds to the melting of the solid form. In some embodiments, provided herein is a solid form comprising a naphthalene-2-sulfonic acid salt of sulcardine, characterized by a DTA thermogram that matches the DTA thermogram presented in FIG. 14.

In some embodiments, provided herein is a solid form comprising a naphthalene-2-sulfonic acid salt of sulcardine, which exhibits a mass increase of about 0.8% when subjected to an increase in a relative humidity (RH) from about 10% to about 90%.

In some embodiments, a naphthalene-2-sulfonic acid salt of sulcardine is prepared by subjecting a mixture of sulcardine and naphthalene-2-sulfonic acid (e.g., about 1:1 molar ratio) in a solvent (e.g., ethyl acetate) to a temperature cycle (e.g., between about 5° C. and about 25° C.) for a period of time (e.g., about 72 hours). In other embodiments, the temperature cycle is between ambient temperature and about 40° C.

In other embodiments, a crystalline salt of sulcardine and naphthalene-2-sulfonic acid is provided. A preparation of a crystalline salt of sulcardine and naphthalene-2-sulfonic acid is in Example 9 and a scaled-up preparation is in Example 10. The salt may be characterized by an XRPD pattern comprising one or more peaks chosen from about 9.4°2Θ, about 10.6°2Θ, about 13.3°2Θ, about 13.5°2Θ, about 16.6°2Θ, about 16.9°2Θ, and about 17.2°2Θ. It may also be characterized by an XRPD pattern comprising peaks chosen from about 9.4°2Θ, about 10.6°2Θ, and about 13.5°2Θ. In addition, it may be further characterized by an XRPD pattern comprising two peaks between about 13.1°2Θ and about 13.7°2Θ and three peaks between about 16.4°2Θ and about 17.4°2Θ. FIG. 13 may be used to characterize a crystalline salt of sulcardine and naphthalene-2-sulfonic acid. A peak list corresponding to many of the peaks in FIG. 13 appears in Table 7.

TABLE 7

XRPD Peak Table Corresponding to FIG. 13

| Position (°2Θ) | d-spacing (Å) | Height (counts) | Relative Intensity (%) |
|---|---|---|---|
| 7.07 | 12.51 | 176.92 | 5.50 |
| 9.44 | 9.37 | 513.36 | 15.97 |
| 9.95 | 8.89 | 203.06 | 6.32 |
| 10.56 | 8.38 | 770.75 | 23.97 |
| 10.80 | 8.19 | 360.51 | 11.21 |
| 12.00 | 7.38 | 184.87 | 5.75 |
| 13.33 | 6.64 | 1251.95 | 38.94 |
| 13.53 | 6.54 | 1121.64 | 34.89 |
| 15.12 | 5.86 | 726.20 | 22.59 |
| 15.31 | 5.79 | 301.11 | 9.37 |
| 16.56 | 5.35 | 1319.79 | 41.05 |
| 16.93 | 5.24 | 1180.83 | 36.73 |
| 17.20 | 5.16 | 2563.87 | 79.74 |
| 17.73 | 5.00 | 2168.94 | 67.46 |
| 17.82 | 4.98 | 2436.85 | 75.79 |
| 18.48 | 4.80 | 919.83 | 28.61 |
| 18.94 | 4.69 | 859.61 | 26.74 |
| 19.21 | 4.62 | 468.99 | 14.59 |
| 19.44 | 4.57 | 513.25 | 15.96 |
| 19.67 | 4.51 | 1153.36 | 35.87 |
| 20.22 | 4.39 | 2058.50 | 64.02 |
| 20.68 | 4.29 | 384.80 | 11.97 |
| 21.32 | 4.17 | 3215.20 | 100.00 |
| 21.74 | 4.09 | 1959.27 | 60.94 |
| 22.81 | 3.90 | 604.94 | 18.82 |
| 23.25 | 3.83 | 506.64 | 15.76 |
| 23.48 | 3.79 | 363.82 | 11.32 |
| 24.13 | 3.69 | 241.26 | 7.50 |
| 24.34 | 3.66 | 359.42 | 11.18 |
| 24.80 | 3.59 | 1855.36 | 57.71 |
| 25.23 | 3.53 | 221.07 | 6.88 |
| 25.66 | 3.47 | 352.91 | 10.98 |
| 26.05 | 3.42 | 1106.51 | 34.41 |
| 26.83 | 3.32 | 517.54 | 16.10 |
| 27.15 | 3.29 | 284.31 | 8.84 |
| 27.95 | 3.19 | 386.04 | 12.01 |
| 28.29 | 3.15 | 407.40 | 12.67 |
| 28.52 | 3.13 | 261.41 | 8.13 |
| 29.37 | 3.04 | 453.36 | 14.10 |
| 29.86 | 2.99 | 269.86 | 8.39 |
| 30.21 | 2.96 | 255.66 | 7.95 |
| 30.54 | 2.93 | 174.06 | 5.41 |
| 31.68 | 2.82 | 155.01 | 4.82 |
| 32.06 | 2.79 | 183.12 | 5.70 |
| 33.14 | 2.70 | 175.15 | 5.45 |
| 33.91 | 2.64 | 178.67 | 5.56 |
| 34.48 | 2.60 | 115.50 | 3.59 |

A crystalline salt of sulcardine and naphthalene-2-sulfonic acid may be characterized by an onset melting temperature of about 88° C. (FIG. 14). It may also be characterized by an onset melting temperature of about 88° C. together with (a) an XRPD pattern comprising one or more peaks chosen from about 9.4°2Θ, about 10.6°2Θ, about 13.3°2Θ, about 13.5°2, about 16.6°2, about 16.9°2Θ, and about 17.2°2Θ; (b) an XRPD pattern comprising peaks chosen from about 9.4° 2Θ, about 10.6°2Θ, and about 13.5°2Θ; (c) an XRPD pattern comprising two peaks between about 13.1°2Θ and about 13.7°2Θ and three peaks between about 16.4°2Θ and about 17.4°2Θ; or (d) an XRPD pattern substantially the same as that of FIG. 13.

In the TG/DTA experiment of FIG. 14, a weight loss of 2.4% was observed which corresponds to about 0.91 equivalents of water. This is consistent with a hydrate. Thus, the crystalline salt prepared in accordance with Example 10, for instance, produces a hydrate of a crystalline salt of sulcardine and naphthalene-2-sulfonic acid.

A DVS experiment indicated that the salt prepared according to Example 10 had an uptake of about 0.8% water between 10 and 90% RH, and that below 10% RH, the material appears to dehydrate. The crystalline form of the salt before the DVS experiment and afterwards was the same. Under stability conditions of exposure for one week at 40° C. and 75% RH, the salt was unchanged by XRPD. After 80° C. and ambient humidity after one week, the salt had changed into an orange gel, and under ambient light conditions after one week, the material was unchanged by XRPD but had turned pale yellow. IPLC measurements done after these stability experiments showed that the purity had dropped from 99% to 98% after one week at 40° C. and 75% RH, to 90% after one week at 80° C., and to 97% after one week under ambient light conditions.

Figure 16:
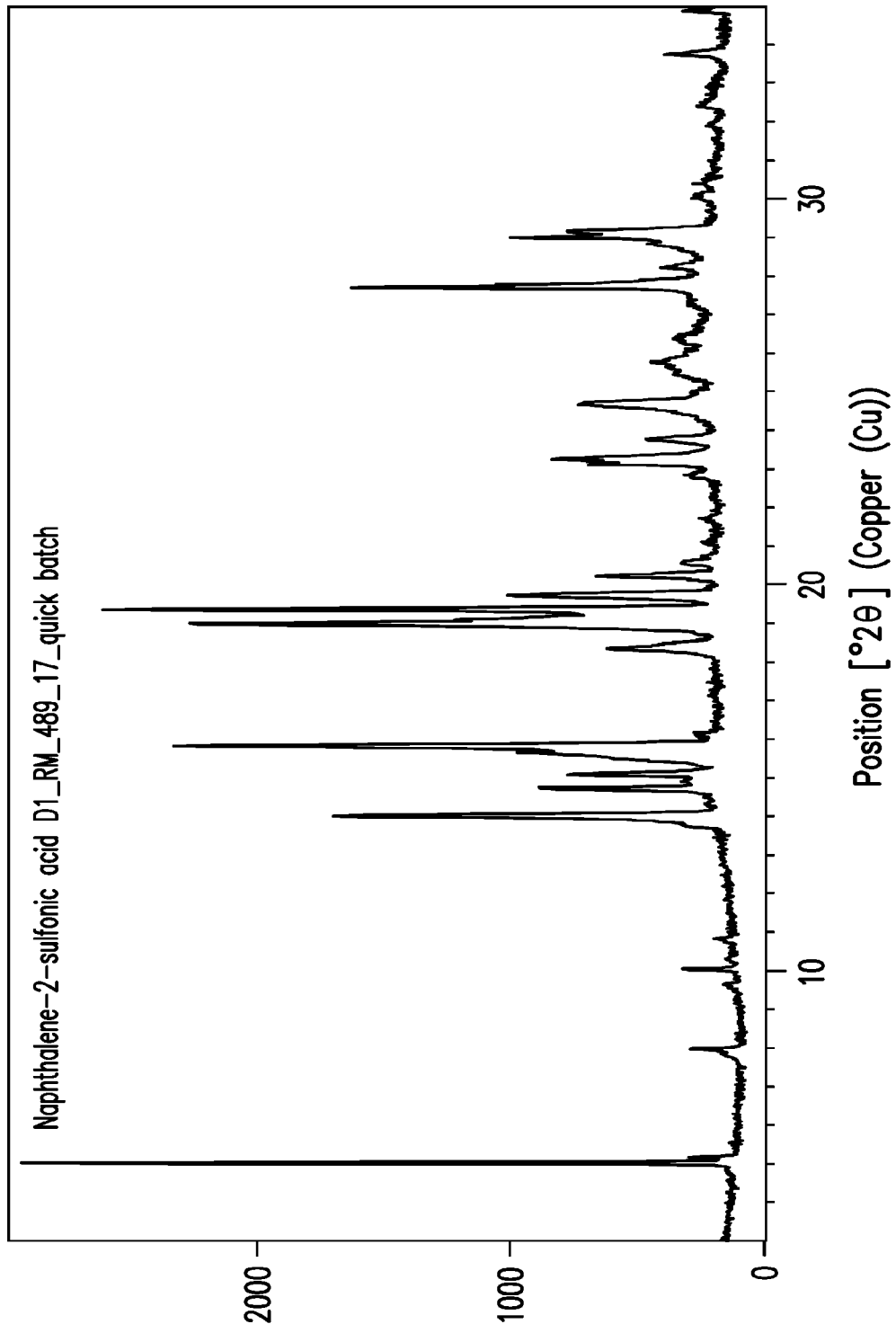
FIG. 16 is a representative XRPD pattern of naphthalene-2-sulfonic acid.

The XRPD pattern of crystalline salt of sulcardine and naphthalene-2-sulfonic acid is not linear combinations of the XRPD patterns of sulcardine free base and naphthalene-2-sulfonic acid. For example, naphthalene-2-sulfonic acid has a peak at about 5°2Θ as seen in FIG. 16. No such peak is present in the FIG. 13, and the free base XRPD pattern of sulcardine does not have any peaks. Thus, the XRPD pattern of FIG. 13 is not a linear combination of the salt starting materials.

Further, a unique XRPD diffractogram and DTA melting event confirm that a new solid form has been produced. The $^1$H-NMR spectrum shows the stoichiometric presence of the counterion and possibly peak shifts compared with the free base, confirming that the material is a salt rather than a new polymorph or a solvate/hydrate of the individual components.

The solubility of the salt of sulcardine and naphthalene-2-sulfonic acid is set forth in Table 8 below and was prepared according to the procedures of Example 3.

TABLE 8

Solubility Data of the Salt of Sulcardine and Naphthalene-2-Sulfonic Acid

| Buffer pH | pH after addition | pH after adjustment | Temperature (° C.) | pH after 72 hr | pH after adjustment | Temperature (° C.) | Solubility (mg · mL$^{-1}$) |
|---|---|---|---|---|---|---|---|
| 1.2 | 1.2 | N/A | 18.7 | 4.8 | 1.3 | 18.7 | 23.6 |
| 3.0 | 5.4 | 3.0 | 18.7 | 6.0 | 3.0 | 18.5 | 10.3 |
| 4.0 | 4.7 | 4.0 | 18.7 | 4.7 | 3.9 | 18.5 | 18.9 |
| 7.4 | 7.9 | 7.5 | 18.7 | 8.0 | 7.4 | 18.5 | 5.9 |

All of the combinations of the above embodiments are encompassed by this application.

5. Form I of Sulcardine Hydrochloride Salt

In certain embodiments, provided herein is Form I of a sulcardine hydrochloride salt. In some embodiments, the salt is crystalline.

In some embodiments, the molar ratio of sulcardine to hydrochloric acid in the salt is about 1:1. In some embodiments, the salt is a mono-hydrochloride salt of sulcardine.

A representative XRPD pattern of Form I of a sulcardine hydrochloride salt is provided in FIG. 17.

In some embodiments, provided herein is a solid form comprising a sulcardine hydrochloride salt, characterized by 1, 2, 3, 4, 5, 6, 7, 8, 9, 10, 11, 12, 13, 14, 15, 16, 17, 18, 19, 20, 21, 22, or all of the peaks located at approximately the following positions: 11.4, 11.5, 12.3, 13.0, 13.9, 14.8, 16.1, 17.2, 17.4, 17.8, 18.1, 18.6, 19.2, 19.8, 20.0, 20.3, 21.9, 23.6, 23.9, 25.4, 25.5, 27.4 and 28.4° 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by all of the peaks.

In some embodiments, provided herein is a solid form comprising a sulcardine hydrochloride salt, characterized by an XRPD pattern comprising peaks at approximately 17.4, 17.8, and 23.9° 2θ. In some embodiments, the XRPD pattern further comprises peaks at approximately 13.9, 20.3, and 21.9° 2θ. In some embodiments, the XRPD pattern further comprises peaks at approximately 17.2 and 18.6° 2θ. In some embodiments, the XRPD pattern comprises peaks at approximately 11.4, 12.3, 13.0, 13.9, 17.2, 17.4, 17.8, 18.1, 18.6, 19.8, 20.3, 21.9, and 23.9° 2θ.

In some embodiments, provided herein is a solid form comprising a sulcardine hydrochloride salt, characterized by an XRPD pattern comprising peaks at approximately 12.3, 13.0, and 17.8° 2θ. In some embodiments, the XRPD pattern further comprises peaks at approximately 13.9, 17.4, and 23.9° 2θ. In some embodiments, the XRPD pattern further comprises peaks at approximately 20.3 and 21.9° 2θ.

In some embodiments, provided herein is a solid form comprising a sulcardine hydrochloride salt, characterized by an XRPD pattern that matches the XRPD pattern presented in FIG. 17.

In some embodiments, the XRPD patterns are obtained using Cu Kα radiation.

Figure 18:
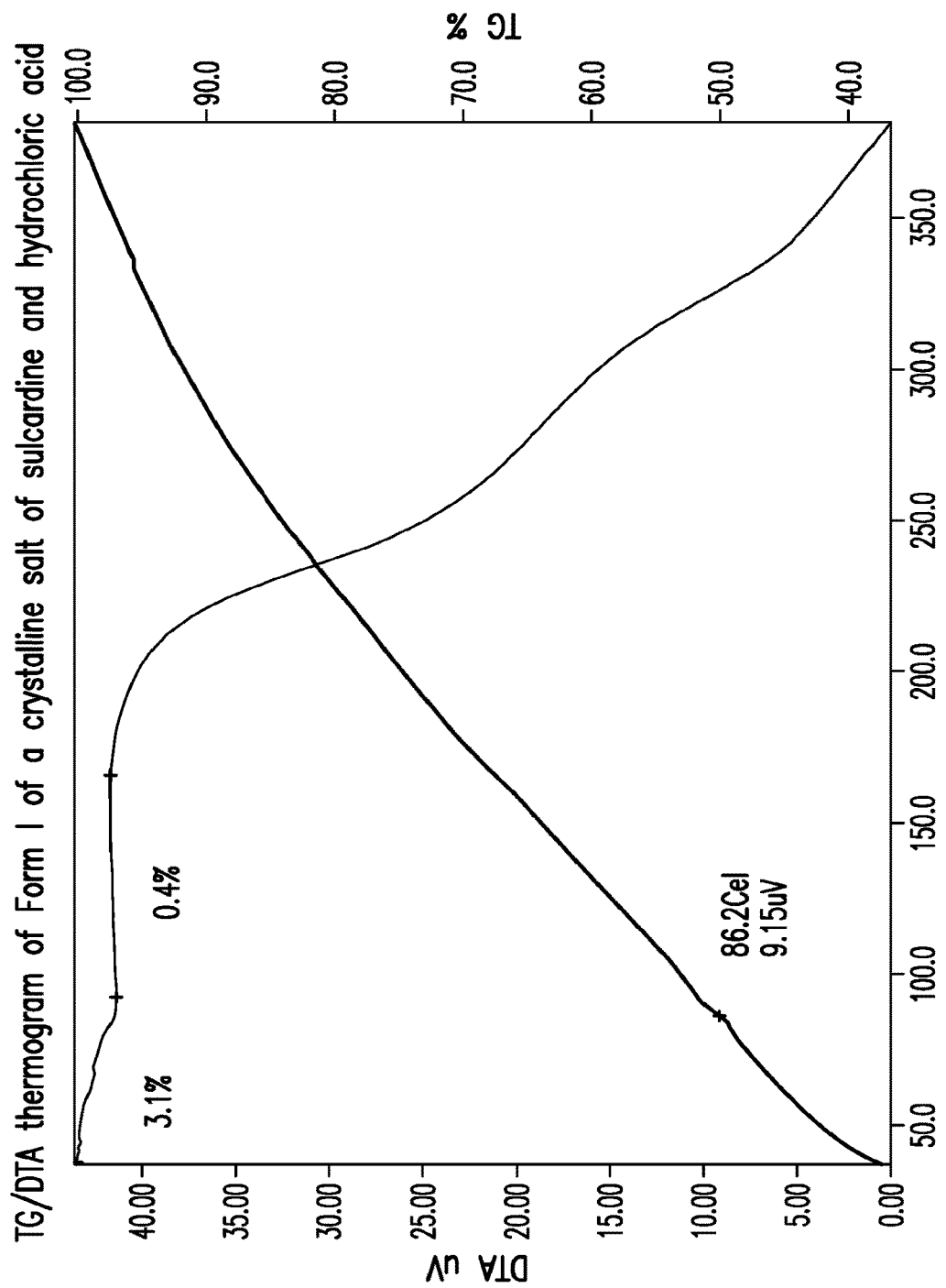
FIG. 18 is a representative TG/DTA thermogram of Form I of a crystalline salt of sulcardine and hydrochloric acid.

Representative TG/DTA thermograms of Form I of a sulcardine hydrochloride salt are provided in FIG. 18. In some embodiments, provided herein is a solid form comprising a sulcardine hydrochloride salt, which exhibits a weight loss of about 3.1% upon heating from about 25° C. to about 90° C. In some embodiments, without being limited by a particular theory, the weight loss corresponds to loss of water. In some embodiments, provided herein is a solid form comprising a sulcardine hydrochloride salt, characterized by a TG thermogram that matches the TG thermogram presented in FIG. 18.

In some embodiments, provided herein is a solid form comprising a sulcardine hydrochloride salt, characterized by a DTA thermogram that matches the DTA thermogram presented in FIG. 18.

In some embodiments, provided herein is a solid form comprising a sulcardine hydrochloride salt, which exhibits a mass increase of about 2.2% when subjected to an increase in a relative humidity (RH) from about 10% to about 90%.

In some embodiments, Form I of a sulcardine hydrochloride salt is prepared by subjecting a mixture of sulcardine and hydrochloric acid (e.g., about 1:1 molar ratio) in a solvent (e.g., TIF) to a temperature cycle (e.g., between about 5° C. and about 25° C.) for a period of time (e.g., about 72 hours).

In additional embodiments, crystalline salts of sulcardine and hydrochloric acid (also referred to as sulcardine hydrochloride) are provided. The hydrochloride salt is polymorphic. Example 11 produced Form II of a crystalline salt of sulcardine and hydrochloric acid. Upon scale-up, Form I of a crystalline salt of sulcardine and hydrochloric acid was made. Form I may be characterized by an XRPD pattern comprising one or more peaks chosen from about 12.3°2Θ and about 13.0°2Θ. In some embodiments, the XRPD pattern for Form I lacks a peak below about 9.5°2Θ. An XRPD pattern substantially the same as that of FIG. 17 may also be used to characterize Form I of a crystalline salt of sulcardine and hydrochloric acid. A peak list corresponding to many of the peaks in FIG. 17 appears in Table 9.

TABLE 9

XRPD Peak Table Corresponding to FIG. 17

| Position (°2θ) | d-spacing (Å) | Height (counts) | Relative Intensity (%) |
|---|---|---|---|
| 10.22 | 8.66 | 300.67 | 11.38 |
| 11.36 | 7.79 | 675.81 | 25.58 |
| 11.46 | 7.72 | 424.83 | 16.08 |
| 12.33 | 7.18 | 488.93 | 18.51 |
| 12.68 | 6.98 | 312.92 | 11.84 |
| 13.04 | 6.79 | 683.23 | 25.86 |
| 13.64 | 6.49 | 223.45 | 8.46 |
| 13.93 | 6.36 | 1401.98 | 53.07 |
| 14.80 | 5.99 | 519.94 | 19.68 |
| 16.13 | 5.50 | 449.22 | 17.00 |
| 16.33 | 5.43 | 176.44 | 6.68 |
| 17.20 | 5.16 | 867.18 | 32.82 |
| 17.36 | 5.11 | 1662.60 | 62.93 |
| 17.84 | 4.97 | 2641.96 | 100.00 |
| 18.06 | 4.91 | 726.55 | 27.50 |
| 18.56 | 4.78 | 1020.63 | 38.63 |
| 19.24 | 4.61 | 565.65 | 21.41 |
| 19.84 | 4.48 | 816.78 | 30.92 |
| 20.01 | 4.44 | 517.67 | 19.59 |
| 20.28 | 4.38 | 1252.88 | 47.42 |
| 20.52 | 4.33 | 256.72 | 9.72 |
| 20.74 | 4.28 | 137.55 | 5.21 |
| 21.94 | 4.05 | 1439.82 | 54.50 |
| 22.46 | 3.96 | 159.16 | 6.02 |
| 22.68 | 3.92 | 190.64 | 7.22 |
| 23.38 | 3.80 | 284.59 | 10.77 |
| 23.61 | 3.77 | 405.95 | 15.37 |
| 23.85 | 3.73 | 2280.36 | 86.31 |
| 24.44 | 3.64 | 141.40 | 5.35 |
| 24.81 | 3.59 | 370.66 | 14.03 |
| 25.40 | 3.50 | 545.64 | 20.65 |
| 25.51 | 3.49 | 497.09 | 18.82 |
| 25.95 | 3.43 | 185.92 | 7.04 |
| 26.85 | 3.32 | 189.34 | 7.17 |
| 27.36 | 3.26 | 571.69 | 21.64 |
| 27.79 | 3.21 | 283.01 | 10.71 |
| 28.01 | 3.19 | 187.54 | 7.10 |
| 28.37 | 3.15 | 472.36 | 17.88 |
| 28.86 | 3.09 | 334.24 | 12.65 |
| 29.39 | 3.04 | 167.27 | 6.33 |
| 29.87 | 2.99 | 213.81 | 8.09 |
| 30.32 | 2.95 | 114.60 | 4.34 |
| 30.66 | 2.92 | 135.45 | 5.13 |
| 31.03 | 2.88 | 111.04 | 4.20 |
| 31.93 | 2.80 | 160.34 | 6.07 |
| 32.46 | 2.76 | 266.62 | 10.09 |
| 33.18 | 2.70 | 274.03 | 10.37 |
| 33.91 | 2.64 | 159.84 | 6.05 |

In the TG/DTA experiment of FIG. 18, a weight loss of about 3.1% was observed which corresponds to about 0.88 equivalents of water for Form I. This is consistent with a hydrate. Thus, the crystalline salt prepared in accordance with Example 12 (Form I), for instance, produces a hydrate of a crystalline salt of sulcardine and hydrochloric acid.

A DVS experiment indicated that the salt prepared according to Example 12 (Form I) had an uptake of about 2.2% water at 90% RH. The crystalline form of the salt before the DVS experiment and afterwards was the same. Under stability conditions of exposure for one week at 40° C. and 75% RH, the salt was unchanged by XRPD. After 80° C. and ambient humidity after one week, the salt had changed into an orange gel, and under ambient light conditions after one week, the material was unchanged by XRPD. HPLC measurements done after these stability experiments showed that the purity had dropped from 99% to 98% after one week at 40° C. and 75% RH, to 90% after one week at 80° C., and unchanged (99%) after one week under ambient light conditions.

All of the combinations of the above embodiments are encompassed by this application.

6. Form H of Sulcardine Hydrochloride Salt

In certain embodiments, provided herein is Form II of a sulcardine hydrochloride salt. In some embodiments, the salt is crystalline.

In some embodiments, the molar ratio of sulcardine to hydrochloric acid in the salt is about 1:1. In some embodiments, the salt is a mono-hydrochloride salt of sulcardine.

A representative XRPD pattern of Form II of a sulcardine hydrochloride salt is provided in FIG. 17A.

In some embodiments, provided herein is a solid form comprising a sulcardine hydrochloride salt, characterized by 1, 2, 3, 4, 5, 6, 7, 8, 9, 10, 11, 12, 13, 14, 15, 16, 17, 18, 19, 20, or all of the peaks located at approximately the following positions: 10.1, 11.8, 13.5, 15.9, 16.4, 17.5, 17.8, 18.2, 18.4, 19.4, 19.6, 20.3, 20.6, 22.5, 23.5, 24.5, 25.5, 26.5, 26.6, 27.0, and 33.2° 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by all of the peaks.

In some embodiments, provided herein is a solid form comprising a sulcardine hydrochloride salt, characterized by an XRPD pattern comprising peaks at approximately 13.5, 19.6, and 20.6° 2θ. In some embodiments, the XRPD pattern further comprises peaks at approximately 10.1, 11.8, and 16.4° 2θ. In some embodiments, the XRPD pattern further comprises peaks at approximately 17.8, 19.4, and 25.5° 2θ. In some embodiments, the XRPD pattern comprises peaks at approximately 10.1, 11.8, 13.5, 15.9, 16.4, 17.8, 19.4, 19.6, 20.6, 23.5, 25.5, 26.5, 26.6, and 27.0° 2θ. In some embodiments, the XRPD pattern does not contain a peak at approximately 12.3° 2θ. In some embodiments, the XRPD pattern does not contain a peak at approximately 13.0° 2θ.

In some embodiments, provided herein is a solid form comprising a sulcardine hydrochloride salt, characterized by an XRPD pattern comprising peaks at approximately 11.8, 13.5, 19.6, and 20.6° 2θ. In some embodiments, the XRPD pattern further comprises peaks at approximately 17.8, 19.4, and 25.5° 2θ. In some embodiments, the XRPD pattern further comprises peaks at approximately 23.5 and 26.5° 2θ. In some embodiments, the XRPD pattern does not contain a peak at approximately 12.3° 2θ. In some embodiments, the XRPD pattern does not contain a peak at approximately 13.0° 2θ.

In some embodiments, provided herein is a solid form comprising a sulcardine hydrochloride salt, characterized by an XRPD pattern that matches the XRPD pattern presented in FIG. 17A.

In some embodiments, the XRPD patterns are obtained using Cu Kα radiation.

In some embodiments, Form II of a sulcardine hydrochloride salt is prepared by subjecting a mixture of sulcardine and hydrochloric acid (e.g., about 1:1 molar ratio) in a solvent (e.g., a mixture of 2-propanol and heptane) to a temperature cycle (e.g., between ambient temperature and about 40° C.) for a period of time (e.g., about 72 hours). In some embodiments, the solvent is a 2:1 v/v mixture of 2-propanol and heptane.

Form II may be characterized by an XRPD pattern comprising one or more peaks chosen from about 10.1°2Θ, 11.8° 2Θ, about 13.5° 2Θ, and about 16.4°2Θ and which lacks a peak between the peaks at about 10.1°2Θ and about 11.8°2Θ. In some embodiments, the XRPD pattern for Form II lacks a peak below about 9.5°2Θ. An XRPD pattern for Form II appears in FIG. 17A and Table 9A below is a peak table for certain peaks in FIG. 17A.

TABLE 9A

XRPD Peak Table Corresponding to FIG. 17A

| Position (°2θ) | d-spacing (Å) | Height (counts) | Relative Intensity (%) |
| --- | --- | --- | --- |
| 10.12 | 8.74 | 681.32 | 26.84 |
| 11.84 | 7.47 | 369.32 | 14.55 |
| 12.82 | 6.91 | 63.84 | 2.51 |
| 13.10 | 6.76 | 110.39 | 4.35 |
| 13.49 | 6.56 | 2538.87 | 100.00 |
| 15.87 | 5.58 | 524.69 | 20.67 |
| 16.43 | 5.40 | 591.14 | 23.28 |
| 17.47 | 5.08 | 398.30 | 15.69 |
| 17.77 | 4.99 | 1071.67 | 42.21 |
| 18.21 | 4.87 | 228.77 | 9.01 |
| 18.40 | 4.82 | 310.33 | 12.22 |
| 19.44 | 4.57 | 1544.92 | 60.85 |
| 19.64 | 4.52 | 2246.73 | 88.49 |
| 20.29 | 4.38 | 248.44 | 9.79 |
| 20.62 | 4.31 | 1593.00 | 62.74 |
| 20.89 | 4.25 | 194.17 | 7.65 |
| 21.50 | 4.13 | 197.47 | 7.78 |
| 22.45 | 3.96 | 393.25 | 15.49 |
| 22.94 | 3.88 | 84.83 | 3.34 |
| 23.53 | 3.78 | 714.86 | 28.16 |
| 24.19 | 3.68 | 56.04 | 2.21 |
| 24.54 | 3.63 | 227.53 | 8.96 |
| 25.47 | 3.50 | 1004.01 | 39.55 |
| 25.80 | 3.45 | 137.82 | 5.43 |
| 26.51 | 3.36 | 899.17 | 35.42 |
| 26.58 | 3.36 | 685.29 | 26.99 |
| 27.03 | 3.30 | 567.72 | 22.36 |
| 27.38 | 3.26 | 133.29 | 5.25 |
| 28.34 | 3.15 | 142.10 | 5.60 |
| 29.08 | 3.07 | 94.63 | 3.73 |
| 29.45 | 3.03 | 66.95 | 2.64 |
| 30.70 | 2.91 | 66.42 | 2.62 |
| 31.11 | 2.87 | 32.85 | 1.29 |
| 32.03 | 2.79 | 81.34 | 3.20 |
| 33.18 | 2.70 | 338.04 | 13.31 |
| 34.15 | 2.62 | 109.96 | 4.33 |

Because hydrochloric acid is a liquid under the experimental conditions used herein, the solid obtained is not a mixture of hydrochloric acid and amorphous sulcardine free base. The solid is a crystalline salt of sulcardine and hydrochloric acid.

All of the combinations of the above embodiments are encompassed by this application.

7. Hemi-Edisylate Salt of Sulcardine

In certain embodiments, provided herein is an ethane-1,2-disulfonic acid salt of sulcardine. In some embodiments, the salt is crystalline.

In some embodiments, the molar ratio of sulcardine to ethane-1,2-disulfonic acid in the salt is about 2:1. In some embodiments, the salt is a hemi-ethane-1,2-disulfonic acid salt of sulcardine.

A representative XRPD pattern of an ethane-1,2-disulfonic acid salt of sulcardine is provided in FIG. 19.

In some embodiments, provided herein is a solid form comprising an ethane-1,2-disulfonic acid salt of sulcardine, characterized by 1, 2, 3, 4, 5, 6, 7, 8, 9, 10, 11, 12, 13, 14, 15, 16, 17, 18, 19, 20, 21, or all of the peaks located at approximately the following positions: 5.6, 11.0, 13.0, 14.1, 14.9, 16.2, 16.8, 17.2, 17.5, 17.8, 18.8, 19.4, 19.6, 20.4, 21.7, 21.8, 22.2, 23.7, 25.1, 25.7, 25.8, and 27.2° 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by all of the peaks.

In some embodiments, provided herein is a solid form comprising an ethane-1,2-disulfonic acid salt of sulcardine, characterized by an XRPD pattern comprising peaks at approximately 14.1, 17.8, and 23.7° 2θ. In some embodiments, the XRPD pattern further comprises peaks at approximately 5.6 and 14.9° 2θ. In some embodiments, the XRPD pattern further comprises peaks at approximately 11.0 and 13.0° 2θ. In some embodiments, the XRPD pattern comprises peaks at approximately 5.6, 11.0, 13.0, 14.1, 14.9, 16.2, 17.2, 17.5, 17.8, 18.8, 19.6, 20.4, 21.8, and 23.7° 2θ.

In some embodiments, provided herein is a solid form comprising an ethane-1,2-disulfonic acid salt of sulcardine, characterized by an XRPD pattern that matches the XRPD pattern presented in FIG. 19.

In some embodiments, the XRPD patterns are obtained using Cu Kα radiation.

Figure 20:
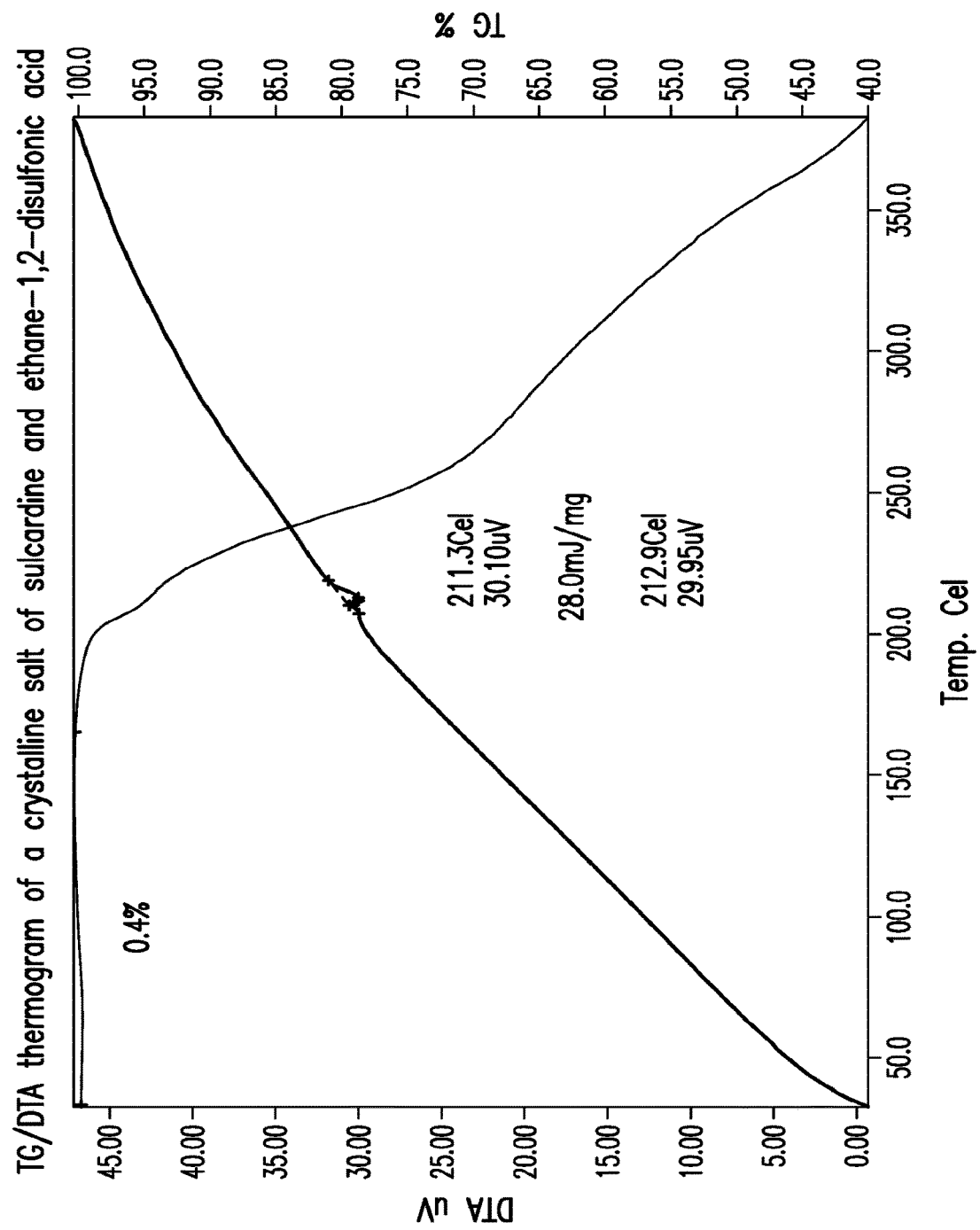
FIG. 20 is a representative TG/DTA thermogram of a crystalline salt of sulcardine and ethane-1,2-disulfonic acid.

Representative TG/DTA thermograms of an hemi-edisylate salt of sulcardine are provided in FIG. 20. In some embodiments, provided herein is a solid form comprising an ethane-1,2-disulfonic acid salt of sulcardine, which exhibits a weight loss of about 0.4% upon heating from about 25° C. to about 160° C. In some embodiments, provided herein is a solid form comprising an ethane-1,2-disulfonic acid salt of sulcardine, characterized by a TG thermogram that matches the TG thermogram presented in FIG. 20.

In some embodiments, provided herein is a solid form comprising an ethane-1,2-disulfonic acid salt of sulcardine, which exhibits, as characterized by DTA, a thermal event with an onset temperature of about 211° C. In some embodiments, the thermal event also has a peak temperature of about 213° C. In some embodiments, without being limited by any particular theory, the thermal event corresponds to the melting of the solid form. In some embodiments, provided herein is a solid form comprising an ethane-1,2-disulfonic acid salt of sulcardine, characterized by a DTA thermogram that matches the DTA thermogram presented in FIG. 20.

In some embodiments, provided herein is a solid form comprising an ethane-1,2-disulfonic acid salt of sulcardine, which exhibits a mass increase of about 0.5% when subjected to an increase in a relative humidity (RH) from about 10% to about 90%.

In some embodiments, the hemi-ethane-1,2-disulfonic acid salt of sulcardine is prepared by subjecting a mixture of sulcardine and ethane-1,2-disulfonic acid (e.g., about 2:1 molar ratio) in a solvent to a temperature cycle (e.g., between about 5° C. and about 25° C.) for a period of time (e.g., about 72 hours). In other embodiments, the temperature cycle is between ambient temperature and about 40° C. In some embodiments, the solvent is toluene. In some embodiments, the solvent is a mixture of toluene and heptane (e.g., 2:1 v/v).

In additional embodiments, provides herein are crystalline salts of sulcardine and ethane-1,2-disulfonic acid. A preparation of a crystalline salt of sulcardine and ethane-1,2-disulfonic acid is provided in Example 13, with a scaled-up preparation in Example 14. Such crystalline salts may be characterized by an XRPD pattern comprising one or more peaks chosen from about 5.6° 2Θ, about 11.0°2Θ, about 13.0°2Θ, about 14.1° 2Θ, and about 14.9°2Θ. An XRPD pattern substantially the same as that of FIG. 19 may also be used to characterize a crystalline salt of sulcardine and ethane-1,2-disulfonic acid. These crystalline salts may be characterized by a melting onset temperature of about 211° C. with or without the characteristic XRPD data. Thus, for example, crystalline salts of sulcardine and ethane-1,2-disulfonic acid may be characterized by a melting onset temperature of about 211° C. and (a) an XRPD pattern comprising one or more peaks chosen from about 5.6°2Θ, about 11.0°2Θ, about 13.0°2Θ, about 14.1° 2Θ, and about 14.9°2Θ or (b) an XRPD pattern substantially the same as that of FIG. 19. A peak list corresponding to many of the peaks in FIG. 19 appears in Table 10. The solubility of crystalline ethane-1,2-disulfonic acid salt of sulcardine is set forth in Table 11.

TABLE 10

XRPD Peak Table Corresponding to FIG. 19

| Position (°2θ) | d-spacing (Å) | Height (counts) | Relative Intensity (%) |
|---|---|---|---|
| 5.57 | 15.86 | 540.23 | 23.02 |
| 10.30 | 8.59 | 58.41 | 2.49 |
| 11.04 | 8.02 | 362.80 | 15.46 |
| 13.01 | 6.80 | 293.26 | 12.50 |
| 14.08 | 6.29 | 1596.56 | 68.04 |
| 14.91 | 5.94 | 800.37 | 34.11 |
| 16.17 | 5.48 | 769.99 | 32.81 |
| 16.81 | 5.28 | 566.17 | 24.13 |
| 17.19 | 5.16 | 752.16 | 32.05 |
| 17.51 | 5.07 | 836.58 | 35.65 |
| 17.80 | 4.98 | 2346.65 | 100.00 |
| 18.78 | 4.72 | 1215.08 | 51.78 |
| 19.39 | 4.58 | 629.39 | 26.82 |
| 19.56 | 4.54 | 1338.23 | 57.03 |
| 20.03 | 4.43 | 253.56 | 10.81 |
| 20.40 | 4.35 | 1052.82 | 44.86 |
| 20.72 | 4.29 | 216.99 | 9.25 |
| 21.70 | 4.09 | 1084.31 | 46.21 |
| 21.77 | 4.08 | 1509.90 | 64.34 |
| 22.20 | 4.00 | 780.52 | 33.26 |
| 22.92 | 3.88 | 193.45 | 8.24 |
| 23.71 | 3.75 | 2285.76 | 97.40 |
| 24.46 | 3.64 | 330.10 | 14.07 |
| 25.06 | 3.55 | 617.83 | 26.33 |
| 25.74 | 3.46 | 436.99 | 18.62 |
| 25.78 | 3.46 | 437.79 | 18.66 |
| 26.44 | 3.37 | 135.81 | 5.79 |
| 27.16 | 3.28 | 367.43 | 15.66 |
| 27.50 | 3.24 | 285.44 | 12.16 |
| 28.65 | 3.12 | 229.50 | 9.78 |
| 29.15 | 3.06 | 208.61 | 8.89 |
| 29.65 | 3.01 | 131.08 | 5.59 |
| 30.09 | 2.97 | 241.51 | 10.29 |
| 31.59 | 2.83 | 134.52 | 5.73 |
| 32.47 | 2.76 | 150.91 | 6.43 |
| 33.52 | 2.67 | 136.46 | 5.82 |
| 33.98 | 2.64 | 186.80 | 7.96 |

Figure 22:
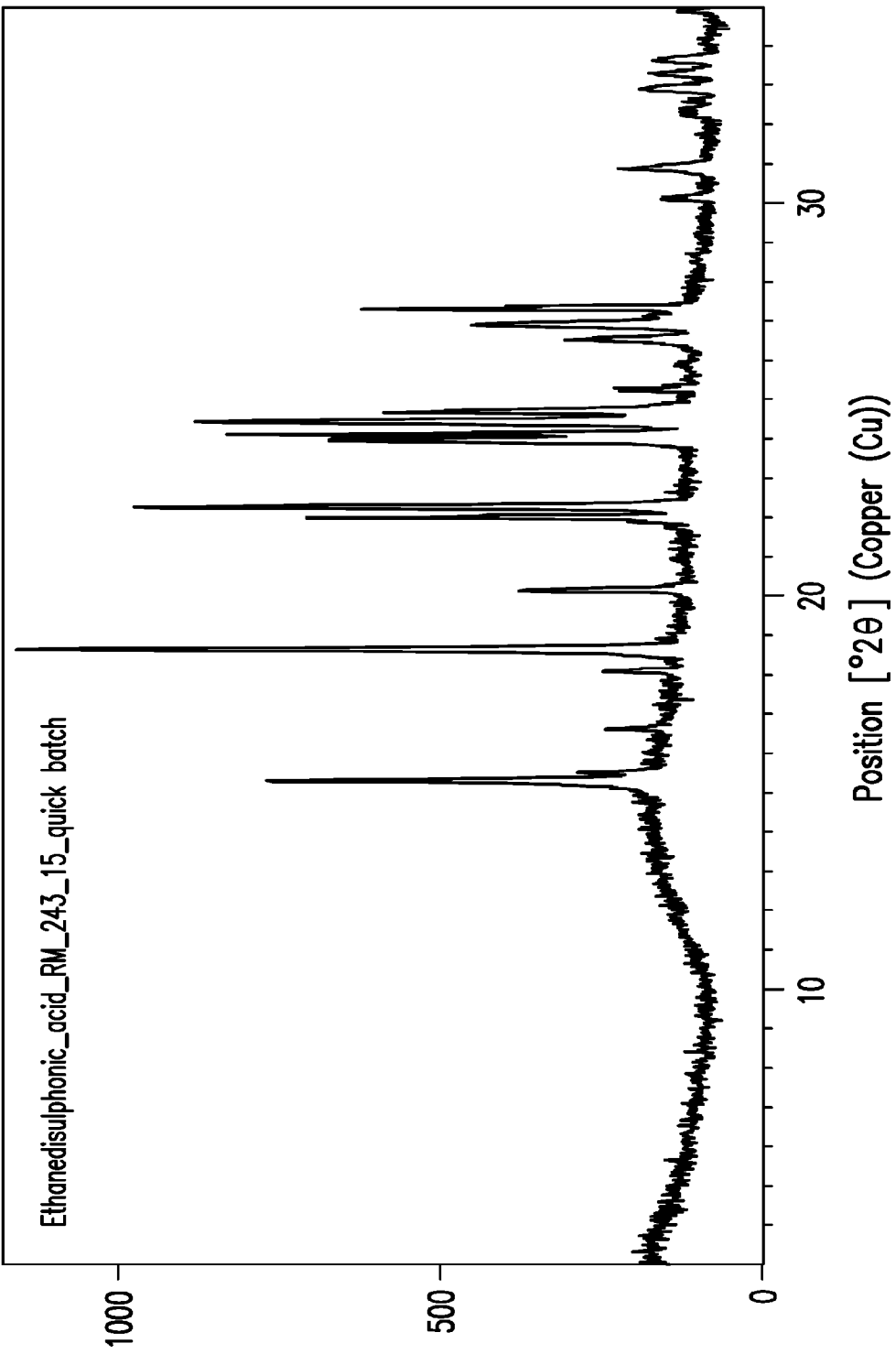
FIG. 22 is a representative XRPD pattern of ethane-1,2-disulfonic acid.

The XRPD patterns of crystalline salts of sulcardine and ethane-1,2-disulfonic acid are not linear combinations of the XRPD patterns of amorphous sulcardine free base and ethane-1,2-disulfonic acid. For example, the salt has a peak at about 5.6°2Θ. No such peak is in the XRPD pattern of the corresponding ethane-1,2-disulfonic acid as seen in FIG. 22, and the free base XRPD pattern of sulcardine does not have any peaks. Thus, the XRPD pattern of FIG. 19 is not a physical mixture of the salt starting materials. The solubility of ethane-1,2-disulfonic acid salt of sulcardine is set forth in Table 11 below and was prepared according to the procedures of Example 3.

Further, a unique XRPD diffractogram and DTA melting event confirm that a new solid form has been produced. The ¹H-NMR spectrum shows the presence of about 0.5 equivalent the counterion and possibly peak shifts compared with the free base, confirming that the material is a salt rather than a new polymorph or a solvate/hydrate of the individual components.

Figure 21:
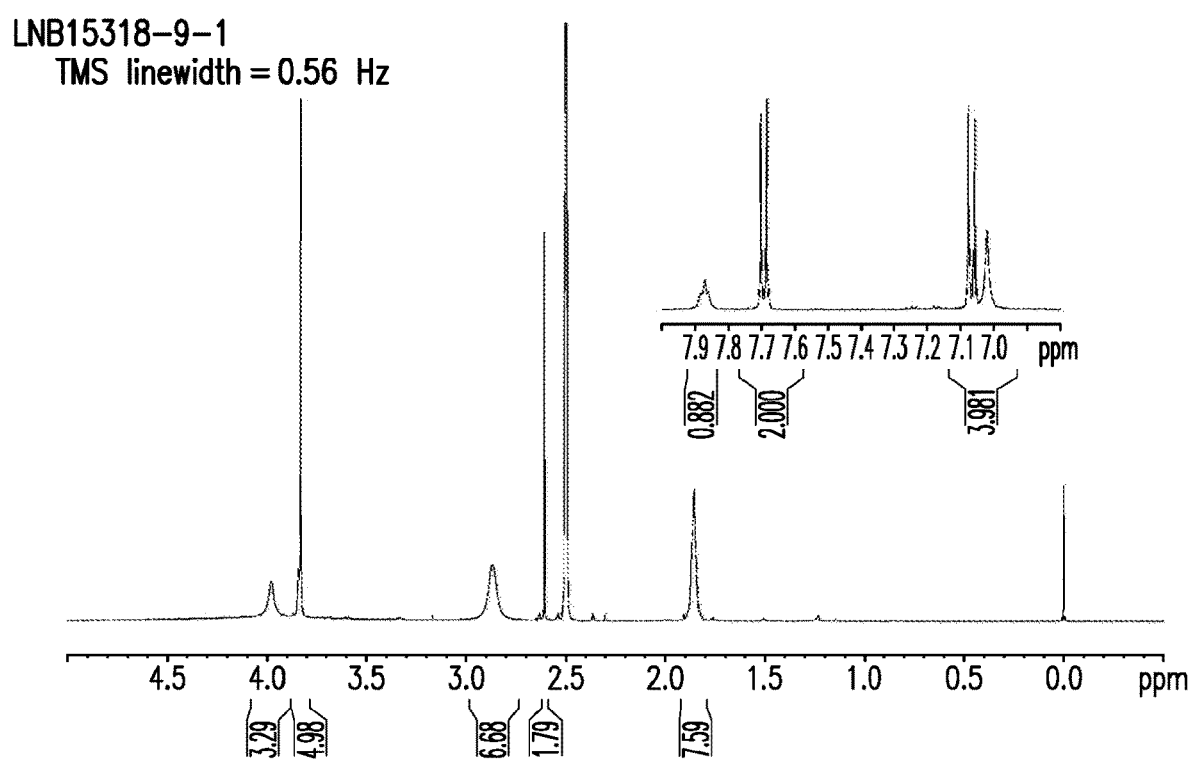
FIG. 21 is a representative $^1$H-NMR spectrum of a crystalline salt of sulcardine and ethane-1,2-disulfonic acid.

In the ¹H-NMR spectrum of FIG. 21 which is the salt of Example 14, 0.5 equivalents of ethane-1,2-disulfonic acid were observed. This is consistent with a hemi salt, such that there is 1 equivalent of ethane-1,2-disulfonic acid for every two equivalents of sulcardine free base in the salt. Ethane-1,2-disulfonic acid has two acidic groups which can form a salt with the sulcardine free base. In this hemi salt, therefore, two sulcardine free base molecules are forming a salt with one free acid molecule.

A DVS experiment indicated that the salt prepared according to Example 14 had an uptake of about 0.5% water at 90% RH. The crystalline form of the salt before the DVS experiment and afterwards was the same. Under stability conditions of exposure for one week at 40° C. and 75% RH, the salt was unchanged by XRPD. After 80° C. and ambient humidity after one week, the salt was unchanged by XRPD, and under ambient light conditions after one week, the material was unchanged by XRPD. HPLC measurements done after these stability experiments showed that the purity had dropped from 99% to 98% after one week at 40° C. and 75% RH, to 97% after one week at 80° C., and to 97% after one week under ambient light conditions.

TABLE 11

Solubility Data of Hemi- Ethane-1,2-Disulfonic Acid Salt of Sulcardine

| Buffer pH | pH after addition | pH after adjustment | Temperature (° C.) | pH after 72 hr | pH after adjustment | Temperature (° C.) | Solubility (mg · mL⁻¹) |
|---|---|---|---|---|---|---|---|
| 1.2 | 1.7 | 1.2 | 18.8 | 1.2 | N/A | 18.7 | 41.1 |
| 3.0 | 6.7 | 3.0 | 18.8 | 4.3 | 3.0 | 18.7 | 46.3 |
| 4.0 | 5.8 | 4.0 | 18.8 | 4.1 | 4.1 | 18.5 | 36.1 |
| 7.4 | 7.8 | 7.3 | 18.7 | 7.5 | N/A | 18.5 | 18.9 |

All of the combinations of the above embodiments are encompassed by this application.

8. Form I of Mono-Edisylate Salt of Sulcardine

In certain embodiments, provided herein is an ethane-1,2-disulfonic acid salt of sulcardine. In some embodiments, the salt is crystalline.

In some embodiments, the molar ratio of sulcardine to ethane-1,2-disulfonic acid in the salt is about 1:1. In some embodiments, the salt is a mono-ethane-1,2-disulfonic acid salt of sulcardine. In some embodiments, provided herein is Form I of a monoedisylate salt of sulcardine. In some embodiments, Form I is a hydrate of a monoedisylate salt of sulcardine. In some embodiments, Form I is a mono-hydrate of a monoedisylate salt of sulcardine.

Figure 26:
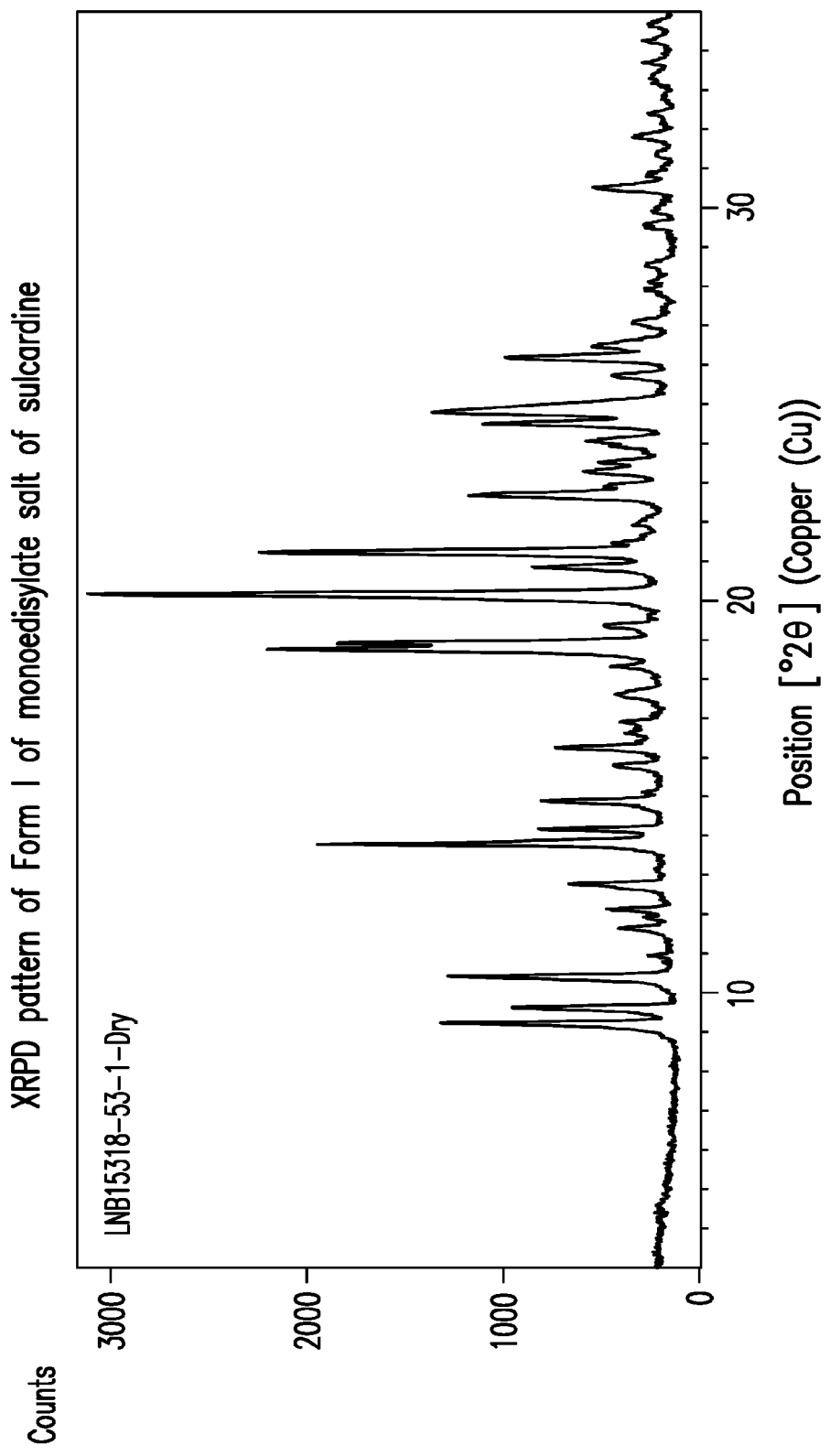
FIG. 26 is a representative XRPD pattern of Form I of monoedisylate salt of sulcardine.

A representative XRPD pattern of Form I of a mono-ethane-1,2-disulfonic acid salt (mono-edisylate salt) of sulcardine is provided in FIG. 26.

In some embodiments, provided herein is a solid form comprising an ethane-1,2-disulfonic acid salt of sulcardine, characterized by 1, 2, 3, 4, 5, 6, 7, 8, 9, 10, 11, 12, 13, 14, 15, 16, 17, or all of the peaks located at approximately the following positions: 9.2, 9.6, 10.4, 12.8, 13.8, 14.2, 14.9, 16.3, 18.8, 18.9, 20.2, 20.8, 21.2, 22.7, 23.3, 24.5, 24.8, and 26.2° 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by all of the peaks.

In some embodiments, provided herein is a solid form comprising an ethane-1,2-disulfonic acid salt of sulcardine, characterized by an XRPD pattern comprising peaks at approximately 18.8, 20.2, and 21.2° 2θ. In some embodiments, the XRPD pattern further comprises peaks at approximately 9.2, 10.4, and 13.8° 2θ. In some embodiments, the XRPD pattern further comprises peaks at approximately 9.6, 14.2, and 14.9° 2θ. In some embodiments, the XRPD pattern comprises peaks at approximately 9.2, 9.6, 10.4, 13.8, 14.2, 14.9, 18.8, 18.9, 20.2, 21.2, 22.7, and 24.8° 2θ.

In some embodiments, provided herein is a solid form comprising an ethane-1,2-disulfonic acid salt of sulcardine, characterized by an XRPD pattern that matches the XRPD pattern presented in FIG. 26.

In some embodiments, the XRPD patterns are obtained using Cu Kα radiation.

Figure 27:
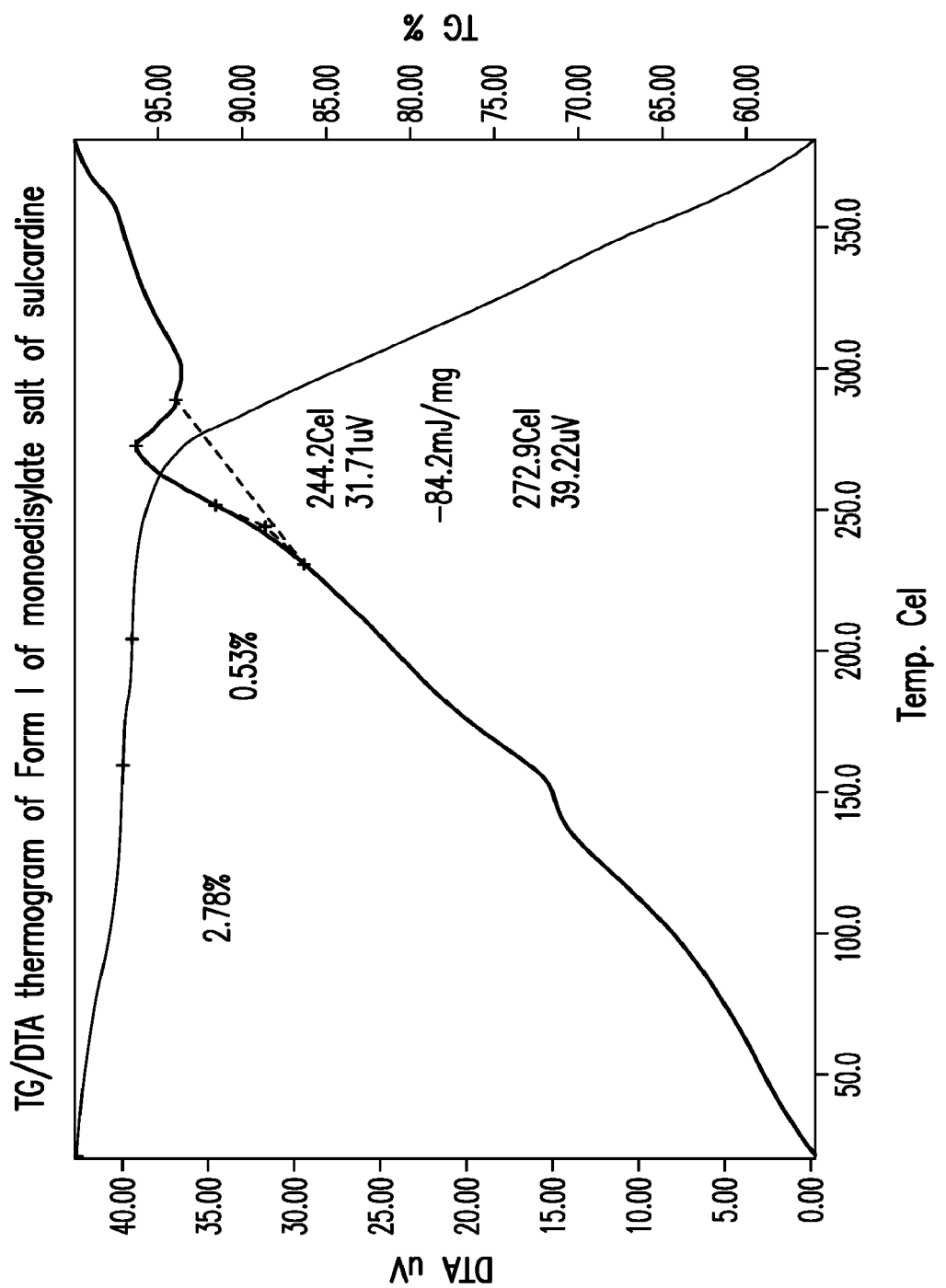
FIG. 27 is a representative TG/DTA thermogram of Form I of monoedisylate salt of sulcardine.

Representative TG/DTA thermograms of Form I of a monoedisylate salt of sulcardine are provided in FIG. 27. In some embodiments, provided herein is a solid form comprising an ethane-1,2-disulfonic acid salt of sulcardine, which exhibits a weight loss of about 2.8% upon heating from about 25° C. to about 150° C., and a weight loss of about 0.5% upon heating from about 150° C. to about 200° C. In some embodiments, without being limited by any particular theory, the total weight loss corresponds to the loss of about 1 equivalent of water. In some embodiments, provided herein is a solid form comprising an ethane-1,2-disulfonic acid salt of sulcardine, characterized by a TG thermogram that matches the TG thermogram presented in FIG. 27.

In some embodiments, provided herein is a solid form comprising an ethane-1,2-disulfonic acid salt of sulcardine, which exhibits, as characterized by DTA, a thermal event with an onset temperature of about 244° C. In some embodiments, the thermal event also has a peak temperature of about 273° C. In some embodiments, without being limited by any particular theory, the thermal event corresponds to the degradation of the solid form. In some embodiments, provided herein is a solid form comprising an ethane-1,2-disulfonic acid salt of sulcardine, characterized by a DTA thermogram that matches the DTA thermogram presented in FIG. 27.

Figure 37A:
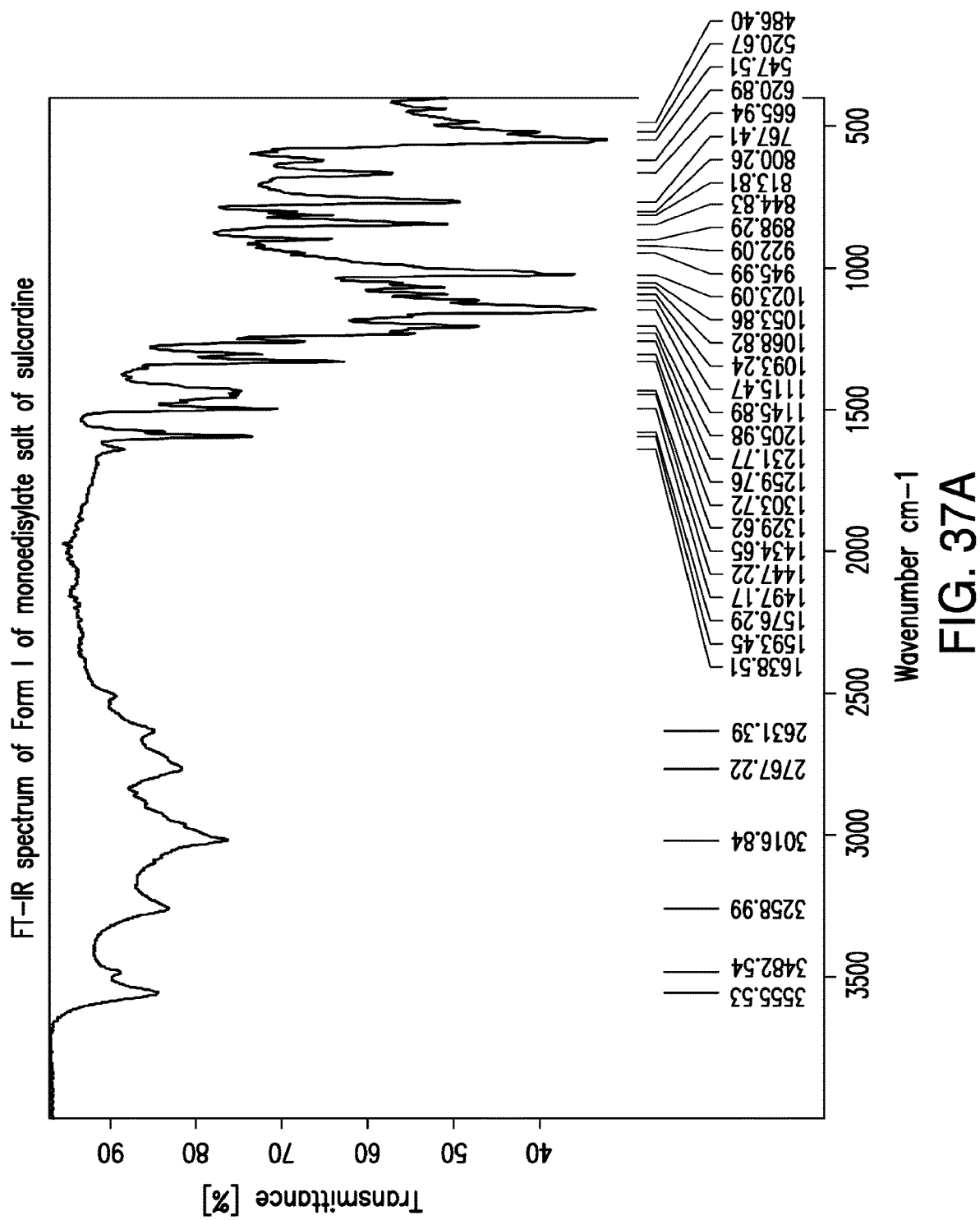
FIG. 37A is a representative FT-IR spectrum of Form I of monoedisylate salt of sulcardine.

A representative FT-IR spectrum of Form I of a monoedisylate salt of sulcardine is provided in FIG. 37A. In some embodiments, provided herein is a solid form comprising an ethane-1,2-disulfonic acid salt of sulcardine, characterized by a FT-IR spectrum comprising a peak above about 3500 cm⁻¹. In some embodiments, provided herein is a solid form comprising an ethane-1,2-disulfonic acid salt of sulcardine, characterized by a FT-IR spectrum comprising one or more peaks at approximately 3556, 1206, and 814 cm⁻¹. In some embodiments, the FT-IR spectrum comprising a peak at approximately 3556 cm⁻¹. In some embodiments, the FT-IR spectrum comprising a peak at approximately 1206 cm⁻¹. In some embodiments, the FT-IR spectrum comprising a peak at approximately 814 cm⁻¹. In some embodiments, the FT-IR spectrum comprises the following approximate peaks:

| Peak Shift (cm$^{-1}$) | Relative Intensity |
|---|---|
| 3556 | 122.47 |
| 3483 | 123.71 |
| 3259 | 3302.59 |
| 3017 | 252.73 |
| 2767 | 91.18 |
| 2631 | 33.02 |
| 1639 | 17.86 |
| 1593 | 14.70 |
| 1576 | 60.59 |
| 1497 | 13.11 |
| 1447 | 40.31 |
| 1435 | 45.66 |
| 1330 | 14.39 |
| 1304 | 10.36 |
| 1260 | 2208.13 |
| 1232 | 5.80 |
| 1206 | 15.59 |
| 1146 | 72.43 |
| 1115 | 66.80 |
| 1093 | 9.28 |
| 1069 | 10.60 |
| 1054 | 50.84 |
| 1023 | 24.78 |
| 946 | 12.70 |
| 922 | 46.33 |
| 898 | 8.59 |
| 845 | 22.97 |
| 814 | 6.66 |
| 800 | 5.68 |
| 767 | 26.59 |
| 666 | 20.65 |
| 621 | 18.06 |
| 548 | 47.25 |
| 521 | 8.68 |
| 486 | 12.29 |

In some embodiments, provided herein is a solid form comprising an ethane-1,2-disulfonic acid salt of sulcardine, characterized by a FT-IR spectrum that matches the FT-IR spectrum presented in FIG. 37A.

In some embodiments, provided herein is a solid form comprising an ethane-1,2-disulfonic acid salt of sulcardine, characterized by both an XRPD pattern and a FT-IR spectrum provided in this section. For example, in some embodiments, the solid form is characterized by an XRPD pattern comprising peaks at approximately 18.8, 20.2, and 21.2° 2θ, and is characterized by a FT-IR spectrum comprising a peak above 3500 cm$^{-1}$.

In some embodiments, Form I of monoedisylate salt of sulcardine is prepared by subjecting a mixture of sulcardine and ethane-1,2-disulfonic acid (e.g., about 1:1 molar ratio) in a solvent to a temperature cycle (e.g., between about ambient temperature and about 40° C.) for a period of time (e.g., about 48 hours). In some embodiments, the solvent is toluene.

In additional embodiments, provided herein is a monoedisylate salt of sulcardine. In such a salt, there is one equivalent of ethane-1,2-disulfonic acid for every one equivalent of sulcardine. Further provided herein are crystalline monoedisylate salts of sulcardine such as Form I of crystalline monoedisylate salt of sulcardine and Form II of crystalline monoedisylate salt of sulcardine. Form I of crystalline monoedisylate salt of sulcardine is provided in Example 17 and Form II of crystalline monoedisylate salt of sulcardine is provided in Example 18. Further provided herein are hydrates of monoedisylate sulcardine. Such hydrates include monohydrates and dihydrates.

Figure 30:
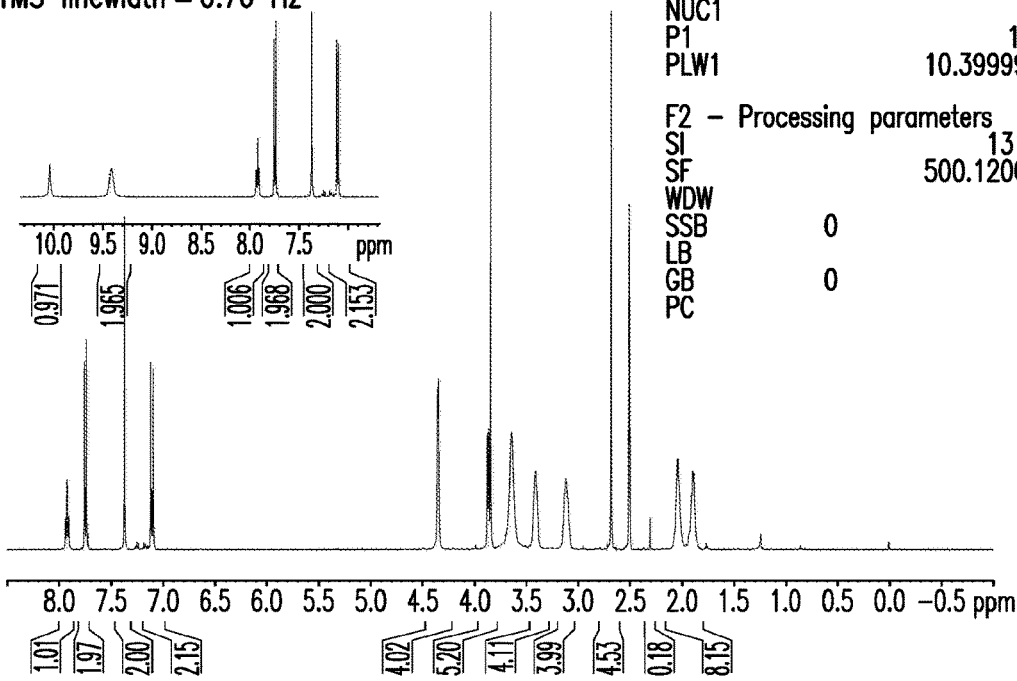
FIG. 30 is a representative $^1$H-NMR spectrum of Form I of monoedisylate salt of sulcardine.

Form I of crystalline monoedisylate salt of sulcardine is a monohydrate and may be characterized by an XRPD pattern having a peak at about 14.2°2Θ. Form I of crystalline monoedisylate salt may also be characterized by an XRPD pattern having a peak at about 9.2°2Θ with the absence of a peak at about 5.2°2Θ. Form I of crystalline monoedisylate salt may also be characterized by an XRPD pattern having two peaks between about 9.0°2Θ and about 9.8°2Θ. Form I of crystalline monoedisylate salt may also be characterized by an XRPD pattern having two peaks between about 9.0°2Θ and about 9.8°2Θ wherein the differences between the two peaks is about 0.4°2Θ. In some embodiments, the difference between the two peaks is 0.4°2Θ+0.1°2Θ. Form I of crystalline monoedisylate salt of sulcardine may also be characterized by an XRPD pattern comprising one or more peaks chosen from about 9.2°2Θ, about 9.6°2Θ, about 10.4° 2Θ, about 13.8° 2Θ, about 14.2° 2Θ, and about 14.9°2Θ. An XPRD pattern substantially the same as that of FIG. 26 may also be used to characterize Form I of crystalline monoedisylate salt of sulcardine. $^{1}$H-NMR spectroscopy may be used to confirm a 1:1 stoichiometry of ethane-1,2-disulfonic acid to sulcardine (see FIG. 30).

Form I of crystalline monoedisylate salt of sulcardine may also be characterized by an XRPD peak at about 14.2°2Θ and an FT-IR spectrum comprising a peak above about 3500 cm$^{-1}$. Form I of crystalline monoedisylate salt of sulcardine may also be characterized by an XRPD peak at about 14.2°2Θ with the absence of a peak at about 5.2°2Θ, and an FT-IR spectrum comprising a peak above about 3500 cm$^{-1}$, and further optionally comprising one or more FT-IR peaks at about 1206 cm$^{-1}$ and about 814 cm$^{-1}$. Form I of crystalline monoedisylate salt of sulcardine may also be characterized by an XRPD pattern having two peaks between about 9.0°2Θ and about 9.8°2Θ, and wherein in some embodiments the difference between the two peaks is about 0.4°2Θ, and an FT-IR spectrum comprising a peak above about 3500 cm$^{-1}$, and further optionally comprising one or more FT-IR peaks at about 1206 cm$^{-1}$ and about 814 cm$^{-1}$. Form I of crystalline monoedisylate salt of sulcardine may also be characterized by an XRPD pattern comprising one or more peaks at about 9.2°2Θ, about 9.6°2Θ, about 10.4°2Θ, about 13.8° 2Θ, about 14.2°2Θ, and about 14.9°2Θ, and an FT-IR spectrum comprising a peak above about 3500 cm$^{-1}$, and further optionally comprising one or more FT-IR peaks at about 1206 cm$^{-1}$ and about 814 cm$^{-1}$. In some embodiments herein, the peak at above about 3500 cm$^{-1}$ is at about 3556 cm$^{-1}$.

A TG/DTA thermogram of Form I of crystalline monoedisylate salt of sulcardine is shown in FIG. 27. This figure shows a mass loss of about 2.8% and also about 0.5% which is consistent with about 1 equivalent of water. Karl Fisher analysis of Form I showed a water content of 3%, or approximately 1 equivalent of water. This is consistent with the TG data which showed a mass loss of approximately 3.2% equating to 1 equivalent of water. Thus, Form I is a monohydrate. No melting was observed prior to degradation of 244° C. A peak list corresponding to many of the peaks in FIG. 26 appear in Table 11A below.

TABLE 11A

XRPD Peak Table Corresponding to FIG. 26

| Position (°2θ) | d-spacing (Å) | Height (counts) | Relative Intensity (%) |
|---|---|---|---|
| 9.24 | 9.57 | 1201.01 | 39.54 |
| 9.64 | 9.18 | 834.18 | 27.46 |
| 10.43 | 8.48 | 1171.61 | 38.57 |
| 10.95 | 8.08 | 123.70 | 4.07 |

TABLE 11A-continued

XRPD Peak Table Corresponding to FIG. 26

| Position (°2θ) | d-spacing (Å) | Height (counts) | Relative Intensity (%) |
|---|---|---|---|
| 11.69 | 7.57 | 234.65 | 7.72 |
| 11.90 | 7.44 | 143.27 | 4.72 |
| 12.13 | 7.29 | 356.05 | 11.72 |
| 12.79 | 6.92 | 521.37 | 17.16 |
| 13.78 | 6.43 | 1830.88 | 60.27 |
| 14.17 | 6.25 | 702.56 | 23.13 |
| 14.90 | 5.95 | 689.32 | 22.69 |
| 15.82 | 5.60 | 319.52 | 10.52 |
| 16.26 | 5.45 | 604.12 | 19.89 |
| 16.61 | 5.34 | 246.29 | 8.11 |
| 16.91 | 5.24 | 275.56 | 9.07 |
| 17.57 | 5.05 | 281.78 | 9.28 |
| 18.31 | 4.84 | 340.47 | 11.21 |
| 18.75 | 4.73 | 2126.07 | 69.99 |
| 18.91 | 4.69 | 1760.45 | 57.95 |
| 19.36 | 4.59 | 369.21 | 12.15 |
| 20.16 | 4.41 | 3037.68 | 100.00 |
| 20.84 | 4.26 | 729.02 | 24.00 |
| 21.22 | 4.19 | 2157.40 | 71.02 |
| 21.97 | 4.05 | 189.19 | 6.23 |
| 22.66 | 3.92 | 1004.82 | 33.08 |
| 22.94 | 3.88 | 339.16 | 11.17 |
| 23.27 | 3.82 | 463.64 | 15.26 |
| 23.52 | 3.78 | 375.21 | 12.35 |
| 24.08 | 3.70 | 412.11 | 13.57 |
| 24.49 | 3.63 | 1003.15 | 33.02 |
| 24.78 | 3.59 | 1218.59 | 40.12 |
| 25.75 | 3.46 | 311.13 | 10.24 |
| 26.19 | 3.40 | 861.54 | 28.36 |
| 26.47 | 3.37 | 408.66 | 13.45 |
| 27.08 | 3.29 | 213.95 | 7.04 |
| 27.87 | 3.20 | 113.08 | 3.72 |
| 28.54 | 3.13 | 148.42 | 4.89 |
| 29.50 | 3.03 | 139.71 | 4.60 |
| 29.89 | 2.99 | 111.32 | 3.66 |
| 30.49 | 2.93 | 405.51 | 13.35 |
| 30.83 | 2.90 | 134.88 | 4.44 |
| 31.32 | 2.86 | 95.18 | 3.13 |
| 31.82 | 2.81 | 189.90 | 6.25 |
| 32.39 | 2.76 | 124.64 | 4.10 |
| 33.38 | 2.68 | 115.93 | 3.82 |
| 33.69 | 2.66 | 157.79 | 5.19 |
| 34.23 | 2.62 | 138.31 | 4.55 |
| 34.65 | 2.59 | 121.38 | 4.00 |

The XRPD pattern of Form I of crystalline monoedisylate salt of sulcardine is not a linear combination of the XRPD patterns of ethane-1,2-disulfonic acid and amorphous sulcardine free base. For example, the Form I of crystalline monoedisylate salt of sulcardine has a peak at about 9.2°2Θ which is not present in the ethane-1,2-disulfonic acid XRPD pattern of FIG. 22, and amorphous sulcardine has no peaks. The XRPD pattern of FIG. 26 is not a physical mixture of the salt starting materials.

In some embodiments, Form I of the mono-edisylate salt of sulcardine converts to Form II of the mono-edisylate salt of sulcardine under aqueous conditions. When Form I of the mono-edisylate salt of sulcardine was tested to determine its thermodynamic solubility, high solubility (>150 mg/mL) was observed in all the buffer systems assessed (Table 11B). No solids were observed for XRPD analysis. HPLC analysis was not carried out on the samples due to the high solubility.

TABLE 11B

Observations and Results for Form I of Mono-Edisylate Salt of Sulcardine Thermodynamic Solubility in 20 mM Buffers

| Buffer | After 4 hours | | | After 16 hours | | | Conc. (mg/mL) |
|---|---|---|---|---|---|---|---|
| | Obs | pH | Adjusted pH | Obs. | pH | Adjusted pH | |
| pH 1.2 HCl/KCl | Clear colorless solution | 1.06 | 1.24 | Clear colorless solution | 0.55 | 1.20 | >150 |
| pH 3.0 HCl/glycine | Clear colorless solution | 2.46 | 3.02 | Clear colorless solution | 1.21 | 2.96 | >150 |
| pH 4.0 Citrate | Clear colorless solution | 3.16 | 4.05 | Clear colorless solution | 1.31 | 3.95 | >150 |
| pH 6.8 Phosphate | Clear colorless solution | 5.25 | 6.81 | Clear colorless solution | 1.35 | 6.74 | >150 |
| pH 7.4 Phosphate | Clear colorless solution | 5.86 | 7.26 | Clear colorless solution | 0.99 | 7.54 | >150 |
| pH 8.0 Phosphate | Clear colorless solution | 6.07 | 8.01 | Clear colorless solution | 1.1 | 7.93 | >150 |
| FaSSGF | Clear colorless solution | 1.17 | n/a | Clear colorless solution | 1.15 | n/a | >150 |

All of the combinations of the above embodiments are encompassed by this application.

9. Form II of Mono-Edisylate Salt of Sulcardine

In certain embodiments, provided herein is an ethane-1,2-disulfonic acid salt of sulcardine. In some embodiments, the salt is crystalline.

In some embodiments, the molar ratio of sulcardine to ethane-1,2-disulfonic acid in the salt is about 1:1. In some embodiments, the salt is a mono-ethane-1,2-disulfonic acid salt of sulcardine. In some embodiments, provided herein is Form II of a monoedisylate salt of sulcardine. In some embodiments, Form I is a hydrate of a monoedisylate salt of sulcardine. In some embodiments, Form II is a di-hydrate of a monoedisylate salt of sulcardine.

Figure 28:
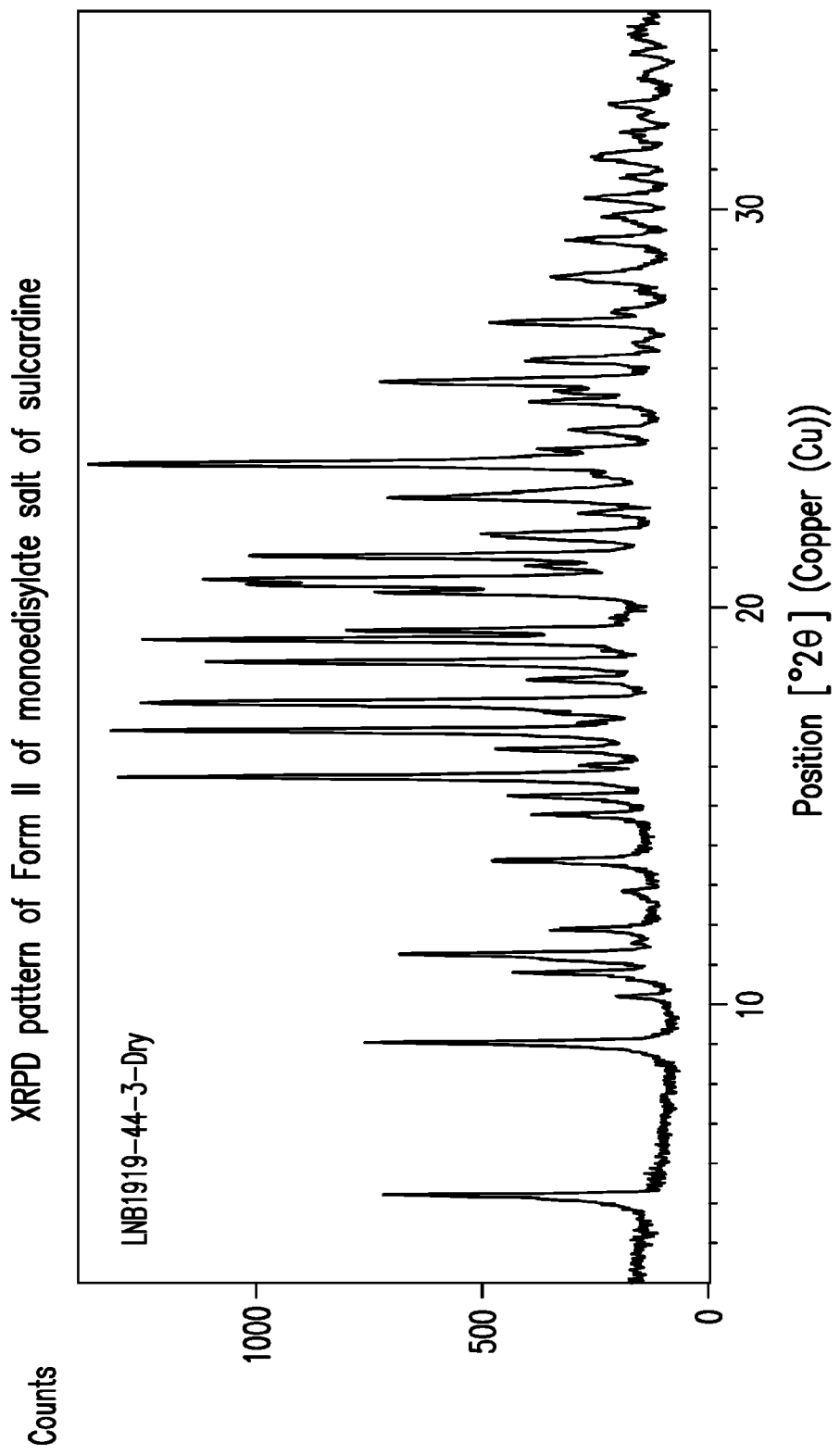
FIG. 28 is a representative XRPD pattern of Form II of monoedisylate salt of sulcardine.

A representative XRPD pattern of Form II of a mono-ethane-1,2-disulfonic acid salt (mono-edisylate salt) of sulcardine is provided in FIG. 28.

In some embodiments, provided herein is a solid form comprising an ethane-1,2-disulfonic acid salt of sulcardine, characterized by 1, 2, 3, 4, 5, 6, 7, 8, 9, 10, 11, 12, 13, 14, 15, 16, 17, 18, 19, 20, 21, 22, 23, 24, or all of the peaks located at approximately the following positions: 5.2, 9.1, 10.2, 10.8, 11.3, 11.9, 13.6, 14.8, 15.3, 15.7, 16.4, 16.9, 17.6, 18.2, 18.6, 19.2, 19.4, 20.4, 20.6, 20.7, 21.3, 21.9, 22.7, 23.6, and 25.7° 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by all of the peaks.

In some embodiments, provided herein is a solid form comprising an ethane-1,2-disulfonic acid salt of sulcardine, characterized by an XRPD pattern comprising peaks at approximately 15.7, 16.9, and 23.6° 2θ. In some embodiments, the XRPD pattern further comprises peaks at approximately 5.2, 9.1, and 11.3° 2θ. In some embodiments, the XRPD pattern further comprises peaks at approximately 17.6 and 19.2° 2θ. In some embodiments, the XRPD pattern comprises peaks at approximately 5.2, 9.1, 10.2, 10.8, 11.3, 11.9, 13.6, 15.7, 16.9, 17.6, 18.6, 19.2, 20.7, 21.3, and 23.6° 2θ.

In some embodiments, provided herein is a solid form comprising an ethane-1,2-disulfonic acid salt of sulcardine, characterized by an XRPD pattern that matches the XRPD pattern presented in FIG. 28.

In some embodiments, the XRPD patterns are obtained using Cu Kα radiation.

Figure 29:
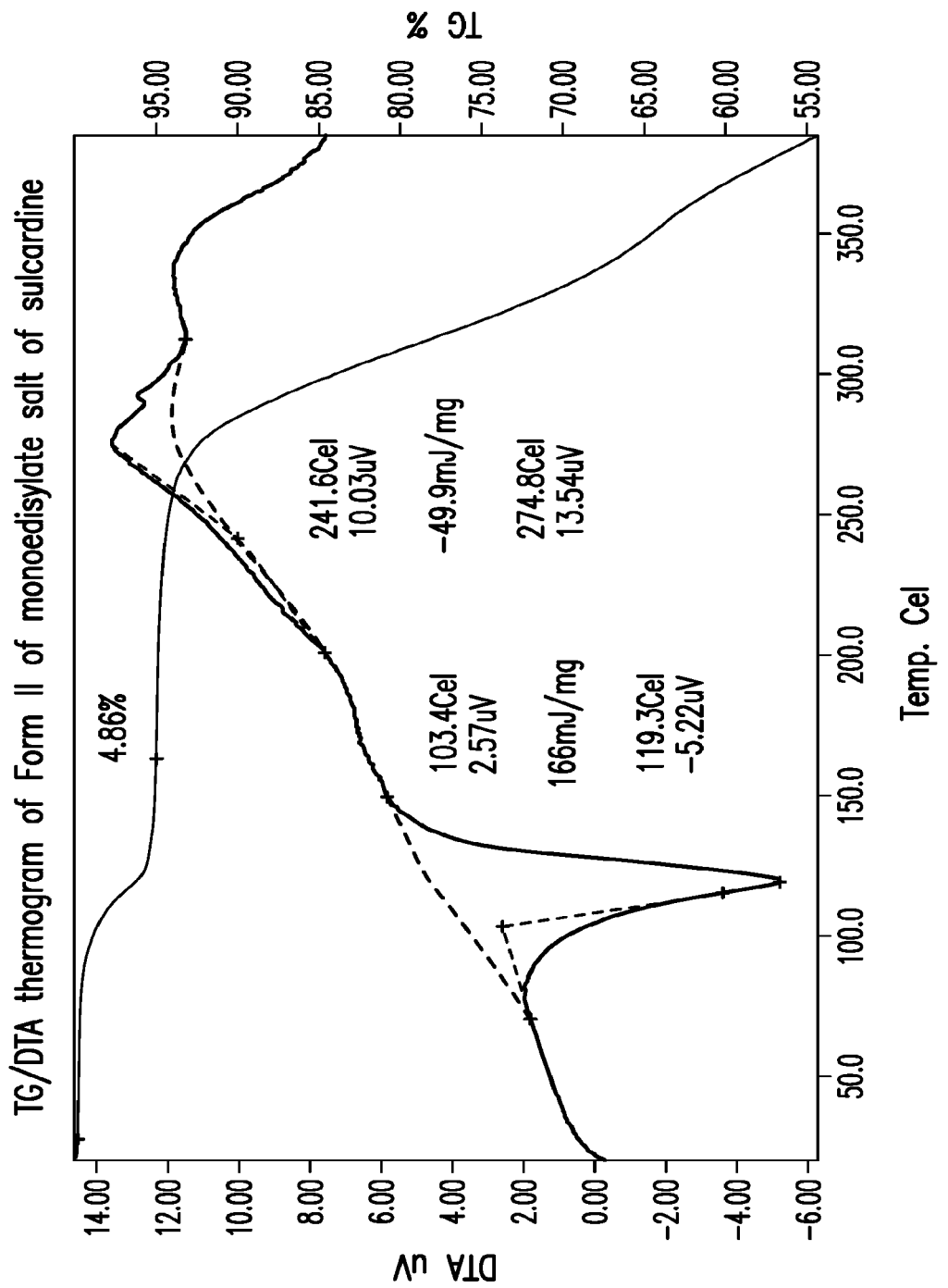
FIG. 29 is a representative TG/DTA thermogram of Form II of monoedisylate salt of sulcardine.

Representative TG/DTA thermograms of Form II of a monoedisylate salt of sulcardine are provided in FIG. 29. In some embodiments, provided herein is a solid form comprising an ethane-1,2-disulfonic acid salt of sulcardine, which exhibits a weight loss of about 4.9% upon heating from about 100° C. to about 150° C. In some embodiments, without being limited by any particular theory, the weight loss corresponds to the loss of about 2 equivalent of water. In some embodiments, provided herein is a solid form comprising an ethane-1,2-disulfonic acid salt of sulcardine, characterized by a TG thermogram that matches the TG thermogram presented in FIG. 29.

In some embodiments, provided herein is a solid form comprising an ethane-1,2-disulfonic acid salt of sulcardine, which exhibits, as characterized by DTA, a first thermal event with an onset temperature of about 103° C., and a second thermal event with an onset temperature of about 242° C. In some embodiments, the first thermal event also has a peak temperature of about 119° C., and the second thermal event also has a peak temperature of about 275° C. In some embodiments, without being limited by any particular theory, the first thermal event corresponds dehydration, and the second thermal event corresponds to the degradation of the solid form. In some embodiments, provided herein is a solid form comprising an ethane-1,2-disulfonic acid salt of sulcardine, characterized by a DTA thermogram that matches the DTA thermogram presented in FIG. 29.

A representative FT-IR spectrum of Form II of a monoedisylate salt of sulcardine is provided in FIG. 37B. In some embodiments, provided herein is a solid form comprising an ethane-1,2-disulfonic acid salt of sulcardine, characterized by a FT-IR spectrum comprising no peak above about 3500 cm$^{-1}$. In some embodiments, provided herein is a solid form comprising an ethane-1,2-disulfonic acid salt of sulcardine, characterized by a FT-IR spectrum comprising one or more peaks at approximately 3374 and 826 cm$^{-1}$. In some embodiments, the FT-IR spectrum comprising a peak at approximately 3374 cm$^{-1}$. In some embodiments, the FT-IR spectrum comprising a peak at approximately 826 cm$^{-1}$. In some embodiments, the FT-IR spectrum comprises the following approximate peaks:

| Peak Shift (cm$^{-1}$) | Relative Intensity |
| --- | --- |
| 3374 | 522.68 |
| 3236 | 74.45 |
| 3061 | 505.65 |
| 2671 | 1825.82 |
| 1650 | 23.22 |
| 1595 | 12.78 |
| 1578 | 7.55 |
| 1495 | 12.76 |
| 1453 | 49.22 |
| 1423 | 313.08 |
| 1323 | 17.45 |
| 1298 | 160.55 |
| 1259 | 11.46 |
| 1226 | 10.72 |
| 1181 | 19.42 |
| 1149 | 74.56 |
| 1107 | 24.63 |
| 1094 | 79.44 |
| 1080 | 92.85 |
| 1056 | 205.98 |
| 1027 | 33.93 |
| 920 | 9.90 |
| 894 | 2273.93 |
| 881 | 23.72 |
| 850 | 9.73 |
| 826 | 13.48 |
| 799 | 887.71 |
| 767 | 14.45 |
| 715 | 428.00 |
| 666 | 11.35 |
| 604 | 310.95 |
| 541 | 87.23 |
| 527 | 34.14 |
| 489 | 282.63 |
| 409 | 16.33 |

In some embodiments, provided herein is a solid form comprising an ethane-1,2-disulfonic acid salt of sulcardine, characterized by a FT-IR spectrum that matches the FT-IR spectrum presented in FIG. 37B.

In some embodiments, provided herein is a solid form comprising an ethane-1,2-disulfonic acid salt of sulcardine, characterized by both an XRPD pattern and a FT-IR spectrum provided in this section. For example, in some embodiments, the solid form is characterized by an XRPD pattern comprising peaks at approximately 15.7, 16.9, and 23.6° 2θ, and is characterized by a FT-IR spectrum comprising no peak above 3500 cm$^{-1}$.

In some embodiments, Form II of monoedisylate salt of sulcardine is prepared by subjecting a mixture of sulcardine and ethane-1,2-disulfonic acid (e.g., about 1:1 molar ratio) in a solvent to a temperature cycle (e.g., between about ambient temperature and about 40° C.) for a period of time (e.g., about 96 hours, or at least 96 hours). In some embodiments, the solvent is toluene.

In some embodiments, Form II of monoedisylate salt of sulcardine is prepared by slurrying Form I of monoedisylate salt of sulcardine (including a mixture comprising Form I of monoedisylate salt of sulcardine) in a mixture of ethanol and water for a period of time (e.g., about 120 hours).

Figure 31:
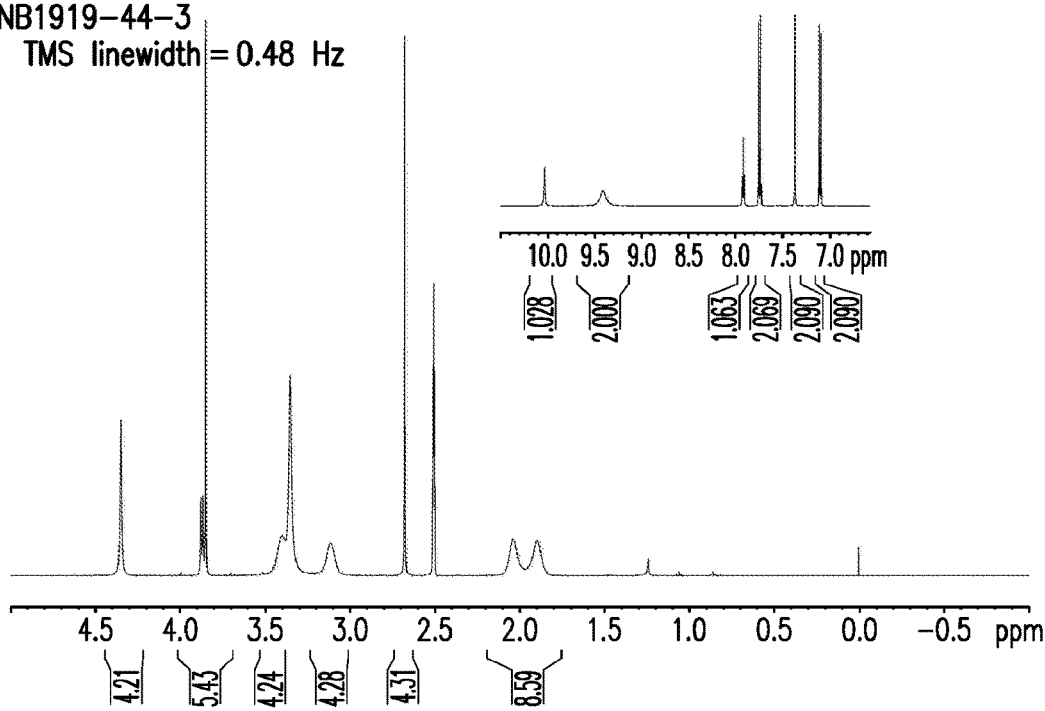
FIG. 31 is a representative $^1$H-NMR spectrum of Form II of monoedisylate salt of sulcardine.

Form II crystalline monoedisylate sulcardine is a higher hydrate than Form I and may be characterized by an XRPD pattern having a peak at about 5.2°2Θ. Form II crystalline monoedisylate sulcardine may also be characterized by an XRPD pattern comprising one or more peaks at about 5.2°2Θ, about 9.1°2Θ, about 10.2°2Θ, about 10.8°2Θ, about 11.3°2Θ, about 13.6°2Θ, and about 15.7°2Θ. An XPRD pattern substantially the same as that of FIG. 28 may also be used to characterize Form II crystalline monoedisylate sulcardine. $^1$H-NMR spectroscopy may be used to confirm a 1:1 stoichiometry of ethane-1,2-disulfonic acid to sulcardine (see FIG. 31).

Form II crystalline monoedisylate sulcardine may be characterized by an XRPD pattern having a peak at about 5.2°2Θ, and an FT-IR spectrum comprising no peak above about 3500 cm$^{-1}$, and further optionally comprising one or more peaks at about 3374 cm$^{-1}$ and about 826 cm$^{-1}$. In some embodiments, Form II crystalline monoedisylate sulcardine may be characterized by an XRPD pattern comprising one or more peaks at about 5.2°2Θ, about 9.1° 2Θ, about 10.2° 2Θ, about 10.8°2Θ, about 11.3°2Θ, about 13.6°2Θ, and about 15.7°2Θ, and an FT-IR spectrum comprising no peak above about 3500 cm$^{-1}$, and further optionally comprising one or more peaks at about 3374 cm$^{-1}$ and about 826 cm$^{-1}$.

A TG/DTA thermogram of Form II of crystalline monoedisylate salt of sulcardine is shown in FIG. 29. This figure shows a mass loss of about 4.9% from about 100° C. to about 150° C. which corresponds to about 2 equivalents of water. Karl Fisher analysis of Form II showed a water content of 5%, or approximately 2 equivalents of water. This is consistent with the TG data which showed a mass loss of approximately 4.9% equating to 2 equivalents of water. Thus, Form II is a dihydrate. A peak list corresponding to many of the peaks in FIG. 28 appear in Table 11C below.

TABLE 11C

XRPD Peak Table Corresponding to FIG. 28

| Position (°2θ) | d-spacing (Å) | Height (counts) | Relative Intensity (%) |
| --- | --- | --- | --- |
| 5.22 | 16.92 | 626.89 | 51.50 |
| 9.06 | 9.76 | 681.27 | 55.97 |
| 10.20 | 8.67 | 109.66 | 9.01 |
| 10.81 | 8.19 | 324.50 | 26.66 |
| 11.27 | 7.85 | 572.37 | 47.03 |
| 11.55 | 7.66 | 27.19 | 2.23 |
| 11.93 | 7.42 | 200.22 | 16.45 |
| 12.86 | 6.89 | 68.38 | 5.62 |
| 13.63 | 6.50 | 334.09 | 27.45 |
| 14.80 | 5.99 | 213.77 | 17.56 |
| 15.25 | 5.81 | 282.83 | 23.24 |
| 15.72 | 5.64 | 1157.68 | 95.11 |
| 16.03 | 5.53 | 82.77 | 6.80 |
| 16.43 | 5.40 | 294.20 | 24.17 |
| 16.90 | 5.25 | 1169.96 | 96.12 |
| 17.65 | 5.03 | 862.29 | 70.84 |
| 18.17 | 4.88 | 226.04 | 18.57 |
| 18.63 | 4.76 | 954.64 | 78.43 |
| 19.19 | 4.63 | 1071.81 | 88.06 |
| 19.41 | 4.57 | 631.85 | 51.91 |
| 20.37 | 4.36 | 569.13 | 46.76 |
| 20.55 | 4.32 | 834.23 | 68.54 |
| 20.72 | 4.29 | 901.63 | 74.08 |
| 21.02 | 4.23 | 218.90 | 17.98 |
| 21.29 | 4.17 | 866.71 | 71.21 |
| 21.85 | 4.07 | 327.62 | 26.92 |
| 22.37 | 3.97 | 132.49 | 10.88 |
| 22.75 | 3.91 | 567.46 | 46.62 |
| 23.57 | 3.77 | 1217.17 | 100.00 |
| 23.98 | 3.71 | 227.83 | 18.72 |
| 24.47 | 3.64 | 165.02 | 13.56 |
| 25.14 | 3.54 | 262.59 | 21.57 |
| 25.41 | 3.51 | 200.31 | 16.46 |
| 25.67 | 3.47 | 594.26 | 48.82 |
| 26.20 | 3.40 | 266.78 | 21.92 |
| 26.64 | 3.35 | 29.00 | 2.38 |
| 27.14 | 3.29 | 350.89 | 28.83 |
| 27.42 | 3.25 | 100.31 | 8.24 |
| 28.30 | 3.15 | 224.81 | 18.47 |
| 29.26 | 3.05 | 172.82 | 14.20 |
| 29.86 | 2.99 | 105.40 | 8.66 |
| 30.30 | 2.95 | 156.11 | 12.83 |
| 30.82 | 2.90 | 55.74 | 4.58 |
| 31.33 | 2.85 | 136.59 | 11.22 |
| 31.95 | 2.80 | 93.08 | 7.65 |
| 32.63 | 2.74 | 117.42 | 9.65 |
| 33.30 | 2.69 | 38.69 | 3.18 |
| 33.92 | 2.64 | 56.32 | 4.63 |
| 34.34 | 2.61 | 35.17 | 2.89 |
| 34.56 | 2.59 | 40.07 | 3.29 |

The XRPD pattern of Form II of crystalline monoedisylate salt of sulcardine is not a linear combination of the XRPD patterns of ethane-1,2-disulfonic acid and amorphous sulcardine free base. For example, Form II of crystalline monoedisylate salt of sulcardine has a peak at about 5.2°2Θ which is not present in the free acid XRPD pattern of FIG. 22, and amorphous sulcardine has no peaks. The XRPD pattern of FIG. 28 is not a physical mixture of the salt starting materials.

Thermodynamic solubility data of Form II of monoedisylate salt of sulcardine are provided in Table 14 of Example 25.

All of the combinations of the above embodiments are encompassed by this application.

10. Sulcardine Hydrobromide Salt

In certain embodiments, provided herein is a sulcardine hydrobromide salt. In some embodiments, the salt is crystalline.

In some embodiments, the molar ratio of sulcardine to hydrobromic acid in the salt is about 1:1. In some embodiments, the salt is a mono-hydrobromide salt of sulcardine.

Figure 23:
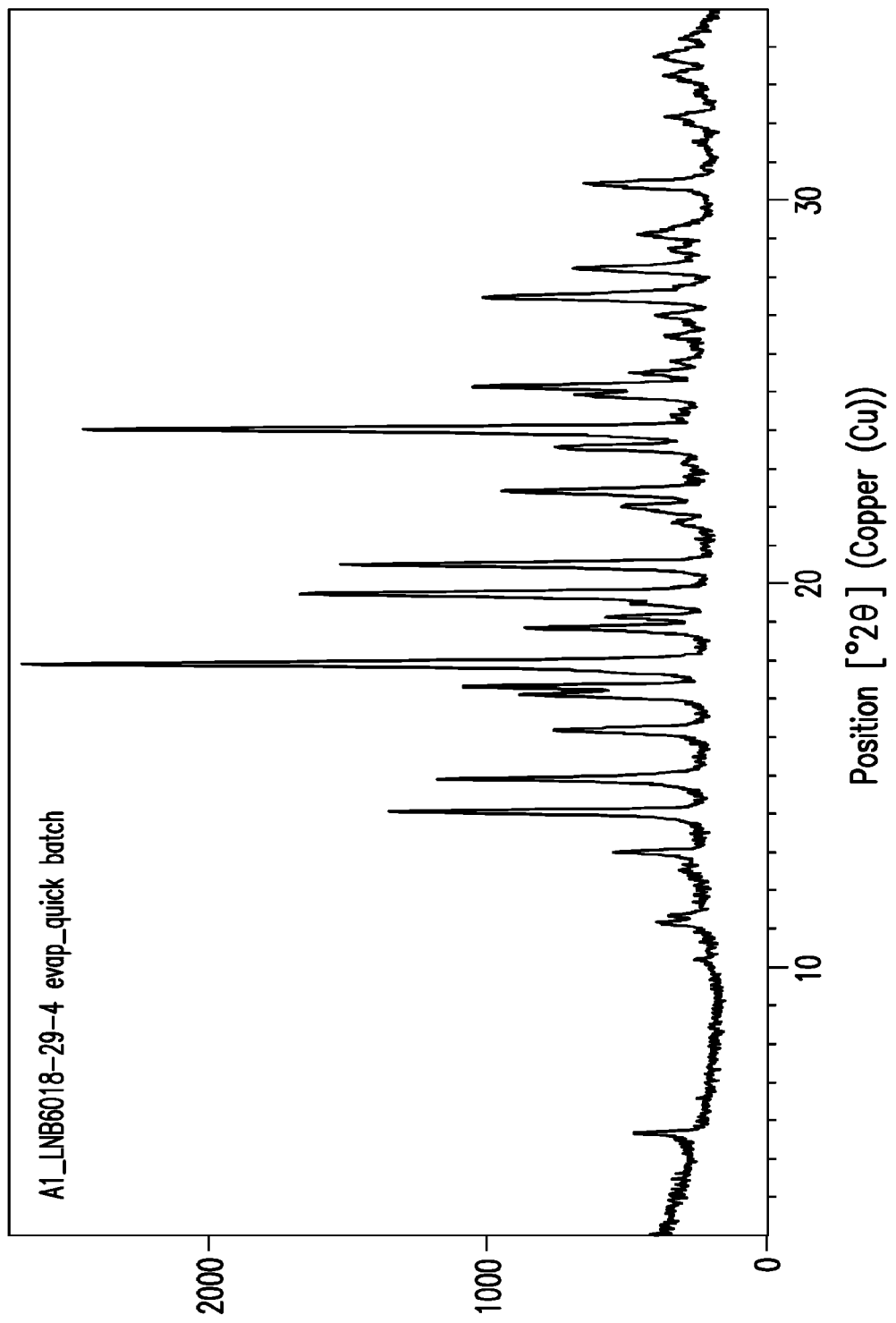
FIG. 23 is a representative XRPD pattern of a crystalline salt of sulcardine and hydrobromic acid.

A representative XRPD pattern of a sulcardine hydrobromide salt is provided in FIG. 23.

In some embodiments, provided herein is a solid form comprising a sulcardine hydrobromide salt, characterized by 1, 2, 3, 4, 5, 6, 7, 8, 9, 10, 11, 12, 13, 14, 15, 16, 17, 18, 19, 20, 21, or all of the peaks located at approximately the following positions: 5.7, 13.0, 14.1, 14.9, 16.2, 17.1, 17.3, 17.9, 18.8, 19.1, 19.7, 20.5, 22.0, 22.4, 23.6, 24.0, 24.9, 25.1, 25.5, 27.5, 28.2, and 30.4° 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by all of the peaks.

In some embodiments, provided herein is a solid form comprising a sulcardine hydrobromide salt, characterized by an XRPD pattern comprising peaks at approximately 17.9, 19.7, and 24.0° 2θ. In some embodiments, the XRPD pattern further comprises peaks at approximately 14.1 and 14.9° 2θ. In some embodiments, the XRPD pattern further comprises peaks at approximately 5.7, 13.0, and 16.2° 2θ. In some embodiments, the XRPD pattern comprises peaks at approximately 5.7, 13.0, 14.1, 14.9, 16.2, 17.1, 17.3, 17.9, 18.8, 19.7, 20.5, and 24.0° 2θ.

In some embodiments, provided herein is a solid form comprising a sulcardine hydrobromide salt, characterized by an XRPD pattern that matches the XRPD pattern presented in FIG. 23.

In some embodiments, the XRPD patterns are obtained using Cu Kα radiation.

Figure 24:
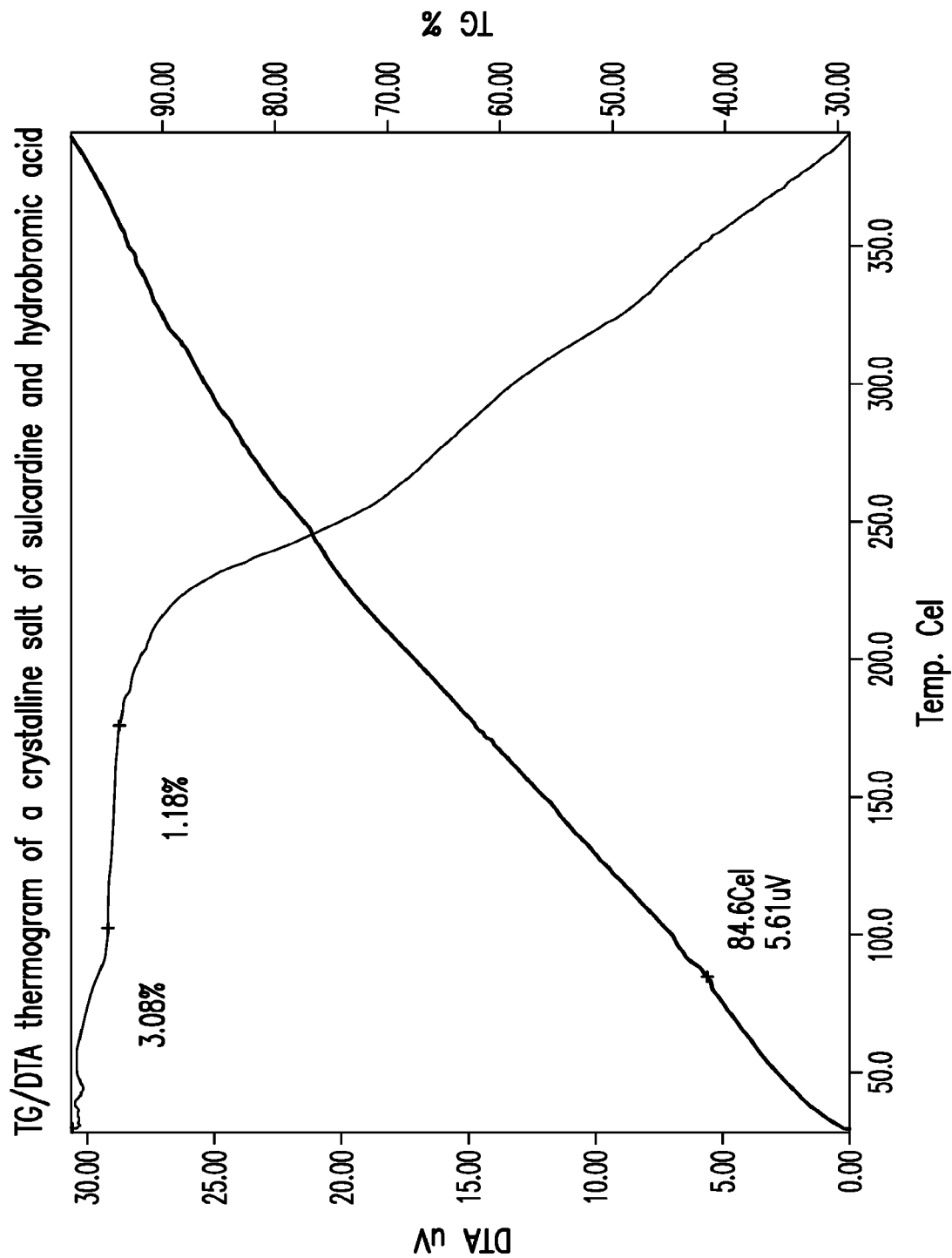
FIG. 24 is a representative TG/DTA thermogram of a crystalline salt of sulcardine and hydrobromic acid.

Representative TG/DTA thermograms of a sulcardine hydrobromide salt are provided in FIG. 24. In some embodiments, provided herein is a solid form comprising a sulcardine hydrobromide salt, which exhibits a weight loss of about 4.3% upon heating from about 25° C. to about 175° C. In some embodiments, provided herein is a solid form comprising a sulcardine hydrobromide salt, characterized by a TG thermogram that matches the TG thermogram presented in FIG. 24.

In some embodiments, provided herein is a solid form comprising a sulcardine hydrobromide salt, characterized by a DTA thermogram that matches the DTA thermogram presented in FIG. 24.

In some embodiments, a sulcardine hydrobromide salt is prepared by subjecting a mixture of sulcardine and hydrobromic acid (e.g., a mixture of 2-propanol and heptane) in a solvent (e.g., TIF) to a temperature cycle (e.g., between ambient temperature and about 40° C.) for a period of time (e.g., about 72 hours). In some embodiments, the solvent is a 2:1 v/v mixture of 2-propanol and heptane.

In other embodiments, crystalline salt of sulcardine and hydrobromic acid are provided. A preparation of a crystalline salt of sulcardine and hydrobromic acid is in Example 15. Such crystalline salts may be characterized by an XRPD pattern comprising one or more peaks chosen from about 5.7°2Θ, about 13.0°2Θ, about 14.1°2Θ, about 14.9°2Θ, and about 16.2°2Θ. An XRPD pattern substantially the same as that of FIG. 23 may also be used to characterize a crystalline salt of sulcardine and hydrobromic acid. A peak list corresponding to many of the peaks in FIG. 23 appears in Table 12.

Because hydrobromic acid is a liquid under the experimental conditions used herein, the solid obtained is not a mixture of hydrobromic acid and amorphous sulcardine free base. The solid is a crystalline salt of sulcardine and hydrobromic acid.

TABLE 12

XRPD Peak Table Corresponding to FIG. 23

| Position (°2Θ) | d-spacing (Å) | Height (counts) | Relative Intensity (%) |
|---|---|---|---|
| 5.67 | 15.59 | 202.55 | 7.95 |
| 10.19 | 8.68 | 75.28 | 2.96 |
| 11.15 | 7.94 | 203.88 | 8.00 |
| 11.35 | 7.80 | 175.10 | 6.87 |
| 13.00 | 6.81 | 381.66 | 14.98 |
| 14.06 | 6.30 | 1205.09 | 47.31 |
| 14.91 | 5.94 | 992.41 | 38.96 |
| 16.18 | 5.48 | 601.35 | 23.61 |
| 17.10 | 5.18 | 725.41 | 28.48 |
| 17.31 | 5.12 | 936.93 | 36.78 |
| 17.90 | 4.96 | 2547.34 | 100.00 |
| 18.84 | 4.71 | 697.93 | 27.40 |
| 19.13 | 4.64 | 390.40 | 15.33 |
| 19.49 | 4.56 | 302.05 | 11.86 |
| 19.73 | 4.50 | 1485.49 | 58.32 |
| 20.50 | 4.33 | 1381.71 | 54.24 |
| 21.59 | 4.12 | 153.90 | 6.04 |
| 22.03 | 4.04 | 344.89 | 13.54 |
| 22.41 | 3.97 | 764.97 | 30.03 |
| 23.56 | 3.78 | 598.26 | 23.49 |
| 24.03 | 3.70 | 2322.47 | 91.17 |
| 24.92 | 3.57 | 524.02 | 20.57 |
| 25.14 | 3.54 | 894.69 | 35.12 |
| 25.49 | 3.49 | 312.98 | 12.29 |
| 25.80 | 3.45 | 167.45 | 6.57 |
| 26.45 | 3.37 | 185.80 | 7.29 |
| 26.99 | 3.30 | 215.09 | 8.44 |
| 27.47 | 3.25 | 858.15 | 33.69 |
| 28.22 | 3.16 | 529.54 | 20.79 |
| 28.70 | 3.11 | 169.95 | 6.67 |
| 29.12 | 3.07 | 268.04 | 10.52 |
| 30.43 | 2.94 | 494.06 | 19.40 |
| 31.50 | 2.84 | 67.06 | 2.63 |
| 32.17 | 2.78 | 167.35 | 6.57 |
| 33.26 | 2.69 | 183.14 | 7.19 |
| 33.76 | 2.65 | 198.30 | 7.78 |
| 34.24 | 2.62 | 131.07 | 5.15 |

Also provided herein are pharmaceutical compositions containing salts of sulcardine, including crystalline salts of sulcardine. Such pharmaceutical compositions comprise one or more pharmaceutically acceptable excipients and a salt, such as a crystalline salt, provided herein. Such pharmaceutical compositions may be administered orally or configured to be delivered as any effective conventional dosage unit forms, including immediate, slow and timed release oral preparations, parenterally, topically, nasally, ophthalmically, optically, sublingually, rectally, vaginally, and the like.

Further provided herein are methods and uses for treating diseases in humans such as arrhythmias, including supraventricular tachyarrhythmia such as atrial fibrillation, premature ventricular contractions, ventricular tachycardia and ventricular fibrillation by administering to humans with effective amounts of sulcardine salts, including crystalline salts, and/or pharmaceutical compositions comprising sulcardine salts, including crystalline salts, provided herein. In some embodiments, the disease is atrial fibrillation.

As used herein and unless otherwise specified, "treat," "treatment," and "treating" refer to an approach for obtaining beneficial or desired results, including, but not limited to, a therapeutic benefit. In some embodiments, therapeutic benefit means eradication or amelioration of the underlying disorder being treated. In some embodiments, a therapeutic benefit is achieved with the eradication or amelioration of one or more of the physiological symptoms associated with the underlying disorder, such that an improvement is observed in the patient, notwithstanding that the patient can still be afflicted with the underlying disorder.

A "subject" of treatment is a prokaryotic or a eukaryotic cell, a tissue culture, a tissue or an animal, e.g., a mammal, including a human. Non-human animals subject to treatment include, for example, a simian, a murine, a canine, a leporid, such as a rabbit, livestock, sport animals, and pets. As used herein and unless otherwise specified, a "patient" is a human subject.

The following numbered embodiments are contemplated and are non-limiting:

Clause 1. A salt of sulcardine and a mononaphthalene salt former.

Clause 2. The salt of clause 1, wherein the mononaphthalene salt former contains one or more sulfonic acid moieties.

Clause 3. The salt of clause 2, wherein the mononaphthalene salt former contains one sulfonic acid moiety.

Clause 4. The salt of clause 2, wherein the mononaphthalene salt former contains two sulfonic acid moieties.

Clause 5. The salt of clause 4, wherein the two sulfonic acid moieties are on the same aromatic ring.

Clause 6. The salt of clause 1, wherein the mononaphthalene salt former is an organic acid.

Clause 7. The salt of clause 6, where the organic acid is a carboxylic acid.

Clause 8. The salt of clause 7, where the salt former is substituted.

Clause 9. The salt of clause 8, where the salt former is substituted with an —OH group.

Clause 10. The salt of clause 8 or 9, wherein the substitution is ortho to the organic acid group.

Clause 11. The salt of clause 4, wherein the two sulfonic acid moieties are on different rings of the naphthalene salt former.

Clause 12. A crystalline salt of sulcardine and a salt former wherein the salt former is not sulfuric acid.

Clause 13. A crystalline salt of sulcardine and a sulfonic acid salt former.

Clause 14. The crystalline salt of clause 13, wherein the sulfonic acid is aromatic and contains one or more sulfonic acid moieties.

Clause 15. The crystalline salt of clause 14, wherein the aromatic sulfonic acid comprises a naphthyl moiety and one or two sulfonic acid moieties.

Clause 16. The crystalline salt of clause 15, wherein the naphthyl moiety is further substituted.

Clause 17. The crystalline salt of clause 16, wherein the substituent is hydroxyl.

Clause 18. The crystalline salt of clause 13, wherein the sulfonic acid is aliphatic and contains one or two sulfonic moieties.

Clause 19. A crystalline salt of sulcardine and inorganic acid other than sulfuric.

Clause 20. A crystalline salt of clause 19 wherein the salt of sulcardine is a halide.

Clause 21. A salt of sulcardine and naphthalene-1,5-disulfonic acid.

Clause 22. A crystalline salt of sulcardine and naphthalene-1,5-disulfonic acid.

Clause 23. The crystalline salt of sulcardine and naphthalene-1,5-disulfonic acid of clause 22, comprising an x-ray powder diffraction peak at about 4.6°2θ.

Clause 24. The crystalline salt of sulcardine and naphthalene-1,5-disulfonic acid of clause 22 or 23, comprising an x-ray powder diffraction pattern comprising one or more peaks chosen from about 4.9°2θ, about 10.4°2θ, about 11.7°2θ, about 12.3°2θ, and about 15.9°2θ.

Clause 25. The crystalline salt of sulcardine and naphthalene-1,5-disulfonic acid of any one of clauses 22-24, having a melting onset temperature of about 244° C.

Clause 26. The crystalline salt of sulcardine and naphthalene-1,5-disulfonic acid of clause 22, having an x-ray powder diffraction pattern substantially the same as that of FIG. 1.

Clause 27. The crystalline salt of sulcardine and naphthalene-1,5-disulfonic acid of clause 26, having a melting onset of about 244° C.

Clause 28. Form II of a crystalline salt of sulcardine and hydrochloric acid.

Clause 29. A salt of sulcardine and 1-hydroxy-2-naphthoic acid.

Clause 30. A crystalline salt of sulcardine and 1-hydroxy-2-naphthoic acid.

Clause 31. Form I of a crystalline salt of sulcardine and 1-hydroxy-2-naphthoic acid.

Clause 32. The crystalline salt of sulcardine and 1-hydroxy-2-naphthoic acid of clause 31, having an x-ray powder diffraction pattern comprising one or more peaks chosen from about 3.4°2, about 6.7 2θ, about 6.9°2θ, and about 15.4°2θ.

Clause 33. The crystalline salt of sulcardine and 1-hydroxy-2-naphthoic acid of clause 31, having an x-ray powder diffraction pattern comprising one or more peaks chosen from about 3.4°2θ, about 6.7 2θ, and about 6.9°2θ.

Clause 34. The crystalline salt of sulcardine and 1-hydroxy-2-naphthoic acid of clause 31, having an x-ray powder diffraction pattern comprising peaks chosen from about 3.4°2θ and two peaks between about 6.5°2θ and about 7.1°2θ.

Clause 35. The crystalline salt of sulcardine and 1-hydroxy-2-naphthoic acid of any one of clauses 31-34, having a melting onset temperature of about 161° C.

Clause 36. The crystalline salt of sulcardine and 1-hydroxy-2-naphthoic acid of clauses 29, 30, or 31, having an x-ray powder diffraction pattern substantially the same as that of FIG. 6.

Clause 37. Form II of a crystalline salt of sulcardine and 1-hydroxy-2-naphthoic acid.

Clause 38. The crystalline salt of clause 28, having substantially the same XRPD pattern as FIG. 17A.

Clause 39. The crystalline salt of sulcardine and 1-hydroxy-2-naphthoic acid of clause 37, having an x-ray powder diffraction pattern comprising one or more peaks chosen from about 5.8°2θ and about 8.8°2θ.

Clause 40. Form I of a crystalline salt of sulcardine and hydrochloric acid.

Clause 41. The crystalline salt of clause 28, having an x-ray powder diffraction pattern comprising one or more peaks chosen from about 10.1°2θ, about 11.8°2θ, about 13.5°2θ, and about 16.4°2θ.

Clause 42. The crystalline salt of clause 28, having an x-ray powder diffraction pattern wherein there is no peak below about 9.5°2θ and no peaks between the peaks at about 10.1°2θ and about 11.8°2θ.

Clause 43. The crystalline salt of sulcardine and 1-hydroxy-2-naphthoic acid of clause 37, having a melting onset temperature of about 168° C.

Clause 44. The crystalline salt of sulcardine and 1-hydroxy-2-naphthoic acid of clauses 37 or 43, having an x-ray powder diffraction pattern substantially the same as that of FIG. 9.

Clause 45. A salt of sulcardine and naphthalene-2-sulfonic acid.

Clause 46. A crystalline salt of sulcardine and naphthalene-2-sulfonic acid.

Clause 47. The crystalline salt of sulcardine and naphthalene-2-sulfonic acid of clause 46, having an x-ray powder diffraction pattern comprising one or more peaks chosen from about 9.4°2θ, about 10.6°2θ, about 13.3°2θ, about 13.5°2θ, about 16.6°2θ, about 16.9°2θ, and about 17.2°2θ.

Clause 48. The crystalline salt of sulcardine and naphthalene-2-sulfonic acid of clause 46, having an x-ray powder diffraction pattern comprising one or more peaks chosen from about 9.4°2θ, about 10.6°2θ, about 13.3°2θ, and about 13.5°2θ.

Clause 49. The crystalline salt of sulcardine and naphthalene-2-sulfonic acid of clause 46, having an x-ray powder diffraction pattern comprising peaks chosen from about 9.4°2θ, about 10.6°2θ, and about 13.5°2θ.

Clause 50. The crystalline salt of sulcardine and naphthalene-2-sulfonic acid of clause 46, having an x-ray powder diffraction pattern comprising two peaks between about 13.1°2θ and about 13.7°2θ and three peaks between about 16.4°2θ and about 17.4°2θ.

Clause 51. The crystalline salt of sulcardine and naphthalene-2-sulfonic acid of any one of clauses 46-50, having a melting onset temperature of about 88° C.

Clause 52. The crystalline salt of sulcardine and naphthalene-2-sulfonic acid of clauses 46 or 51, having an x-ray powder diffraction pattern substantially the same as that of FIG. 13.

Clause 53. A salt of sulcardine and hydrochloride.

Clause 54. A crystalline salt of sulcardine and hydrochloride.

Clause 55. The crystalline salt of sulcardine hydrochloride of clause 40, having an x-ray powder diffraction pattern comprising one or more peaks chosen from about 12.3°2θ, and about 13.0°2θ.

Clause 56. The crystalline salt of sulcardine hydrochloride of clause 54 or 55, having substantially the same x-ray powder diffraction pattern as FIG. 17.

Clause 57. A salt of sulcardine and ethane-1,2-disulfonic acid.

Clause 58. A crystalline salt of sulcardine and ethane-1,2-disulfonic acid.

Clause 59. The crystalline salt of sulcardine and ethane-1,2-disulfonic acid of clause 58, having an x-ray powder diffraction pattern comprising one or more peaks chosen from about 5.6°2θ, about 11.0°2θ, about 13.0°2θ, about 14.1°2θ, and about 14.9°2θ.

Clause 60. The crystalline salt of sulcardine and ethane-1,2-disulfonic acid of clause 58, having substantially the same x-ray powder diffraction pattern as FIG. 19.

Clause 61. The crystalline salt of sulcardine and ethane-1,2-disulfonic acid of any one of clauses 58-60, having a melting onset temperature of about 211° C.

Clause 62. A salt of sulcardine and hydrobromic acid.

Clause 63. A crystalline salt of sulcardine and hydrobromic acid.

Clause 64. The crystalline salt of sulcardine and hydrobromic acid of clause 63, having an x-ray powder diffraction pattern comprising one or more peaks chosen from about 5.7°2Θ, about 13.0°2Θ, about 14.1°2Θ, about 14.9°2Θ, and about 16.2°2Θ.

Clause 65. The crystalline salt of sulcardine and hydrobromic acid of clause 63, having substantially the same x-ray powder diffraction pattern as FIG. 23.

Clause 66. A salt of sulcardine and a salt former selected from naphthalene-1,5-disulfonic acid, 1-hydroxy-2-naphthoic acid, naphthalene-2-sulfonic acid, hydrochloric acid, ethane-1,2-disulfonic acid, or hydrobromic acid.

Clause 67. A crystalline salt of sulcardine and a salt former selected from naphthalene-1,5-disulfonic acid, 1-hydroxy-2-naphthoic acid, naphthalene-2-sulfonic acid, hydrochloric acid, or hydrobromic acid.

Clause 68. A pharmaceutical composition comprising a sulcardine salt composition of any one of clauses 1-67 or 72-88 and one or more pharmaceutically acceptable excipients.

Clause 69. A method of treating arrhythmia with a pharmaceutically effective amount of a pharmaceutical composition of clause 68, comprising administering such a composition to a patient in need thereof.

Clause 70. A method of treating arrhythmia with a pharmaceutically effective amount of a sulcardine salt of any one of clauses 1-67 or 72-88 comprising administering such a salt to a patient in need thereof.

Clause 71. The method of clause 69 or 70, wherein the arrhythmia is selected from supraventricular tachyarrhythmia, premature ventricular contractions, ventricular tachycardia and ventricular fibrillation.

Clause 72. The salt of any one of clauses 45 to 52, wherein the salt is a hydrate.

Clause 73. Form I of a crystalline salt of clause 54, wherein there is no peak below about 9.5°2Θ.

Clause 74. The salt of any one of clauses 53 to 56, wherein the salt is a hydrate.

Clause 75. The crystalline salt of clause 31, having an x-ray powder diffraction pattern comprising a peak at about 3.4°2Θ.

Clause 76. A monoedisylate salt of sulcardine.

Clause 77. A crystalline sulcardine salt of clause 76.

Clause 78. Form I of crystalline monoedisylate salt of sulcardine.

Clause 79. A monohydrate of crystalline monoedisylate salt of sulcardine.

Clause 80. The crystalline monoedisylate salt of sulcardine of any one of clauses 76-79, having an x-ray powder diffraction pattern comprising a peak at about 14.2°2Θ.

Clause 81. The crystalline monoedisylate of any one of clauses 76-79, comprising one or more peaks selected from about 9.2°2Θ, about 9.6°2Θ, about 10.4°2Θ, about 13.8°2Θ, about 14.2°2Θ, and about 14.9°2Θ.

Clause 82. Form II of crystalline monoedisylate salt of sulcardine.

Clause 83. A hydrate of crystalline monoedisylate salt of sulcardine.

Clause 84. A dihydrate of crystalline monoedisylate salt of sulcardine.

Clause 85. The crystalline monoedisylate salt of sulcardine of any one of clauses 82-84, having an x-ray powder diffraction pattern comprising a peak at about 5.2°2Θ.

Clause 86. The crystalline monoedisylate salt of sulcardine of any one of clauses 82-84, comprising one or more peaks selected from about 5.2°2θ, about 9.1°2θ, about 10.2°2Θ, about 10.8°2, about 11.3°2θ, and about 13.6°2θ.

Clause 87. A hydrate of clause 76.

Clause 88. A hydrate of clause 87, wherein the molar hydration is greater than 1.

EXAMPLES

Example 1—Methods of Analysis

XRPD analysis was carried out on a PANalytical X'pert pro with PIXcel detector (128 channels), scanning the samples between 3 and 35° 2θ. The material was loaded onto a multi-well plate with Mylar polymer film to support the sample. The multi-well plate was then placed into the diffractometer and analysed using Cu K radiation ($\alpha_1$ λ=1.54060 Å; $\alpha_2$=1.54443 Å; β=1.39225 Å; $\alpha_1$:$\alpha_2$ ratio=0.5) running in transmission mode (step size 0.013° 2θ, step time 18.87 s) using 40 kV/40 mA generator settings. Data were visualized and images generated using the High-Score Plus 4.7 desktop application (PANalytical, 2017).

Approximately 5 mg of material was weighed into an open aluminium pan and loaded into a simultaneous thermogravimetric/differential thermal analyser (TG/DTA) and held at room temperature. The sample was then heated at a rate of 10° C./min from 20° C. to 400° C. during which time the change in sample weight was recorded along with any differential thermal events (DTA). Nitrogen was used as the purge gas, at a flow rate of 300 $cm^3$/min.

$^1$H-NMR experiments were performed on a Bruker AVIIIHD spectrometer equipped with a DCH cryoprobe operating at 500.12 MHz for protons. Experiments were performed in deuterated DMSO and each sample was prepared to ca. 10 mM concentration. The pH of solutions was measured using a Hanna H12210 pH meter with microelectrode operating between pH −2 and 16.

HPLC analysis was performed on a Dionex Ultimate 3000 instrument with the following parameters:
Column: Phenomenex Luna C18, 150×4.6 mm, 5 μm
Column Temperature: 30° C.
Mobile Phase A: 0.2% Phosphoric Acid
Mobile Phase B: Methanol
Diluent: 50:50 MeOH:$H_2O$
Runtime: 12 minutes
Flow Rate: 1.0 mL/min
Injection Volume: 5 μL
Detection: 237 nm
Gradient:

| Time (mins) | Solvent B (%) |
| --- | --- |
| 0.00 | 10 |
| 1.50 | 10 |
| 9.0 | 85 |
| 10.50 | 85 |
| 10.51 | 10 |
| 12.0 | 10 |

Example 2—Preparation of Free Base and Screening

Figure 4:
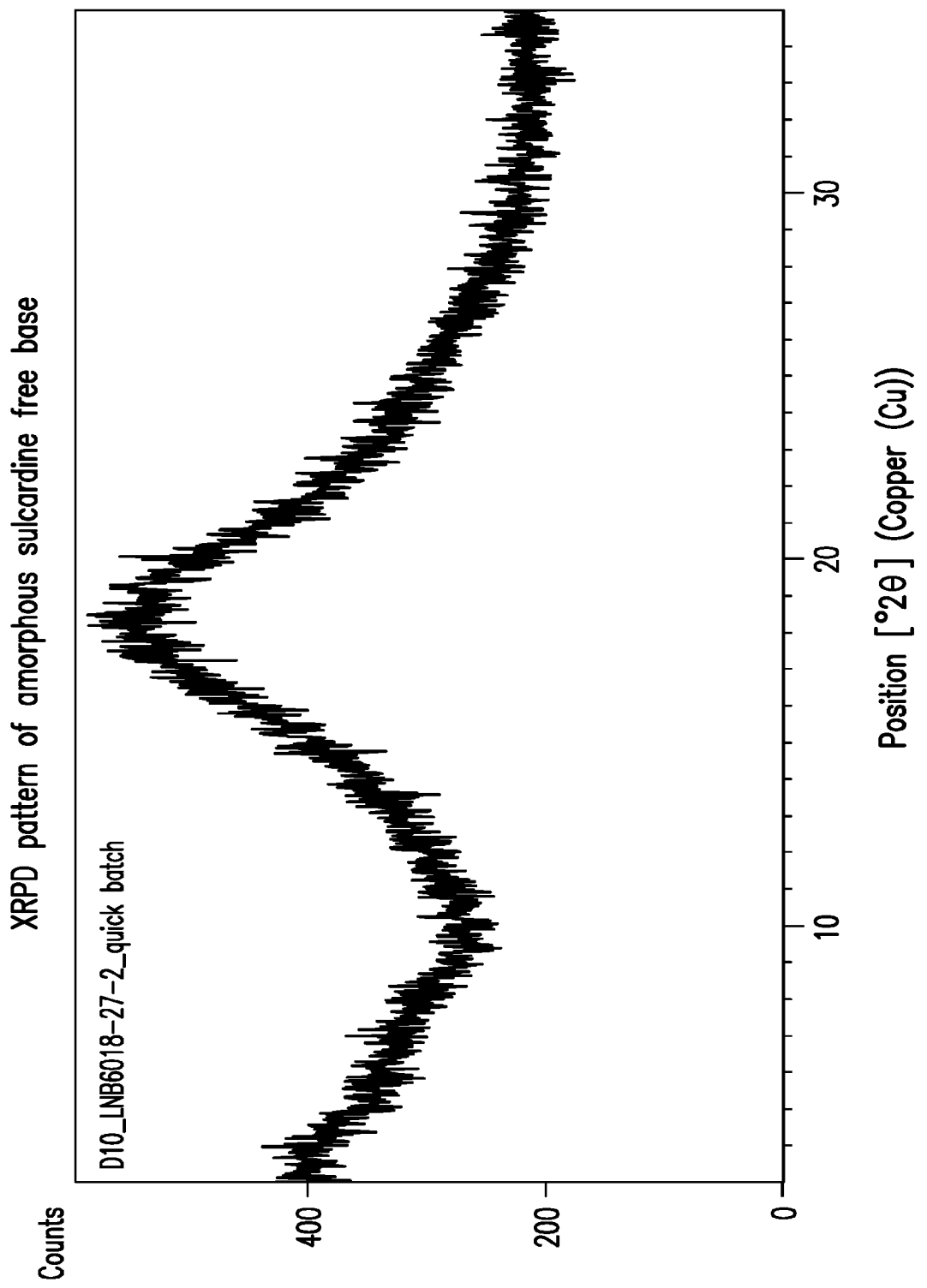
FIG. 4 is a representative XRPD pattern of amorphous sulcardine free base.

Sulcardine sulfate trihydrate was dissolved in ethyl acetate (16 vol.) and saturated sodium bicarbonate solution (16 vol.). The biphasic solution was transferred to a separating funnel and the layers separated. The organic layer was dried over sodium sulfate and then the solvent was removed by rotary evaporation and the resulting oil dried under vacuum at ambient temperature for ca. 3 hr. FIG. 4 is an XRPD pattern of the resulted amorphous sulcardine free base. In all cases, the initial screening work detailed below was performed on 10 mg of sulcardine free base. All XRPD diffractograms were compared with sulcardine sulfate trihydrate, sulcardine free base and relevant counterions and found to be distinct.

Example 3—Solubility 20 mM buffers were prepared to pH 1.2 (HCl/KCl), pH 3.0 (HCl/glycine), pH 4.0 (citric acid/sodium citrate) and pH 7.4 (potassium phosphate monobasic/NaOH). To 0.5 mL of each buffer, the appropriate salt was added to form a slurry. The pH of the slurry was measured and adjusted back to the desired pH (i.e., the initial pH of the buffer) if necessary using 0.2 M buffer components (e.g. 0.2 M $HCl_{(aq)}$). The samples were slurried at ambient temperature for ca. 72 hr.

After this time, if solid remained, the pH was again adjusted back to the desired pH if necessary using 0.2 M buffer components. If no solid remained, additional solid was added to reform the slurry before the pH was again adjusted back to the desired pH if necessary using 0.2 M buffer components. All samples were then slurried for a further 2 hr before being analysed by HPLC for concentration.

Example 4—Naphthalene-1,5-Disulfonic Acid Salt

To sulcardine free base was added naphthalene-1,5-disulfonic acid (1.05 eq.) and acetone (20 vol.). The sample was temperature cycled between ambient temperature and 40° C. in 4 hr cycles for ca. 72 hr, leaving a white and orange solid.

The material was crystalline by XRPD. There was a 2.9% mass loss in the TG up to decomposition and a melting event in the DTA with an onset temperature of 243° C. Naphthalene-1,5-disulfonic acid (1.0 eq.) was observed in the $^1$H-NMR and no significant solvent was observed. The solubility was 1.6 mg·mL-1 in pH 1.2 buffer, 0.7 mg·mL-1 in pH 3.0 buffer, 1.0 mg·mL-1 in pH 4.0 buffer and 6.9 mg·mL$^{-1}$ in pH 7.4 buffer (Table 3).

Example 5—Naphthalene-1,5-Disulfonic Acid Salt Scale-Up

Figure 3:
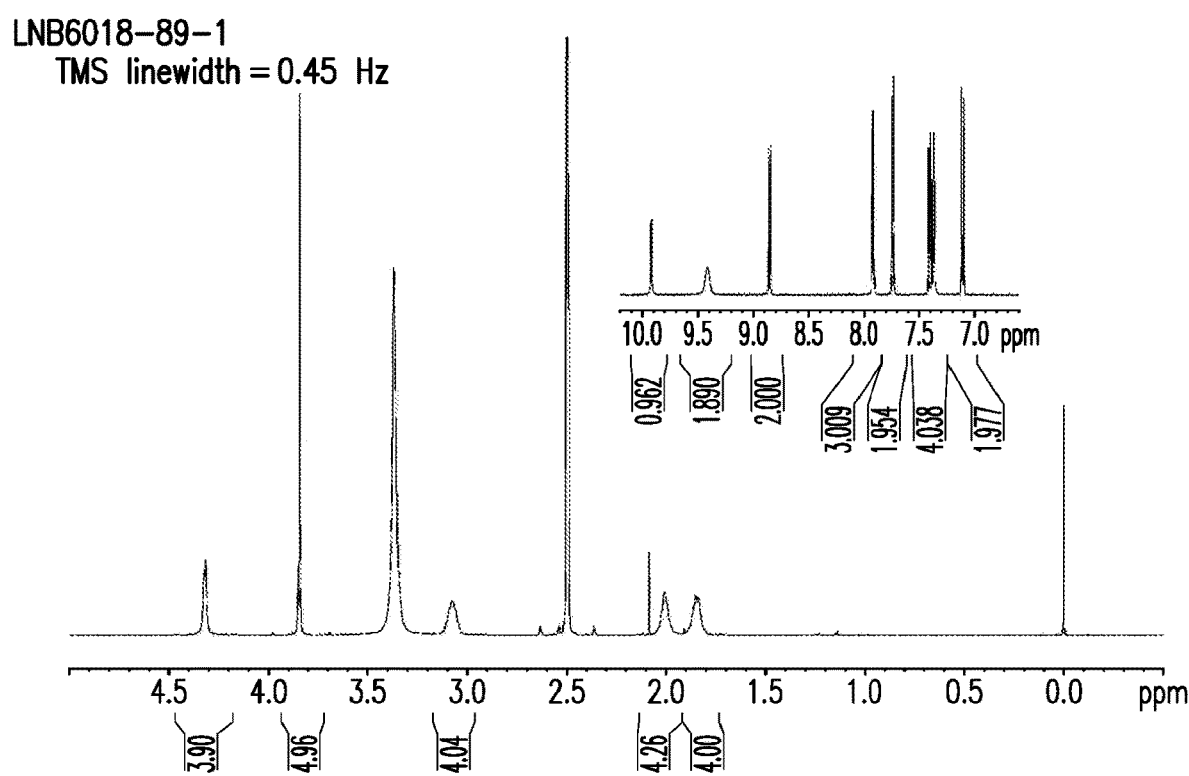
FIG. 3 is a representative $^{1}$H-NMR spectrum of a crystalline salt of sulcardine and naphthalene-1,5-disulfonic acid.

To sulcardine free base (200 mg), 2 mL of acetone and 169.8 mg of naphthalene-1,5-disulfonic acid (1.05 eq.) were added. The sample was temperature cycled in accordance with Example 16. The resulting solid was filtered using a Buchner funnel and filter dried for about 15 minutes. FIG. 1 shows the XRPD pattern from this Example. FIG. 1 is the XRPD pattern of this salt, which indicates it is crystalline. A peak table is in Table 2. There was no mass loss in the TG up until decomposition and a melting event in the DTA with an onset temperature of 244° C. (FIG. 2). Naphthalene-1,5-disulfonic acid was observed in the H-NMR at 1:1 and no significant solvent was observed (FIG. 3). The solubility was measured to be 1.6 mg·mL-1 in pH 1.2 buffer, 0.7 mg·mL-1 in pH 3.0 buffer, 1.0 mg·mL-1 in pH 4.0 buffer and 6.9 mg·mL$^{-1}$ in pH 7.4 buffer (Table 3).

Example 6—1-Hydroxy-2-Naphthoic Acid Salt Form I

To sulcardine free base was added 1M 1-hydroxy-2-naphthoic acid stock solution in THE (1.05 eq.) and ethyl acetate (20 vol.). The sample was temperature cycled between ambient temperature and 40° C. in 4 hr cycles for ca. 72 hr and then placed in a fridge for ca. 24 hr, leaving a brown solid.

Figure 8:
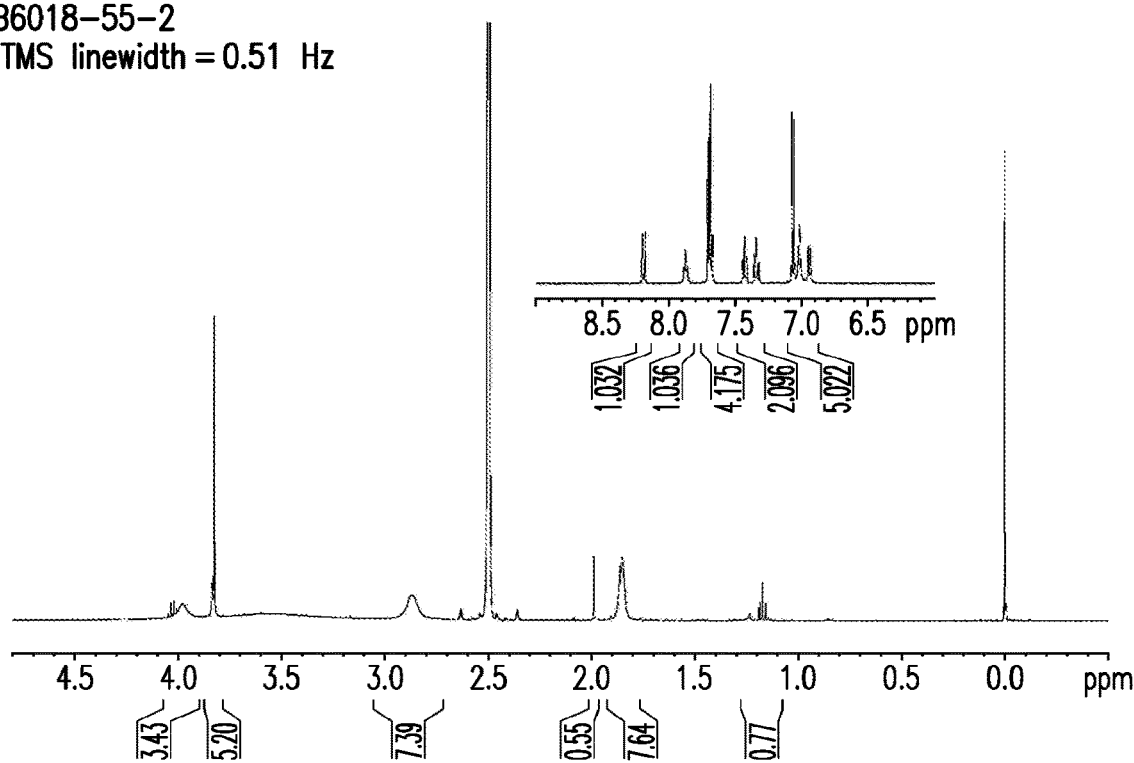
FIG. 8 is a representative $^1$H-NMR spectrum of Form I of a crystalline salt of sulcardine and 1-hydroxy-2-naphthoic acid.

The material was crystalline by XRPD (FIG. 6) and had peaks at positions detailed in Table 4. There was a 3.5% mass loss in the TG up to decomposition (1.3 eq. water) and a single melting event in the DTA with an onset temperature of 161° C. (FIG. 7). 1-Hydroxy-2-naphthoic acid (1.0 eq.) was observed in the $^1$H-NMR and no significant solvent was observed (FIG. 8).

Example 7—1-Hydroxy-2-Naphthoic Acid Salt Form II

To sulcardine free base was added 1M 1-hydroxy-2-naphthoic acid stock solution in THE (1.05 eq.) and toluene (20 vol.). The sample was temperature cycled between ambient temperature and 40° C. in 4 hr cycles for ca. 72 hr and then placed in a fridge for ca. 24 hr. The vial containing the sample was uncapped and the solvent was allowed to evaporate, leaving a white and brown solid.

The material was crystalline by XRPD. There was a 1.1% mass loss in the TG up to decomposition and a single melting event in the DTA with an onset temperature of 166° C. 1-Hydroxy-2-naphthoic acid (1.0 eq.) was observed in the $^1$H-NMR and no significant solvent was observed.

Example 8—1-Hydroxy-2-naphthoic Acid Salt Scale-up for Form II

To 200 mg of sulcardine free base, 2 mL of toluene and 457 microliters of a 1 M solution of 1-hydroxy-2-naphthoic acid in THE was added. The sample was temperature cycled in accordance with Example 16. The solid was filtered using a Buchner funnel and filter dried for about 15 minutes.

Figure 11:
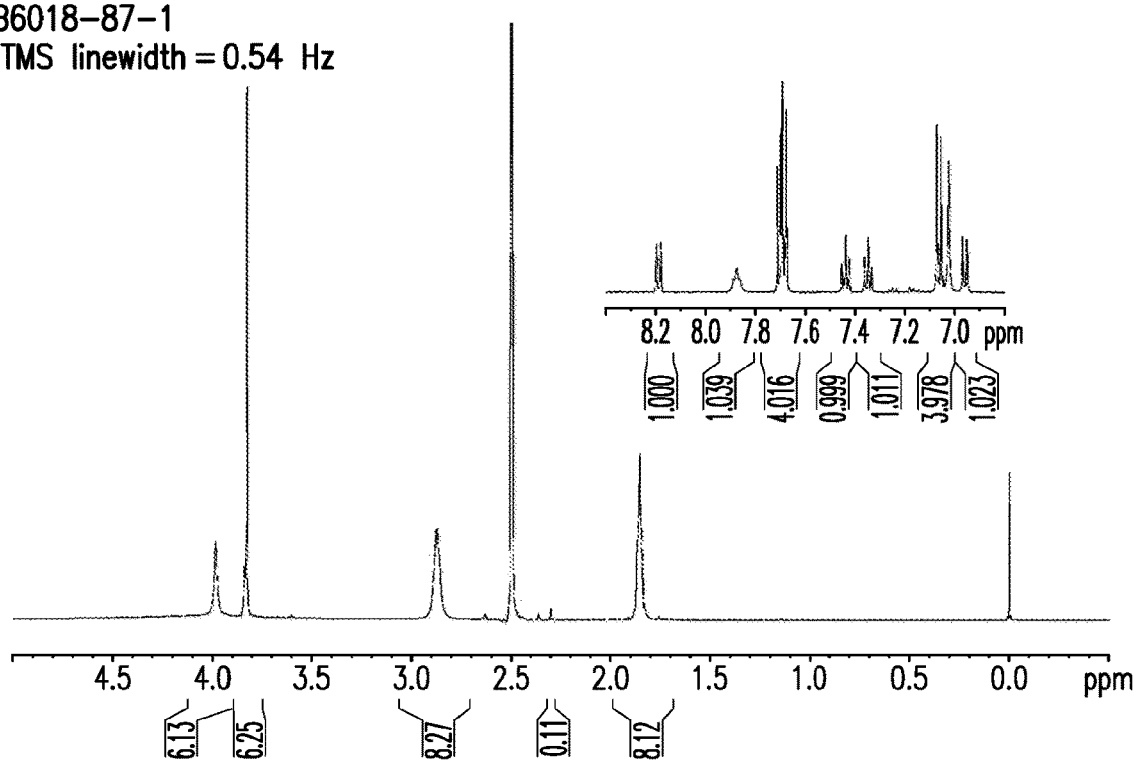
FIG. 11 is a representative $^1$H-NMR spectrum of Form II of a crystalline salt of sulcardine and 1-hydroxy-2-naphthoic acid.

The material was crystalline by XRPD (FIG. 9) and had peaks at positions detailed in Table 5. There was no mass loss in the TG up to decomposition and a single melting event in the DTA with an onset temperature of about 168° C. (FIG. 10). 1-Hydroxy-2-naphthoic acid (1.0 eq.) was observed in the $^1$H-NMR and no significant solvent was observed (FIG. 11). The solubility was measured to be 16.8 mg·mL-1 in pH 1.2 buffer, 4.2 mg·mL-1 in pH 3.0 buffer, 6.1 mg·mL-1 in pH 4.0 buffer and 0.2 mg·mL-1 in pH 7.4 buffer (Table 6).

Example 9—Naphthalene-2-Sulfonic Acid Salt

To sulcardine free base was added 1M naphthalene-2-sulfonic acid stock solution in THE (1.05 eq.) and ethyl acetate (20 vol.). The sample was temperature cycled between ambient temperature and 40° C. in 4 hr cycles for ca. 72 hr. Heptane (10 vol.) was added and the sample was placed in a fridge for ca. 24 hr. The vial containing the sample was uncapped and the solvent was allowed to evaporate, leaving a white and orange solid.

The material was crystalline by XRPD. There was a 2.6% mass loss in the TG up to decomposition (1.0 eq. water) and a single melting event in the DTA with an onset temperature of 95° C. Naphthalene-2-sulfonic acid (1.0 eq.) was observed in the $^1$H-NMR and no significant solvent was observed.

Example 10—Naphthalene-2-Sulfonic Acid Salt Scale-Up

To 200 mg of sulcardine free base, 2 mL of toluene and 457 microliters of a 1 M solution of naphthalene-2-sulfonic acid in THF was added. The sample was temperature cycled in accordance with Example 16. The solid was filtered using a Buchner funnel and filter dried to obtain a white solid.

Figure 15:
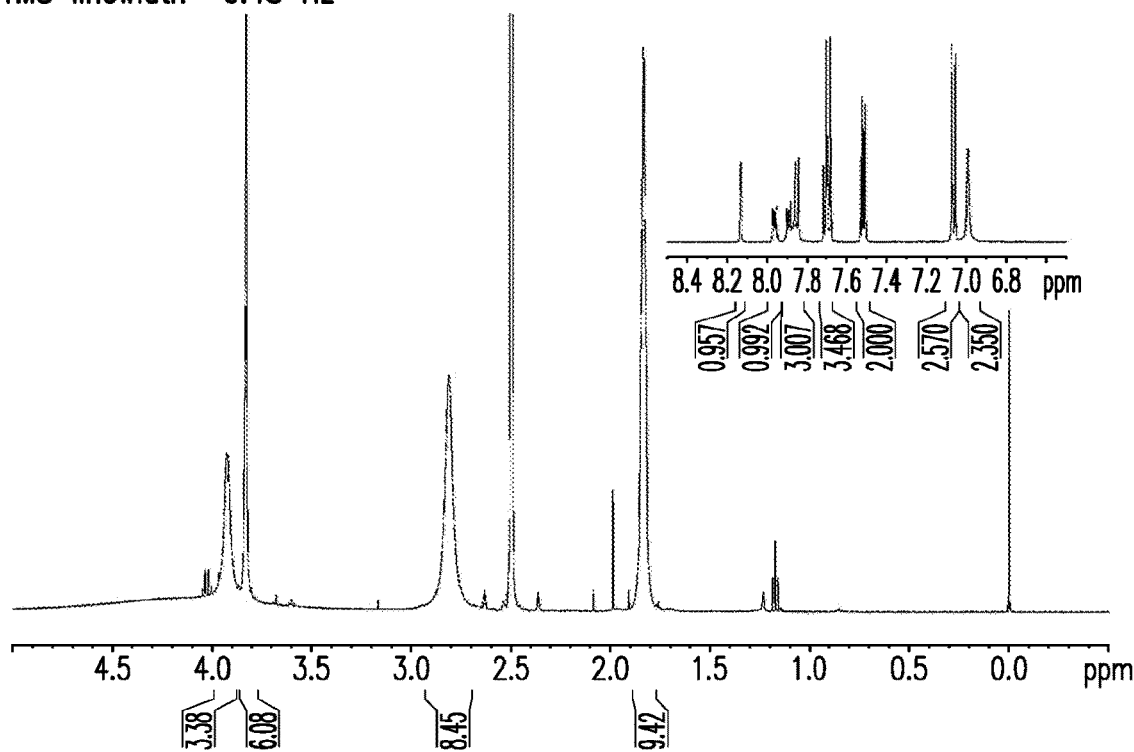
FIG. 15 is a representative $^1$H-NMR spectrum of a crystalline salt of sulcardine and naphthalene-2-sulfonic acid.

The material was crystalline by XRPD (FIG. 13) and had peaks at positions detailed in Table 7. There was a 2.4% mass loss in the TG up to decomposition (about 1.0 eq. water) and a single endothermic event in the DTA with an onset temperature of 88° C. (FIG. 14). Naphthalene-2-sulfonic acid (1.0 eq.) was observed in the $^1$H-NMR and no significant solvent was observed (FIG. 15). The solubility was measured to be 23.6 mg·mL-1 in pH 1.2 buffer, 10.3 mg·mL-1 in pH 3.0 buffer, 18.9 mg·mL-1 in pH 4.0 buffer and 5.9 mg·mL-1 in pH 7.4 buffer (Table 8).

Example 11—Hydrochloric Acid Salt (Form II)

To sulcardine free base was added 1M HCl stock solution in THF (1.05 eq.), 2-propanol (20 vol.) and heptane (10 vol.). The sample was temperature cycled between ambient temperature and 40° C. in 4 hr cycles for ca. 72 hr. Additional heptane (20 vol.) was added and the sample placed in a fridge for ca. 24 hr, leaving a white solid. The material was crystalline by XRPD (FIG. 17A).

Example 12—Hydrochloric Acid Salt Scale-up (Form I)

To 200 mg of sulcardine free base, 2 mL of THF and 457 microliters of a 1 M solution of hydrochloric acid in THF was added. The sample was temperature cycled in accordance with Example 16. The solid was filtered using a Buchner funnel and filter dried to obtain a white solid.

Figure 18A:
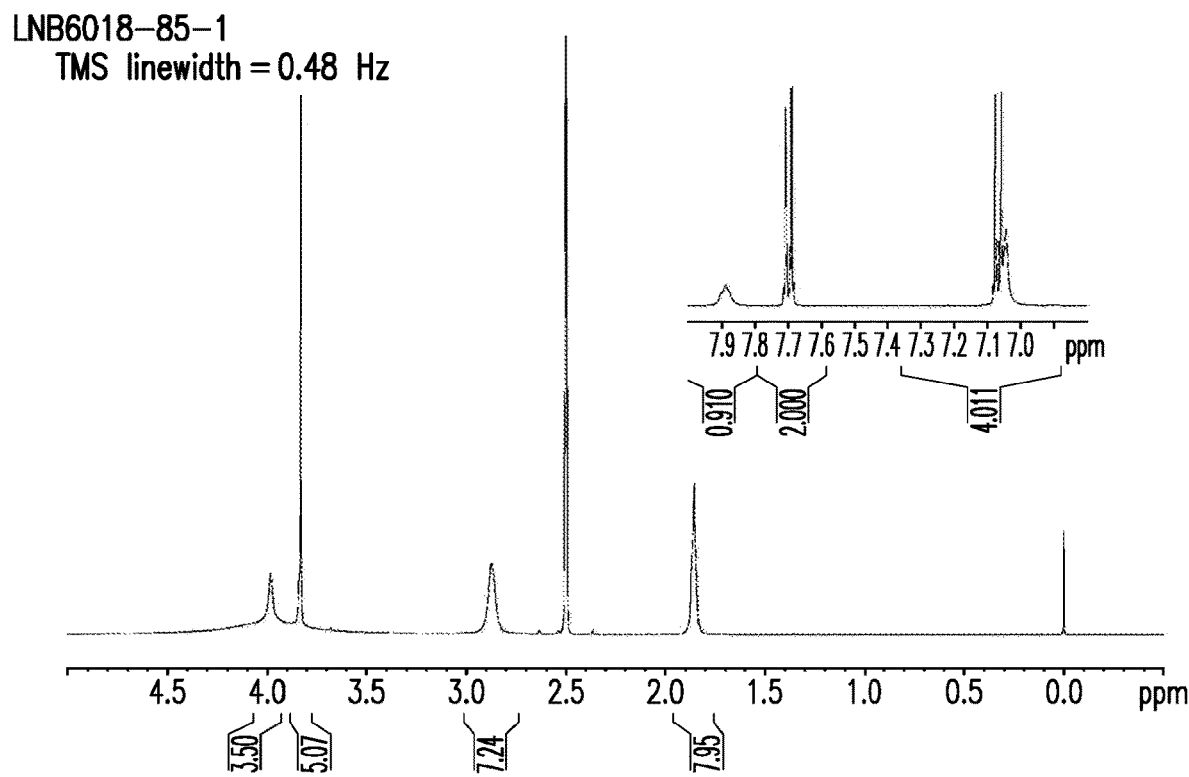
FIG. 18A is a representative $^1$H-NMR spectrum of Form I of a crystalline salt of sulcardine and hydrochloric acid.

The material was crystalline by XRPD (FIG. 17) and had peaks at positions detailed in Table 9. There was a 3.1% mass loss in the TG, equivalent to about 0.88 equivalents of water (FIG. 18). No solvent peaks were seen in the $^1$H-NMR (FIG. 18A).

Example 13—Ethane-1,2-Disulfonic Acid Salt

To sulcardine free base were added 1M ethane-1,2-disulfonic acid stock solution in THF (1.05 eq.), toluene (20 vol.) and heptane (10 vol.). The sample was temperature cycled between ambient temperature and 40° C. in 4 hr cycles for ca. 72 hr. Additional heptane (20 vol.) was added and the sample placed in a fridge for ca. 24 hr, leaving a white solid.

The material was crystalline by XRPD. There was a 1.4% mass loss in the TG up to decomposition and a single melting event in the DTA with an onset temperature of 201° C. Ethane-1,2-disulfonic acid (0.6 eq.) was observed in the $^1$H-NMR and no significant solvent was observed.

Example 14—Ethane-1,2-Disulfonic Acid Salt Scale-Up

To 200 mg of sulcardine free base, 2 mL of toluene and 218 μL of 1M ethane-1,2-disulfonic acid solution in THF (0.55 eq.) were added. The sample was temperature cycled in accordance with Example 16. The solid was filtered dried using a Buchner funnel to obtain a white solid.

The material was crystalline by XRPD (FIG. 19) and had peaks at positions detailed in Table 10. There was no mass loss in the TG up to decomposition and a single melting event in the DTA with an onset temperature of 211° C. (FIG. 20). Ethane-1,2-disulfonic acid (0.5 eq.) was observed in the $^1$H-NMR and no significant solvent was observed (FIG. 21). The solubility was measured to be 41.1 mg·mL-1 in pH 1.2 buffer, 46.3 mg·mL-1 in pH 3.0 buffer, 36.1 mg·mL-1 in pH 4.0 buffer and 18.9 mg·mL-1 in pH 7.4 buffer (Table 11).

Example 15—Hydrobromic Acid Salt

To sulcardine free base were added 1M HBr stock solution in THF (1.05 eq.), 2-propanol (20 vol.) and heptane (10 vol.). The sample was temperature cycled between ambient temperature and 40° C. in 4 hr cycles for ca. 72 hr. Additional heptane (20 vol.) was added and the sample placed in the fridge for ca. 24 hr. The vial containing the sample was uncapped and the solvent was allowed to evaporate, leaving an orange solid.

Figure 25:
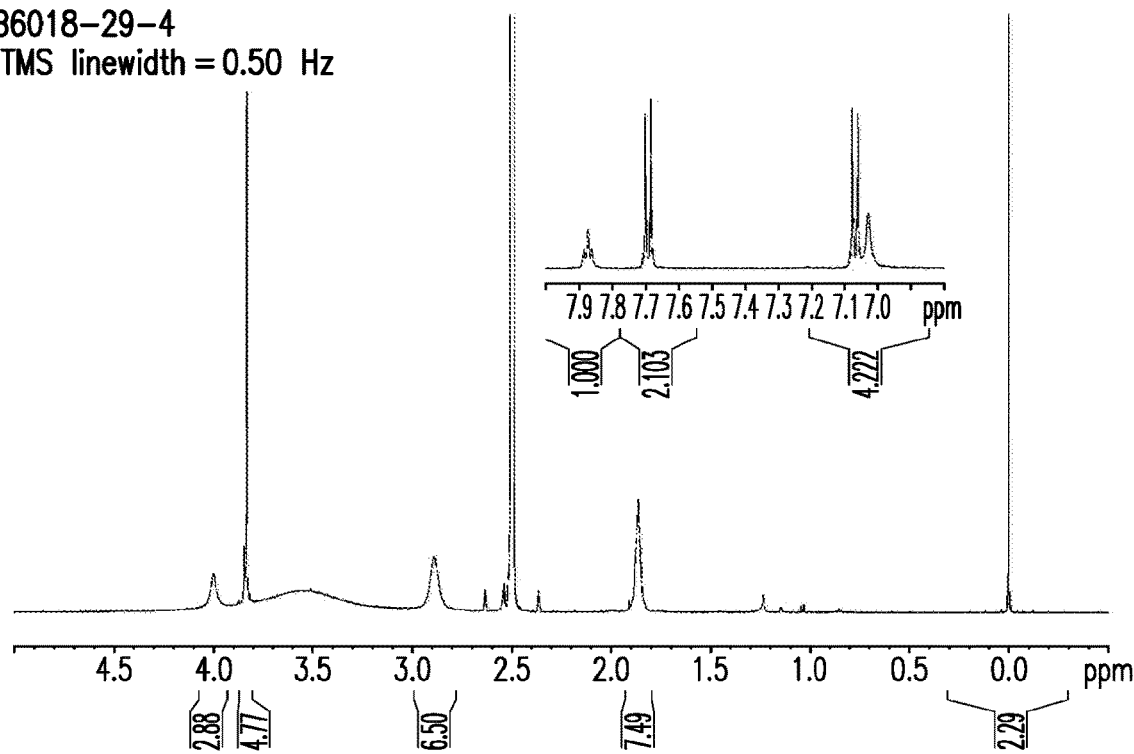
FIG. 25 is a representative $^1$H-NMR spectrum of a crystalline salt of sulcardine and hydrobromic acid.

The material was crystalline by XRPD (FIG. 23) and had peaks at positions detailed in Table 12. There was a 4.3% mass loss in the TG up to decomposition and no melting event in DTA (FIG. 24). There was no significant solvent present by $^1$H-NMR (FIG. 25).

Example 16—Temperature Cycling of Examples 5, 8, 10, 12, and 14

The temperatures were cycled with stirring using the following method:
1. Hold at 25° C. for 1 hour
2. Cool to 5° C. at 0.1° C./minute
3. Hold at 5° C. for 1 hour
4. Heat to 25° C. at 0.1° C./minute
5. Repeat for a total of 72 hours removing samples at 5° C.

Figure 32:
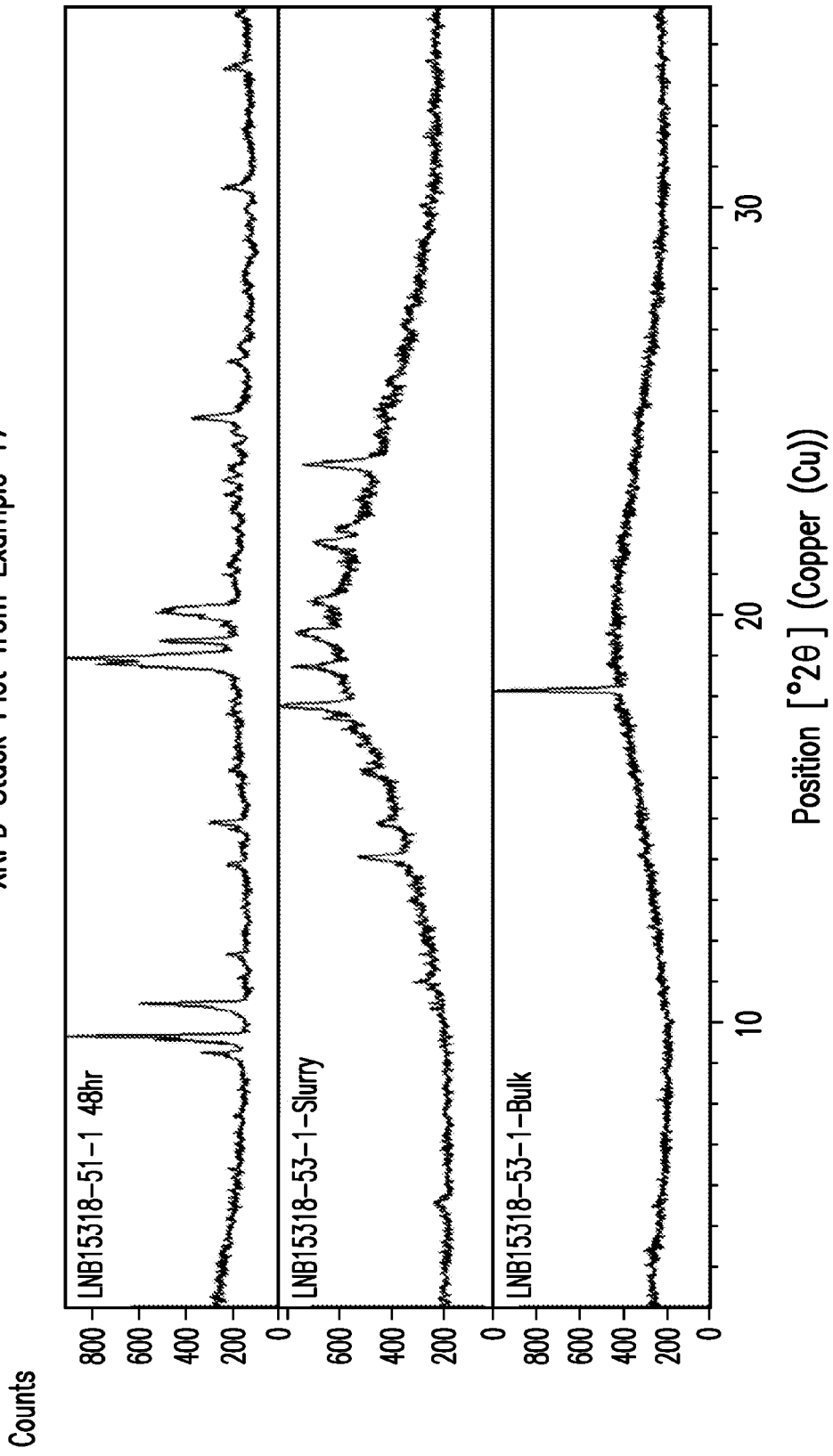
FIG. 32 is an XRPD stack plot from Example 17.
Figure 33:
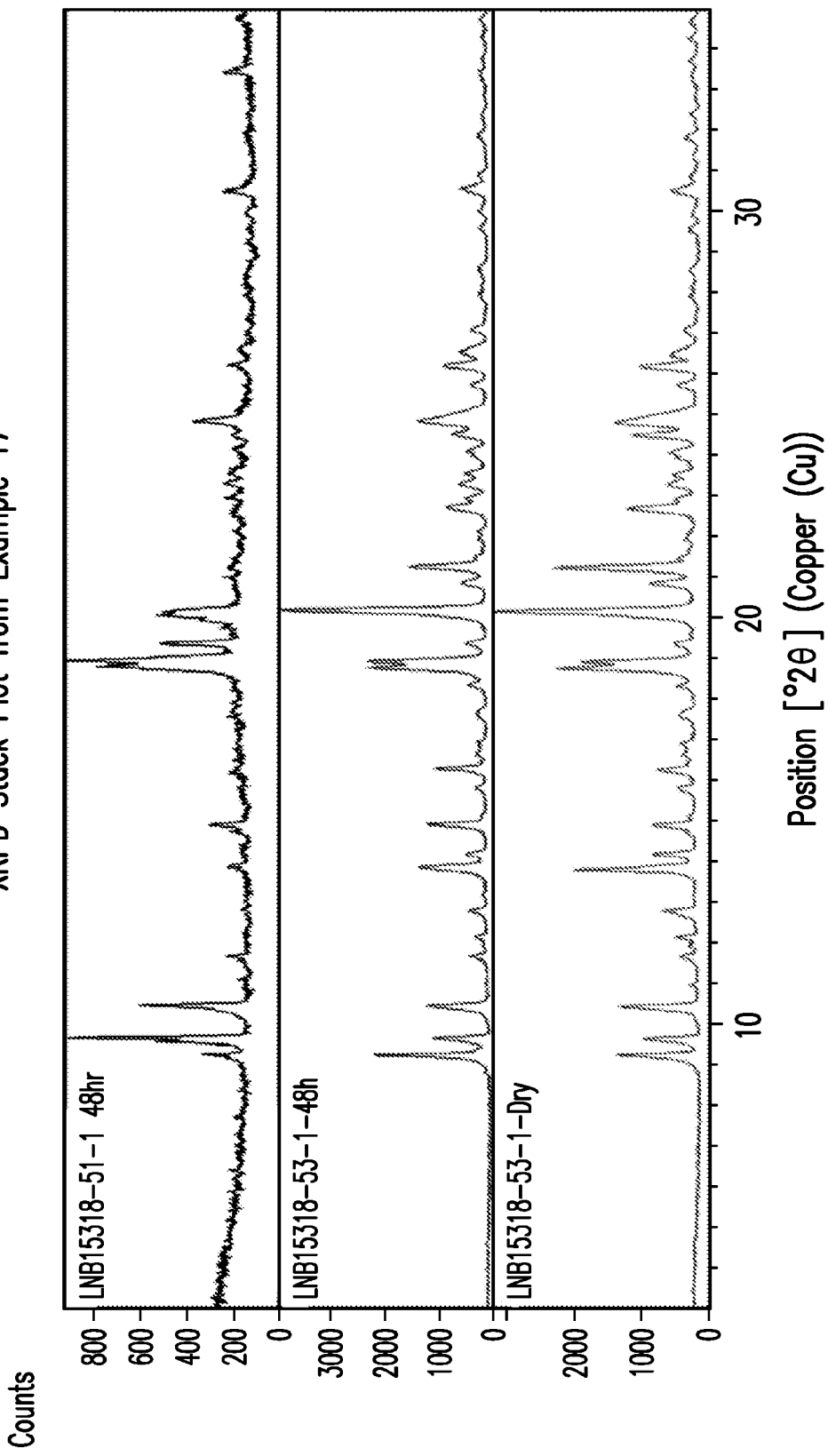
FIG. 33 is an XRPD stack plot from Example 17.

Example 17—Preparation of Form I of Crystalline Monoedisylate Salt of Sulcardine To a solution containing about 3 g of sulcardine free base, 45 mL of toluene was added to form a solution. To this solution, about 6.85 mL (1.05 eq.) of a 1M ethane-1,2-disulfonic acid stock solution (ethane-1,2-disulfonic acid dihydrate was used in THF) was added, forming a gum-like solid. The solution was temperature cycled between ambient and 40° C. in 4-hour cycles for about 24 hours. After 24 hours, a small amount of white free-flowing solid was observed in the flask, and a large mass of white gum-like material was observed in the flask. Both materials appeared predominantly amorphous by XRPD (diffraction patterns LNB15318-53-1-Slurry and LNB15318-53-1-Bulk in FIG. 32). The material was then temperature cycled for a further 24 hours. After 48 hours, a mixture of free-flowing off-white powder and agglomerates of off-white solid was observed in the flask. An aliquot of the free-flowing material was collected for XRPD analysis, and the pattern can be seen in FIG. 33 (diffraction pattern LNB15318-53-1-48 h). The material was filtered using Buchner filtration and dried under vacuum at ambient temperature for about 24 hours. The dried material was collected, weighed and analyzed by XRPD (diffraction pattern LNB15318-53-1-Dry in FIG. 26 and FIG. 33). The peak lists for Form I were generated using the diffraction pattern LNB15318-53-1-Dry.

Amorphous Monoedisylate Salt of Sulcardine:

During the polymorph screening of the monoedisylate salt, batches of material were lyophilized prior to carrying out experiments. Post-lyophilization the material appeared as a clear, colorless gum rather than a solid. $^1$H NMR analysis was carried out on the gum which confirmed the material was still a mono-edisylate salt.

Figure 34:
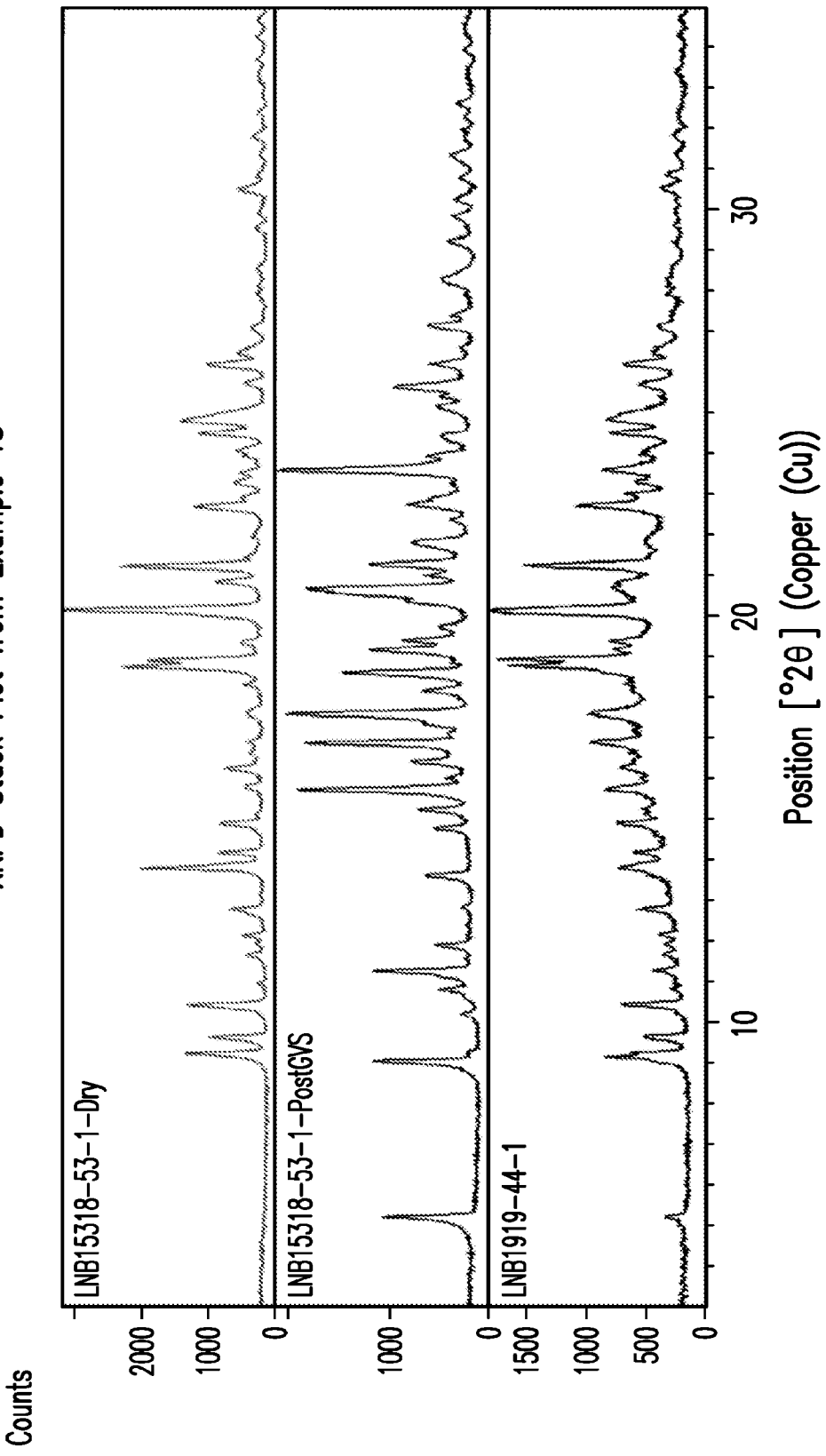
FIG. 34 is an XRPD stack plot from Example 18.
Figure 35:
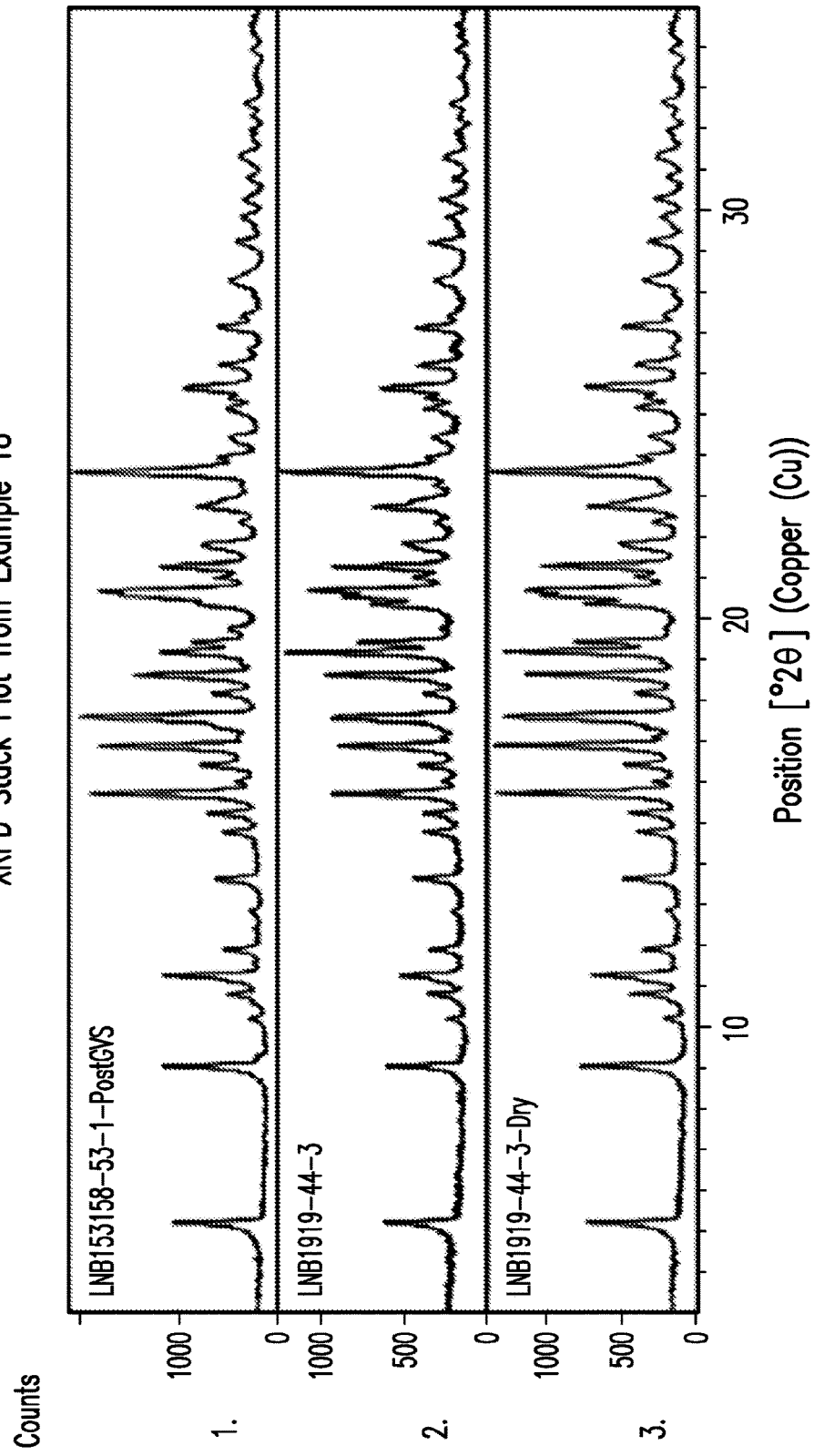
FIG. 35 is an XRPD stack plot from Example 18.

Example 18—Preparation of Form II of Crystalline Monoedisylate Salt of Sulcardine To a solution containing about 4 g of sulcardine free base, 60 mL of toluene was added to form a solution. To this solution, 9.34 mL (1.05 eq.) of 1M ethane-1,2-disulfonic acid stock solution (ethane-1,2-disulfonic acid dihydrate was used in THF) was added, forming a gum-like solid. The sample was temperature cycled between ambient and 40° C. in 4 hour cycles for about 96 hours with agitation. A free-flowing off-white powder was observed. A sample of wet solid was analysed by XRPD. The material appeared as a mixture of mono-edisylate Form I and what is now termed Form II (diffraction pattern LNB1919-44-1 in FIG. 34). The solid was isolated via Buchner filtration and dried at under vacuum at ambient temperature overnight. The dried material was collected and transferred to a 100 mL Duran flask. 40 mL of EtOH/water (0.4 aw) was added to form a mobile slurry. The slurry was then stirred at ambient temperature using a stirrer bar for about 120 hours. An aliquot of material was taken and analyzed by XRPD (diffraction pattern LNB1919-44-3 in FIG. 28 and FIG. 35). The material was identified as mono-edisylate Form II. The bulk material was isolated via Buchner filtration and dried under vacuum at ambient temperature for about 24 hours. The dried material was analyzed by XRPD (diffraction pattern LNB1919-44-3-Dry in FIG. 35), which also showed it to be Form II. The peak lists for Form II were generated using the diffraction pattern LNB1919-44-3-Dry.

Example 19—Reference Pattern Preparation—Form I of Crystalline Monoedisylate Salt of Sulcardine Approximately 100 mg of sulcardine free base was dissolved in 2 mL of toluene. To this, 229 μL of 1M ethane-1,2-disulfonic acid stock solution (ethane-1,2-disulfonic acid dihydrate was used in TIF) was added. The sample was temperature cycled between ambient and 40° C. in 4 hour cycles. An aliquot of the material was collected after approximately 24 hours and further temperature cycled for 24 hours. An aliquot of the material was taken and analyzed by XRPD. A unique crystalline pattern was observed. The pattern, LNB15318-51-1 48 hr in FIG. 32, was denoted mono-edisylate Form I.

Example 20—Reference Pattern Preparation—Form II of Crystalline Monoedisylate Salt of Sulcardine Form II was first observed during the GVS characterization of Form I. The material collected post-GVS analysis of Form I was analyzed by XRPD. A new pattern (denoted Form II) was observed indicating a higher-level hydrate was formed. The XRPD reference is "LNB15318-53-1-PostGVS" in FIG. 34.

Example 21—GVS (Gravimetric Vapor Sorption) for Example 20

Approximately 26 mg of Form I was placed into a mesh vapor sorption balance pan and loaded into an IGASorp Moisture Sorption Analyser balance by Hiden Analytical. The sample was subjected to a ramping profile from 40-90% relative humidity (RH) at 10% increments, maintaining the sample at each step until a stable weight had been achieved (98% step completion, minimum step length 30 minutes, maximum step length 60 minutes) at 25° C. After completion of the sorption cycle, the sample was dried using the same procedure to 0% RH, and finally taken back to the starting point of 40% RH. Two cycles were performed. The weight change during the sorption/desorption cycles were plotted, allowing for the hygroscopic nature of the sample to be determined. The material collected post-GVS analysis was analyzed by XRPD.

Example 22—KF Analysis

Approximately 30 mg of material for KF analysis was weighed into a pre-weighed glass vial. The material was then added into the titration cell of a KF coulometer containing Hydranal solution. The empty vial was back-weighed after addition of the solid to determine the mass of material added to the cell. The sample was then titrated. The analysis was carried out in duplicate and an average of the results calculated.

Figure 36:
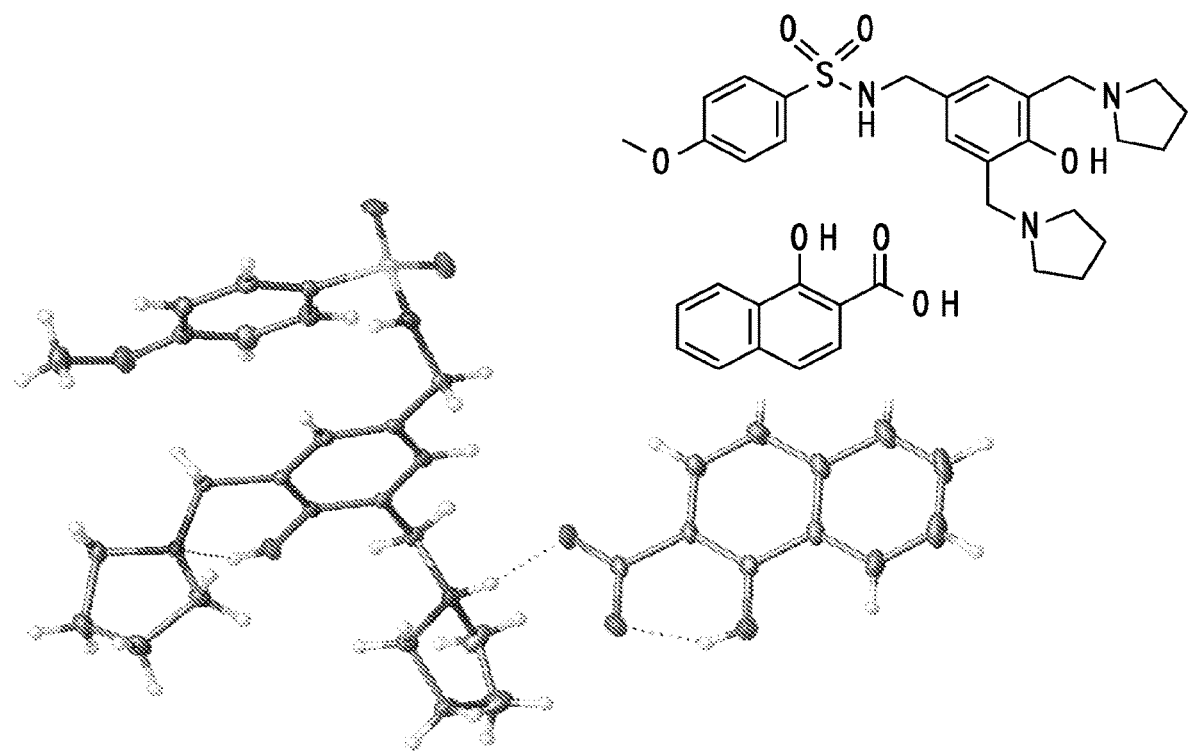
FIG. 36 is an overlay of the asymmetric unit containing one complete sulcardine 1-hydroxy-2-naphthoate formula unit and schematic representation of sulcardine 1-hydroxy-2-naphthoate. All non-hydrogen atoms are shown with thermal displacement ellipsoids set at the 50% probability level.

Example 23—Single Crystal X-Ray Analysis of Form II of 1-Hydroxy-2-Naphthoic Acid Salt of Sulcardine Single crystal X-ray analysis of Form II of 1-hydroxy-2-naphthoic acid salt of sulcardine was performed at 120 K using Mo Kα radiation (λ=0.71073 Å) generated by sealed tube using an Agilent Supernova single crystal X-ray diffractometer. All data was reduced, solved and refined in the monoclinic space-group P2$_1$/n (a=10.2443(2) Å, b=29.9171 (6) Å, c=10.8406(3) Å; β=103.375(2)°, volume=3232.31 (13) Å$^3$, Z=4, Z'=1). The final model was built using 123397 (11798 unique) reflections across the 2θ range 5.622 to 65.972° returning a R$_1$ (I>(2σI)) value of 5.79% confirming the expected structure of sulcardine. The asymmetric unit (FIG. 36) was shown to contain one complete sulcardine molecule with one associated 1-hydroxy-2-naphthoic acid counterion (1:1, sulcardine:counterion ratio). A characteristic experimental XRPD 2Θ diffractogram was calculated using the data collected at 120 K which was consistent with Form II of the salt. The crystal data are shown in Table 13.

TABLE 13

Crystallographic parameters and refinement indicators of
Form II of 1-hydroxy-2-naphthoic acid salt of sulcardine
Form II of 1-Hydroxy-2-Naphthoic Acid Salt of Sulcardine

| | |
|---|---|
| Empirical formula | $C_{35}H_{41}N_3O_7S$ |
| Formula weight | 647.77 |
| Temperature/K | 120(1) |
| Crystal system | Monoclinic |
| Space group | $P2_1/n$ |
| a/Å | 10.2443(2) |
| b/Å | 29.9171(6) |
| c/Å | 10.8406(3) |
| α/° | 90 |
| β/° | 103.375(2) |
| γ/° | 90 |
| Volume/Å³ | 3232.31(13) |
| Z, Z` | 4, 1 |
| $\rho_{calc}$ g/cm³ | 1.331 |
| μ/mm⁻¹ | 0.154 |
| F(000) | 1376.0 |
| Crystal size/mm³ | 0.367 × 0.258 × 0.136 |
| Radiation/Å | MoKα (λ = 0.71073) |
| 2Θ range for data collection/° | 5.622 to 65.972 |
| Index ranges | −15 ≤ h ≤ 15, −45 ≤ k ≤ 45, −16 ≤ l ≤ 16 |
| Reflections collected | 123397 |
| Independent reflections | 11798 [$R_{int}$ = 0.0414, $R_{sigma}$ = 0.0255] |
| Data/restraints/parameters | 11798/0/422 |
| S | 1.145 |
| Final R indexes [$F^2 > 2\sigma$ ($F^2$)] | $R_1$ = 0.0579, $wR_2$ = 0.1316 |
| Final R indexes [all data] | $R_1$ = 0.0673, $wR_2$ = 0.1357 |
| Δρmax, Δρmin/e Å⁻³ | 0.85/−0.39 |

$R_1 = (\Sigma|F_o| - |F_c|)/\Sigma|F_o|); wR_2 = \{\Sigma[w(F_o^2 - F_c^2)^2]/\Sigma[w(F_o^2)^2]\}^{1/2}; S = \{\Sigma[w(F_o^2 - F_c^2)^2]/(n - p)\}^{1/2}.$

Example 24—Infrared Spectroscopy Analysis of Form I and Form II of Monoedisylate Salt of Sulcardine Infrared spectroscopy was carried out on a Bruker ALPHA P spectrometer. Sufficient material was placed onto the center of the plate of the spectrometer and the spectra were obtained using the following parameters:

Resolution: 4 cm⁻¹

Background Scan Time: 16 scans

Sample Scan Time: 16 scans

Data Collection: 4000 to 400 cm⁻¹

Result Spectrum: Transmittance

Software: OPUS version 6

Figure 37C:
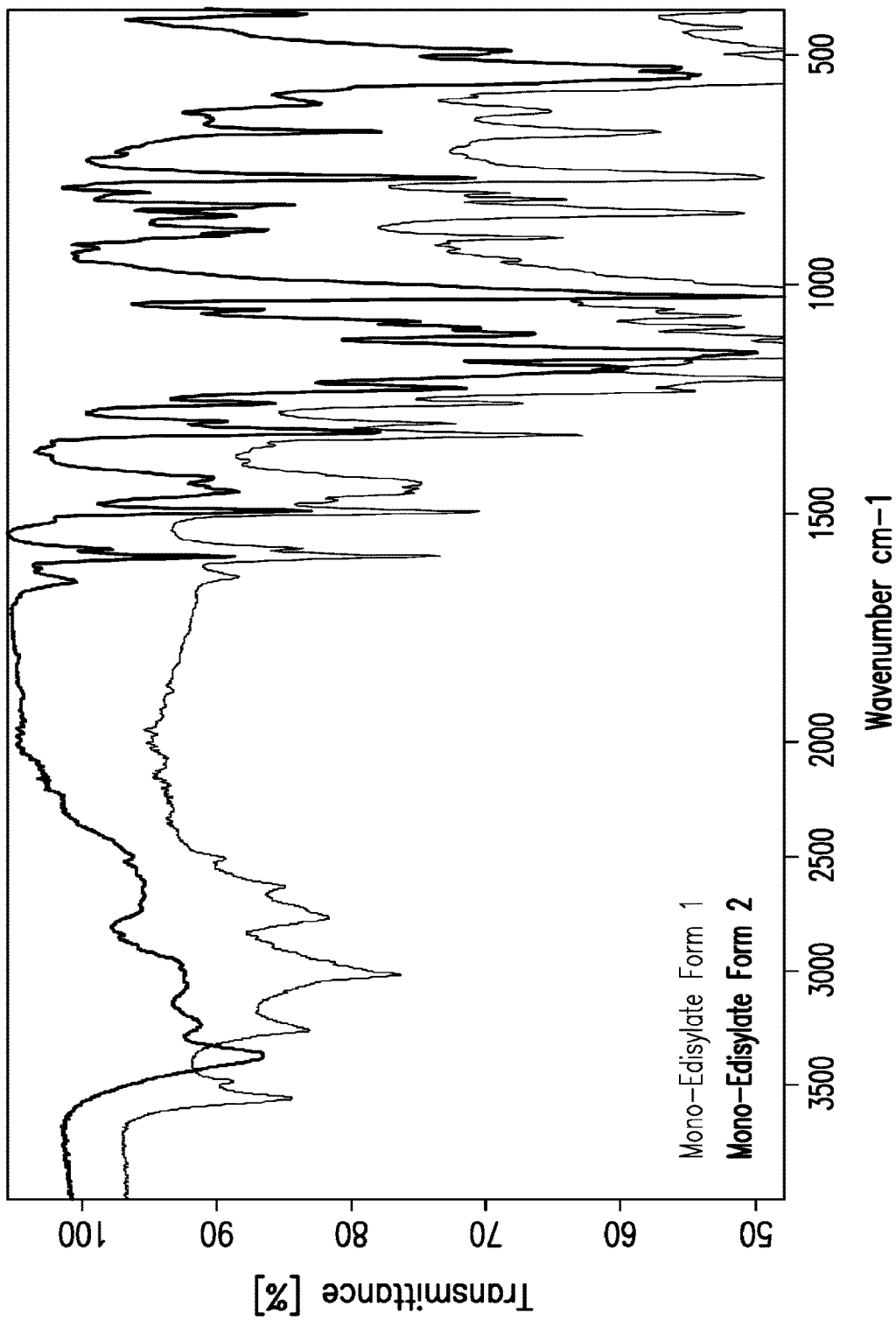
FIG. 37C is an overlay of FT-IR spectra of Form I and Form II of monoedisylate salt of sulcardine.

The FT-IR spectra are shown in FIG. 37A (Form I), FIG. 37B (Form II), and FIG. 37C (overlay).

Example 25—Thermodynamic Solubility Assessment of Selected Salt Forms

The thermodynamic solubility of the sulcardine sulfate trihydrate, naphthoate Form II (i.e., Form II of 1-hydroxy-2-naphthoic acid salt), and Form II of mono-edisylate salt were determined in the following media: 0.9% sodium chloride solution, and 5% dextrose in water.

Procedure: To 1 mL of selected media, the appropriate salt was added in ca. 10 mg aliquots to form a mobile slurry. The observed slurries were agitated at ambient temperature for ca. 16 hours. The samples were collected, and the pH was recorded. Additional solid was added to samples in which clear solutions were observed. The samples were agitated at ambient for a further 8 hours. The pH of the samples was recorded after 24 hours. The samples were filtered via centrifugation and the observed solids analyzed by XRPD. The mother liquors were submitted for HPLC analysis.

The thermodynamic solubility results are listed in Table 14.

TABLE 14

Thermodynamic Solubility Results

| Salt Form | Media | XRPD Results of Residual Solids | Purity (%) | Concentration (mg/mL) |
|---|---|---|---|---|
| Sulfate trihydrate | 0.9% Sodium Chloride | Sulfate trihydrate | >99.9 | 88.5 |
| | 5% Dextrose in Water | Sulfate trihydrate | >99.9 | 61.2 |
| Naphthoate Form II | 0.9% Sodium Chloride | Naphthoate Form II | 96.3 | 0.6 |
| | 5% Dextrose in Water | Naphthoate Form II | 95.7 | 0.4 |
| Mono-Edisylate Form II | 0.9% Sodium Chloride | Mono-Edisylate Form II (predominantly amorphous) | 99.5 | 303.4 |
| | 5% Dextrose in Water | Mono-Edisylate Form II (poorly crystalline) | 99.4 | 295.4 |

Example 26—Sulcardine Salts PK Analysis

Materials and Methods:

The pharmacokinetic objective of this study was to assess the exposure to sulcardine following oral capsule administration or intravenous (IV) infusion of sulcardine sulfate salt, sulcardine naphthoate salt, or sulcardine mono-edisylate salt (Form II) to male dogs during a pharmacokinetic study.

Non-naïve Beagle Dogs were fasted. Dosing formulations (oral [PO] capsule and intravenous [IV] infusion) were prepared on the day prior to dosing. The IV formulations were made in 10 mM Glycine (pH adjusted to 3.0±0.1), 3% Mannitol, qs in Sterile Water for Injection, USP were filtered through a 0.22 μm PVDF filter and stirred for at least 30 minutes prior to dosing. The capsule doses were encapsulated as active pharmaceutical ingredient powder into the appropriate number of size 12 gelatin capsules on the day prior to dosing.

Oral dosing was once on Day 1 by oral capsule administration; IV dosing was once on Day 1 by IV infusion over approximately 45 minutes (±2 minutes).

The blood samples for animals dosed orally were collected at 0.5, 1, 2, 3, 5, 8, 12, 18, 24, and 36 hours postdose. The blood samples for animals dosed IV were collected at approximately 0.33, 0.75 (end of infusion), 1.5, 3, 6, 9, 12, 18, and 24 hours post the start of infusion.

The blood samples were centrifuged under refrigerated (2° C. to 8° C.) conditions at 3,200 RPM for 10 minutes and the resulting plasma was divided into two aliquots (150 μL and remaining) then frozen and shipped for bioanalysis. Plasma samples were analyzed for concentrations of sulcardine by Citoxlab North America, Laval, Québec, Canada.

Individual sulcardine plasma concentration time profiles from sulcardine sulfate salt, sulcardine mono-edisylate salt, or sulcardine naphthoate salt treated animals were analyzed using model-independent methods (Gibaldi M, Perrier D. Pharmacokinetics. $2^{nd}$ ed. New York: Marcel Dekker, Inc., 1982:409-17). Pharmacokinetic parameters were obtained/calculated for each animal on Day 1.

Results—Plasma Levels

Figure 38A:
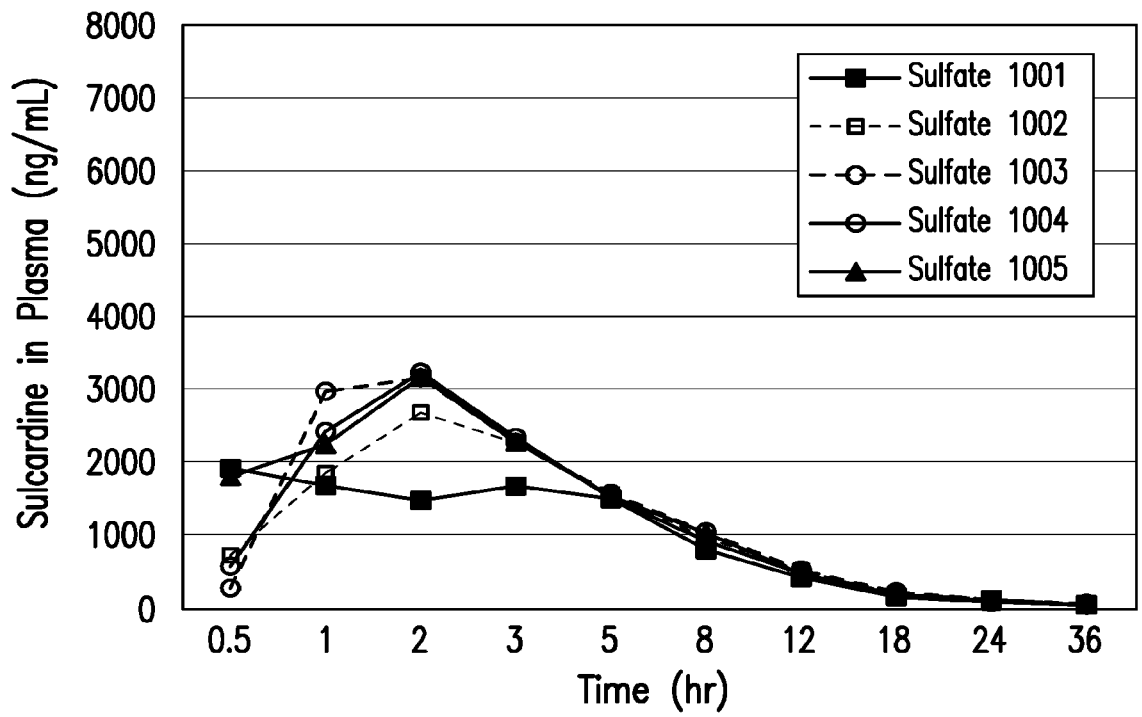
FIG. 38A shows plasma concentration of sulcardine following a single oral administration of sulcardine sulfate salt.
Figure 38B:
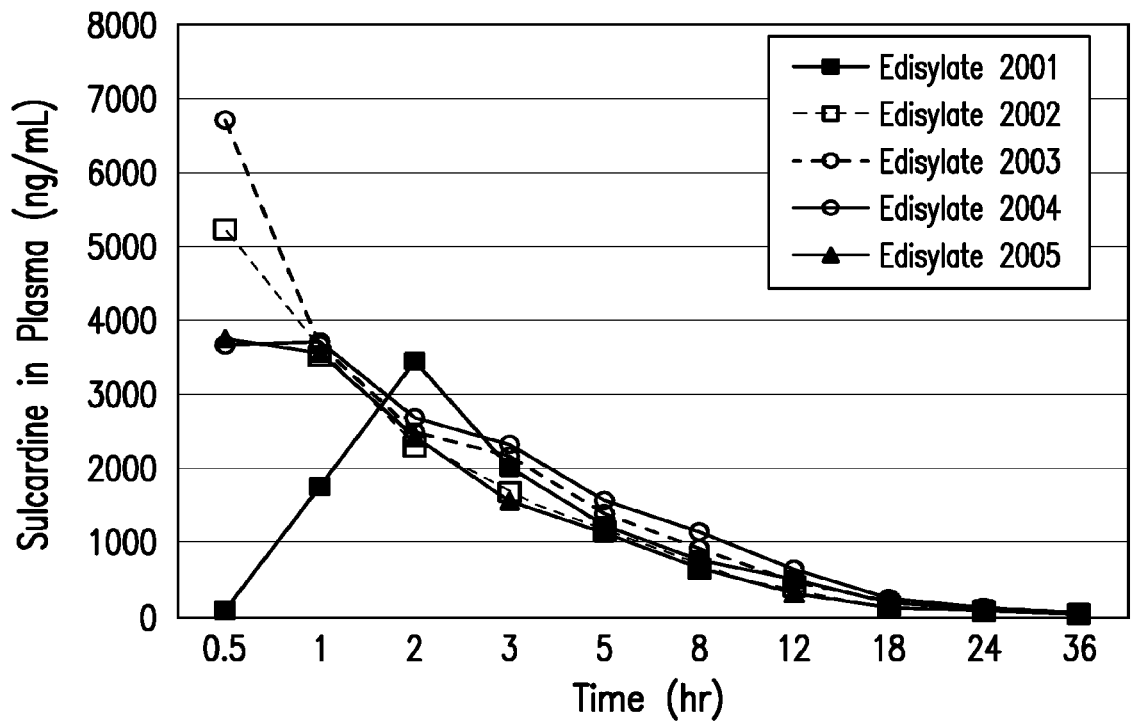
FIG. 38B shows plasma concentration of sulcardine following a single oral administration of sulcardine monoedisylate salt.

Following a single oral administration of sulcardine, Cmax values were 2820 ng/mL for the sulfate salt formulation group (FIG. 38A), 4570 ng/mL for the mono-edisylate salt formulation group (FIG. 38B). Average pharmacokinetic parameters were calculated using data from all animals in each group. Values for the oral mono-edisylate group included animal 2001 (FIG. 38B), which appears to be an outlier and may reflect an error in dosing. Without the data from animal 2001, the Cmax value for the mono-edisylate salt formulation group will likely be higher than 4570 ng/mL. Median peak sulcardine plasma concentrations were observed by 2 hour postdose for the sulcardine sulfate salt formulation group (Tmax 2 hr) and by 0.5 hours postdose (Tmax 0.5 hr) for the mono-edisylate salt formulation group.

This profile of faster Tmax and higher Cmax observed with oral dosing of the mono-edisylate versus the sulfate salt (likely due to increased solubility of the edisylate salt form) may provide advantages for an immediate release formulation, which would allow more rapid treatment of acute atrial fibrillation.

Based upon human clinical data demonstrating a linear concentration-effect relationship between plasma levels of sulcardine and a number of specific ECG parameter changes associated with its ion channel blocking mechanism (e.g., increases in QRS consistent with block of $I_{Na-Peak}$ and increases in PR interval consistent with both $I_{Na-Peak}$ and $I_{Ca,L}$ inhibition) as reported in Mason et al., *Circulation* 140:A11495 (2019) and as described in U.S. application Ser. No. 16/712,677 (the entireties of both are incorporated herein by reference), as well as supporting data from animal models, one would expect the mono-edisylate to elicit significantly higher pharmacodynamic effects (ECG changes) than the sulfate salt at T=0.5 hr after oral dosing. This is further expected to translate into faster efficacy with the mono-edisylate form versus the sulfate form.

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A method of treating arrhythmia, comprising administering to a subject in need thereof a therapeutically effective amount of a solid form comprising an acid salt of sulcardine, wherein the acid is ethane-1,2-disulfonic acid, wherein the arrhythmia is atrial fibrillation, supraventricular tachyarrhythmia, premature ventricular contraction, ventricular tachycardia, or ventricular fibrillation.

2. The method of claim 1, wherein the solid form is characterized by an XRPD pattern comprising peaks at approximately 14.1, 17.8, and 23.7° 2θ.

3. The method of claim 1, wherein the ethane-1,2-disulfonic acid salt is a hemi-ethane-1,2-disulfonic acid salt of sulcardine.

* * * * *